(12) United States Patent
Bergens et al.

(10) Patent No.: US 9,745,332 B2
(45) Date of Patent: Aug. 29, 2017

(54) CATALYSTS AND PROCESSES FOR THE HYDROGENATION OF AMIDES

(75) Inventors: Steven Bergens, Alberta (CA); Jeremy M. John, Alberta (CA)

(73) Assignee: The Governors of the Univerity of Alberta, Alberta (CA)

( * ) Notice: Subject to any disclaimer, the term of this patent is extended or adjusted under 35 U.S.C. 154(b) by 0 days.

(21) Appl. No.: 14/234,344

(22) PCT Filed: Jul. 18, 2012

(86) PCT No.: PCT/CA2012/050489
§ 371 (c)(1),
(2), (4) Date: Feb. 11, 2014

(87) PCT Pub. No.: WO2013/010275
PCT Pub. Date: Jan. 24, 2013

(65) Prior Publication Data
US 2014/0163225 A1    Jun. 12, 2014

Related U.S. Application Data

(60) Provisional application No. 61/508,766, filed on Jul. 18, 2011.

(51) Int. Cl.
*C07F 15/00* (2006.01)
*C07C 209/50* (2006.01)
(Continued)

(52) U.S. Cl.
CPC ....... *C07F 15/0053* (2013.01); *B01J 31/1805* (2013.01); *B01J 31/189* (2013.01);
(Continued)

(58) Field of Classification Search
CPC .. C07F 15/0046; C07F 15/0053; C07C 41/26; C07C 29/149; C07C 303/40;
(Continued)

(56) References Cited

U.S. PATENT DOCUMENTS 4,448,998 A    5/1984    King
7,763,758 B2   7/2010    Saudan et al.
(Continued)

FOREIGN PATENT DOCUMENTS

CA    2 765 607 A1    12/2010
EP    2 161 251 A1    10/2010
(Continued)

OTHER PUBLICATIONS

Supplementary European Search Report dated Dec. 8, 2015, in connection with corresponding EP Application No. 12815389 (8 pgs.).

(Continued)

*Primary Examiner* — Porfirio Nazario Gonzalez
(74) *Attorney, Agent, or Firm* — Maier & Maier, PLLC

(57) ABSTRACT

There is provided a process for the reduction of one or more amide moieties in a compound comprising contacting the compound with hydrogen gas and a transition metal catalyst in the presence or absence of a base under conditions for the reduction an amide bond. The presently described processes can be performed at low catalyst loading using relatively mild temperature and pressures, and optionally, in the presence or absence of a base or high catalyst loadings using low temperatures and pressures and high loadings of base to effect dynamic kinetic resolution of achiral amides.

22 Claims, 20 Drawing Sheets

(51) Int. Cl.

| | | |
|---|---|---|
| C07C 213/00 | (2006.01) | |
| C07D 295/027 | (2006.01) | |
| C07B 31/00 | (2006.01) | |
| B01J 31/18 | (2006.01) | |
| B01J 31/24 | (2006.01) | |
| C07C 303/40 | (2006.01) | |
| C07C 231/08 | (2006.01) | |
| C07D 201/02 | (2006.01) | |
| C07D 295/023 | (2006.01) | |
| C07C 29/149 | (2006.01) | |
| C07C 41/26 | (2006.01) | |

(52) U.S. Cl.
CPC ....... *B01J 31/2409* (2013.01); *B01J 31/2452* (2013.01); *C07B 31/00* (2013.01); *C07C 29/149* (2013.01); *C07C 41/26* (2013.01); *C07C 209/50* (2013.01); *C07C 213/00* (2013.01); *C07C 231/08* (2013.01); *C07C 303/40* (2013.01); *C07D 201/02* (2013.01); *C07D 295/023* (2013.01); *C07D 295/027* (2013.01); *C07F 15/0046* (2013.01); *B01J 2231/643* (2013.01); *B01J 2531/0244* (2013.01); *B01J 2531/0255* (2013.01); *B01J 2531/0266* (2013.01); *B01J 2531/821* (2013.01); *C07B 2200/07* (2013.01)

(58) Field of Classification Search
CPC ... C07C 231/08; C07C 209/50; C07C 213/00; C07D 201/02; C07D 295/023; C07D 295/027; C07B 31/00; B01J 31/2452; B01J 31/2409; B01J 31/189; B01J 31/1805
USPC ........... 544/106; 556/19; 564/413, 414, 487, 564/488
See application file for complete search history.

(56) References Cited

U.S. PATENT DOCUMENTS

| | | |
|---|---|---|
| 2010/0010261 A1 | 1/2010 | Eastham et al. |
| 2010/0280273 A1 | 11/2010 | Saudan et al. |

FOREIGN PATENT DOCUMENTS

| | | |
|---|---|---|
| WO | 03/093208 A1 | 11/2003 |
| WO | 2006/106484 A1 | 10/2006 |
| WO | 2006106483 A1 | 10/2006 |
| WO | 2008/065588 A1 | 6/2008 |
| WO | 2009006734 A1 | 1/2009 |
| WO | 2009137932 A1 | 11/2009 |
| WO | 2010/038209 A1 | 4/2010 |
| WO | 2010043027 A1 | 4/2010 |
| WO | 2010/073974 A1 | 7/2010 |
| WO | 2010145024 A1 | 12/2010 |
| WO | 2012/102247 A1 | 8/2012 |

OTHER PUBLICATIONS

T. Ikariya, et al., "Practical method for reducing amides and lactams", XP002751153, Database CASEREACT, Chemical Abstracts, retrieved from stn Database accession No. 153:115688, Abstract (4 pgs).

M. Ito, et al., "Catalytic Hydrogenation of Carboxamides and Esters by Well-Defined Cp*Ru Complexes Bearing a Protic Amine Ligand", in the Journal of the American Chemical Society, vol. 33, No. 12, Mar. 7, 2011, pp. 4240-4242 (3 pgs.).

M. Ito, et al., "Chemoselective Hydrogenation of Imides Catalyzed by Cp*Ru(PN) Complexes and its Application to the Asymmetric Synthesis of Paroxetine", in the Journal of the American Chemical Society, vol. 129, No. 2, Jan. 17, 2007, pp. 290-291 (2 pgs.).

Ito, M. et al. Hydrogenation of N-Acylcarbamates and N-Acylsulfonamides Catalyzed by a Bifunctional [Cp*Ru(PN)] Complex; Agnew. Chem. Int. Ed.; 2009, vol. 48, pp. 1324-1327; ISSN: 1521-3773.

Magro, A., A., M. et al. The synthesis of amines by the homogeneous hydrogenation of secondary and primary amides.; Chem. Commun.; 2007; pp. 3154-3156; ISSN: I359-7345.

Balaraman et al. Direct Hydrogenation of Amides to Alcohols and Amines under Mild Conditions.; J. Am. Chem. Soc.; 20 I 0, vol. 132, pp. 16756-16758; ISSN: 0002-7863.

Hamilton, R. J. et al.; A Ruthenium-Dihydrogen Putative Intermediate in Ketone Hydrogenation.; J. Am. Chem. Soc.; 2005; vol. 127; p. 4152-4153; ISSN: 0002-7863.

Blaquiere, N. et al. Ruthenium-Catalyzed Dehydrogenation of Ammonia Boranes. J. Am. Chem. Soc.; 2008, vol. 130, p. 14034-14035; ISSN: 1521-3773.

Takebayashi, S. et al. Experimental Investigations of a Partial Ru—O Bond during the Metal-Ligand Bifunctional Addition in Noyori-Type Enantioselective Ketone Hydrogenation. J. Am. Chem. Soc. 2011, vol. 133, p. 9666-9669; ISSN: 0002-7863.

Takebayashi, S. et al. Desymmetrization of meso-Cyclic Imides via Enantioselective Monohydrogenation. J. Am. Chem. Soc. 2010; vol. 132; p. 12832-12834; ISSN: 0002-7863.

Tak.Ebayash!, S. et al. Facile Bifunctional Addition of Lactones and Esters at Low Temperatures. The First Intermediates in Lactone/Ester Hydrogenations. ORGANOMETALLICS. Apr. 27, 2009; vol. 28, No. 8 p. 2349-2351; ISSN: 0276-7333.

Hamilton, R. J. et al. Direct Observations of the Metal-Ligand Bifunctional Addition Step in an Enantioselective Ketone Hydrogenation. J. Am. Chem. Soc, 2008, vol. 130, p. 11979-11987; ISSN:I521-3773.

Hamilton, R. J. et al. An Unexpected Possible Role of Base in Asymmetric Catalytic Hydrogenations of Ketones. Synthesis and Characterization of Several Key Catalytic Intermediates. J. Am. Chem. Soc. 2006 vol. 128, p. 137000-13701; ISSN: 0002-7863.

Hirano, M. et al. Synthesis of and Stereospecific Hydride Migration in Cationic (Tricyclic Arene)(Cyclooctadiene) Ruthenium(II) Complexes. ORGANOMETALLICS. 2002, vol. 21, p. 5738-5745; ISSN: 0276-7333.

Wiles, J. A. et al. An Alternate Route to the Active Chiral Hydrogenation Catalysts [Ru(bisphosphine)(H)(solvent)3] +: Synthesis, Characterization and Catalytic Evaluation. ORGANOMETALLICS, 2004; vol. 23 p. 24564-4568; ISSN: 0276-7333.

Wiles, J. A. et al. [Ru((R)-2,2'-bis(diphenylphosphino)-1,1'-binaphthyl)(H)-(MeCN)(THF)2]BF4), a Catalyst System for Hydrosilylation of Ketones and for Isomerization, Intramolecular Hydrosilylation and Hydrogenation of Olefins. ORGANOMETALLICS, 1996, vol. 15, p. 2782-2784; ISSN: 0276-7333.

International Search Report for International Application No. PCT/CA2012/050489 mailed Sep. 25, 2012.

International Preliminary Report on Patentability for International Application No. PCT/CA2012/050489 completed Oct. 31, 2013.

Extended European Search Report dated Apr. 8, 2016, including the Supplementary European Search Report and the European Search Opinion, in connection with corresponding EP Application No. 12815389.7 (22 pgs.).

G. Barbe, et al., "Highly Chemoselective Metal-Free Reduction of Tertiary Amides", in the Journal of American Chemical Society, vol. 130, No. 1, 2008, pp. 18 and 19 (2 pgs.).

G. Beamson, et al., "Selective Hydrogenation of Amides using Ruthenium/Molybdenum Catalysts", in Advanced Synthesis Catalysts, vol. 352, 2010, pp. 869-883 (15 pgs.).

G. Beamson, et al., "Selective hydrogenation of amides using Rh/Mo catalysts", in Journal of Catalysis, vol. 269, 2010, pp. 93-102 (10 pgs.).

G. Beamson, et al., "Selective hydrogenation of amides using bimetallic Ru/Re and Rh/Re catalysts", in Journal of Catalysis, vol. 278, 2011, pp. 228-238 (11 pgs.).

J. S. Carey, et al., "Analysis of the reactions used for the preparation of drug candidate molecules", in Organic & Biomolecular Chemistry, vol. 4, 2006, pp. 2337-2347 (11 pgs.).

(56) References Cited

OTHER PUBLICATIONS

C. Cheng, et al., "Iridium-Catalyzed Reduction of Secondary Amides to Secondary Amines and Imines by Diethylsilane", in Journal of the American Chemical Society, vol. 134, 2012, pp. 11304-11307 (4 pgs.).

S. Das, et al., "Zinc-Catalyzed Reduction of Amides: Unprecedented Selectivity and Functional Group Tolerance", in Journal of the American Chemical Society, vol. 132, 2010, pp. 1770-1771 (2 pgs.).

G. W. Gribble, "Sodium borohydride in carboxylic acid media: a phenomenal reduction system", in Chemical Society Reviews, vol. 27, 1998, pp. 395-404 (10 pgs.).

R. J. Hamilton, et al., "Direct Observations of the Metal-Ligand Bifunctional Addition Step in an Enantioselective Ketone Hydrogenation", in Journal of the American Chemical Society, vol. 130, 2008, pp. 11979-11987 (9 pgs.).

C. Hirosawa, et al., "Hydrogenation of Amides by the Use of Bimetallic Catalysts Consisting of Group 8 to 10, and Group 6 or 7 Metals", in Tetrahedron Letters, vol. 37, No. 37, 1996, pp. 6749-6752 (4 pgs.).

M. W. Irvine, et al., "Rhodanine derivatives as novel inhibitors of PDE4", in Science Direct, Bioorganic & Medicinal Chemistry Letters, vol. 18, 2008, pp. 2032-2037 (6 pgs.).

M. Ito, et al., "Highly Enantioselective Hydrogenative Desymmetrization of Bicyclic Imides Leading to Multiply Functionalized Chiral Cyclic Compounds", in Journal of the American Chemical Society, vol. 132, 2010, pp. 11414-11415 (4 pgs.).

J. M. John, et al., "A Highly Active Catalyst for the Hydrogenation of Amides to Alcohols and Amines**", in Angewandte Chemie, vol. 50, 2011, pp. 10377-10380 (4 pgs.).

G. Pelletier, et al., "Controlled and Chemoselective Reduction of Secondary Amides", in Journal of the American Chemical Society, vol. 132, 2010, pp. 12817-12819 (3 pgs.).

L. A. Saudan, "Hydrogenation Processes in the Synthesis of Perfumery Ingredients", in Accounts of Chemical Research, vol. 40, No. 12, 2007, pp. 1309-1319 (11 pgs.).

L. A. Saudan, et al., "Dihydrogen Reduction of Carboxylic Esters to Alcohols under the Catalysis of Homogeneous Ruthenium Complexes: High Efficiency and Unprecedented Chemoselectivity", in Angewandte Chemie, vol. 46, pp. 7473-7476 (4 pgs.).

D. R. Stuart, et al., "Indole Synthesis via Rhodium Catalyzed Oxidative Coupling of Acetanilides and Internal Alkynes", in Journal of the American Chemical Society, vol. 130, 2008, pp. 16474-16475 (2 pgs.).

M. Sugahara, et al., "A Facile Copper-Catalyzed Ullmann Condensation: N-Arylation of Heterocyclic Compounds Containing an-NHCO-Moiety", in Chem. Pharm. Bull., vol. 45, No. 4, 1997, pp. 719-721 (3 pgs.).

Y. Sunada, et al., "Hydrosilane Reduction of Tertiary Carboxamides by Iron Carbonyl Catalysts**", in Angewandte Chemie, vol. 48, 2009, pp. 9511-9514 (4 pgs.).

B. Wojcik, et al., "Catalytic Hdrogenation of Amides to Amines", in Journal of the American Chemical Society, vol. 56, 1934, pp. 2419-2424 (6 pgs.).

Y-H Yang, et al., "Ring-Expanding Reaction of Cyclopropyl Amides with Triphenylphosphine and Carbon Tetrahalide", in Journal of Organic Chemistry, vol. 70, 2005, pp. 8645-8648 (4 pgs.).

399.951 MHz H1 1D in thf
temp 30.0C --> actual temp = 30.0, sw400 probe

Pulse Sequence: presat

@ RT and 4 atm H$_2$

@ RT ~1 atm H$_2$

@ -80°C ~ 1 atm Ar 399.946 MHz H1 1D in thf

Pulse Sequence: presat

Derived from [Ru(C$_3$H$_5$)(Ph$_2$PCH$_2$CH$_2$NH$_2$)$_2$]BF$_4$

Derived from [RuCl$_2$(Ph$_2$PCH$_2$CH$_2$NH$_2$)$_2$]

Top: Product: 4-phenylaminobutan-1-ol
Bottom: Starting Material: N-phenylpyrrolidin-2-one
299.971 MHz H1 1D in cdcl3 (ref. to CDCl3 @ 7.26 ppm), temp 27.0 C -> actual temp = 27.0 C, id300 probe
Pulse Sequence: s2pul Top: Product: 4-methylaminobutan-1-ol
Bottom: Starting Material: N-methylpyrrolidin-2-one
498.122 MHz H1 1D in cdcl3 (ref. to CDCl3 @ 7.26 ppm), temp 27.2 C -> actual temp = 27.0 C, autoxdb probe
Pulse Sequence: s2pul Top: Product: 5-phenylaminopentan-1-ol
Bottom: Starting Material: N-phenylpiperidone
498.122 MHz H1 1D in cdcl3 (ref. to CDCl3 @ 7.26 ppm), temp 27.2 C -> actual temp = 27.0 C, autoxdb probe
Pulse Sequence: s2pul Top: Product: 6-aminohexan-1-ol
Bottom: Starting Material: Caprolactam
499.815 MHz H1 1D in cdcl3 (ref. to CDCl3 @ 7.26 ppm), temp 27.7 C -> actual temp = 27.0 C, colddual probe
Pulse Sequence: s2pul

Top: Product: Benzyl Alcohol, Diphenylamine and Benzyl Benzoate (Tishchenko product)
Bottom: Starting Material: N,N-diphenylbenzamide
498.122 MHz H1 1D in cdcl3 (ref. to CDCl3 @ 7.26 ppm), temp 27.2 C -> actual temp = 27.0 C, autoxdb probe
Pulse Sequence: s2pul Top: Product: Benzyl Alcohol and N-methylaniline
Bottom: Starting Material: N-methyl-N-phenylbenzamide
498.122 MHz H1 1D in cdcl3 (ref. to CDCl3 @ 7.26 ppm), temp 27.2 C -> actual temp = 27.0 C, autoxdb probe
Pulse Sequence: s2pul Top: Product: Benzyl Alcohol and Piperidine
Bottom: Starting Material: 1-Benzoylpiperidine
498.122 MHz H1 1D in cdcl3 (ref. to CDCl3 @ 7.26 ppm), temp 27.2 C -> actual temp = 27.0 C, autoxdb probe Pulse Sequence: s2pul Top: Product: Benzyl Alcohol and Aniline
Bottom: Starting Material: Benzanilide
499.815 MHz H1 1D in cdcl3 (ref. to CDCl3 @ 7.26 ppm), temp 27.7 C -> actual temp = 27.0 C, colddual probe Pulse Sequence: s2pul Top: Product: Benzyl Alcohol and Methylamine
Bottom: Starting Material: N-methylbenzamide
498.122 MHz H1 1D in cdcl3 (ref. to CDC13 @ 7.26 ppm), temp 27.2 C -> actual temp = 27.0 C, autoxdb probe
Pulse Sequence: s2pul Top: Product: Diphenylamine and Ethanol (from reaction mixture; partially evaporated)
Bottom: Starting Material: N,N-diphenylacetamide
499.815 MHz H1 1D in cdcl3 (ref. to CDCl3 @ 7.26 ppm), temp 27.7 C -> actual temp = 27.0 C, colddual probe
Pulse Sequence: s2pul Top: Product: N-methylaniline and Ethanol (from reaction mixture; partially removed)
Bottom: Starting Material: N-methylacetanilide
498.122 MHz H1 1D in cdcl3 (ref. to CDC13 @ 7.26 ppm), temp 27.2 C -> actual temp = 27.0 C, autoxdb probe Pulse Sequence: s2pul Top: Product: Dimethylamine and Ethanol (Anthracene used as internal standard)
Bottom: Starting Material: N,N-dimethylacetamide
499.815 MHz H1 1D in cdcl3 (ref. to CDCl3 @ 7.26 ppm), temp 27.7 C -> actual temp = 27.0 C, colddual probe Pulse Sequence: s2pul

```
Top: Product: Aniline and Ethanol (from reaction mixture)
Bottom: Starting Material: Acetanilide
499.815 MHz H1 1D in cdcl3 (ref. to CDCl3 @ 7.26 ppm),
temp 27.7 C -> actual temp = 27.0 C, colddual probe
Pulse Sequence: s2pul
```

CATALYSTS AND PROCESSES FOR THE HYDROGENATION OF AMIDES

FIELD OF THE INVENTION

The present invention pertains to generally relates to processes for the hydrogenation of amides with transition metal catalysts, and catalysts therefor.

BACKGROUND

Alcohols and amines are ubiquitous in the synthesis of agrochemicals, pharmaceuticals (e.g. protection, deprotection), flavors, fragrances, and advanced materials. (A. Ricci, *Modern Amination Methods*, Wiley, New York, 2000; Modern reduction methods, (Eds.: P. G. Andersson, I. J. Munslow) Wiley, New York, 2008; J. S. Carey, D. Laffan, C. Thomson, M. T. Williams, *Org. Biomol. Chem.* 2006, 4, 2337.)

One approach to access these compounds is via the reduction of amides. Amides are however, the most stable carboxylic acid derivative. (C. M. Breneman, M. Martinov in *The Amide Linkage Structural Significance in Chemistry, Biochemistry, and Materials Science* (Eds.: A. Greenberg, C. M. Breneman, J. F. Liebman), John Wiley and Sons Ins., New Jersey, 2003, p. 1-33; M. B. Robin, F. A. Bovey, H. Basch in *The Chemistry of Amides* (Ed.: J. Zabicky), Interscience, New York, 1970, p. 1-72.) Consequently, the reduction of amides typically requires stoichiometric amounts of active Al—H, B—H, or Si—H reducing agents that often cause reductive cleavage of the C═O bond (J. Seyden-Penne, *Reductions by the Alumino and Borohydrides in Organic Synthesis*, 2nd Ed., Wiley-VCH, New York, 1997. G. W. Gribble, *Chem. Soc. Rev.* 1998, 27, 395; G. Pelletier, W. S. Bechara, A. B. Charette, *J. Am. Chem. Soc.* 2010, 132, 12817; S. Das, D. Addis, S. Thou, K. Junge, M. Beller, *J. Am. Chem. Soc.* 2010, 132, 1770; Y. Sunada, H. Kawakami, T. Imaoka, Y. Matoyama, H. Nagashima. *Angew. Chem. Int. Ed.* 2009, 48, 9511, C. Cheng, M. Brookhart, *J. Am. Chem. Soc.* 2012, DOI: 10.1021/ja304547s)

Numerous heterogeneous catalysts have been developed to hydrogenate amides. These include copper-chromite systems that give mixtures of amine products under 350 atm $H_2$, 250-400° C. (B. Wojcik, H. Adkins, *J. Am. Chem. Soc.* 1934, 56, 2419; R. M. King, U.S. Pat. No. 4,448,998, May 15, 1984.) Co-catalysts of Rh or Ru with Re, W, or Mo hydrogenate amides either via reductive cleavage of the C═O bond (100 atm $H_2$, 160-180° C.), (C. Hirosawa, N. Wakasa, T. Fuchikami, *Tetrahedron Lett.* 1996, 37, 6749) or with selectivity for hydrogenating primary amides to the corresponding primary amines (20-100 atm $H_2$, 130-160° C.). (G. Beamson, A. J. Papworth, C. Philipps, A. M. Smith, R. J. Whyman, *J. Catal.* 2011, 278, 228; *Adv. Synth. Catal.* 2010, 352, 869; *J. Catal.* 2010, 296, 93.)

There are a handful of homogeneous systems that catalyze the hydrogenation of amides or amide derivatives. The first is a Ru-triphos system (triphos=1,1,1-tris(diphenyl-phosphinomethyl)ethane) that hydrogenates primary amides with a preference for reductive cleavage of the C═O bond in the presence of $NH_3$ (40 atm $H_2$, 140-164° C., 14 h). (M. Kilner, D. V. Tyers, S. P. Crabtree, M. A. Wood, PCT Int. Pat. Appl. WO 03/093208 A1, Nov. 13, 2003; A. A. N. Magro, G. R. Eastham, D. Cole-Hamilton, *Chem. Commun.* 2007, 3154; US Pat. 2010/0010261 A1, Jan. 14, 2010.)

Beginning in 2006, Ikariya et al. reported dihydrogenations of cyclic imides, (M. Ito, A. Sakaguchi, C. Kobayashi, T. Ikariya, *J. Am. Chem. Soc.* 2007, 129, 290; M. Ito, C. Kobayashi, A. Himizu, T. Ikariya, *J. Am. Chem. Soc.* 2010, 132, 11414) N-acyl carbamates, N-sulfonyl-lactams, N-acylsulfonamides, (M. Ito, L. W. Koo, A. Himizu, C. Kobayashi, A. Sakaguchi, T. Ikariya. *Angew. Chem. Int. Ed.* 2009, 48, 1324) N-phenyl lactams and benzamides (T. Ikariya, M. Ito, T. Ootsuka, PCT Int. Pat. Appl. WO 2010/073974 A1, Jul. 1, 2010; M. Ito, T. Ootsuka, R. Watari, A. Shiibashi, A. Himizu, T. Ikariya, *J. Am. Chem. Soc.* 2011, 133, 4240.) with reductive cleavage of the C—N bond catalyzed by [Cp*RuCl(PN)] [Cp*=$\eta^5$-$C_5(CH_3)_5$; e.g. PN=$Ph_2P(CH_2)_2NH_2$] or [Cp*RuCl(LN)] e.g. (LN=2-$C_5H_4NCH_2NH_2$) (tBuOH or 2-PrOH, 80-100° C., 30-50 atm, KOtBu 1-2.5 equiv, 2-72 h).

Recently reported is the enantioselective monohydrogenation of meso-cyclic imides to give hydroxy lactams with trans-[Ru(H)$_2$(BINAP)(dpen)] (BINAP=2,2'-bis(diphenylphosphino)-1,1'-binaphthyl) and dpen=1,2-diphenylethylenediamine) and related complexes in THF at low temperatures (0.1 mol % Ru, 0° C., 50 atm $H_2$, 9 mol % tBuOK, 17-57 h). (S. Takebayashi, J. M. John, S. H. Bergens, *J. Am. Chem. Soc.* 2010, 132, 12832; S. Takebayashi, S. H. Bergens, PCT Int. Pat. Appl. WO 2010/145024 A1, Jun. 17, 2010.) Catalysts such as trans-[Ru(H)$_2$(BINAP)(dpen)] have been shown to be active towards amide hydrogenation, however they can decompose at the higher temperature required for this transformation.

The most active system to date is Milstein's dearomatized, bipyridyl-based PNN Ru complex (PNN=(2-(di-tert-butylphosphinomethyl)-6-(diethylaminomethyl)pyridine) that hydrogenates a variety of secondary amides, and tertiary amides with ether groups to give the alcohol and amine products with 1 mol % Ru in THF (base free, 110° C., 10 atm $H_2$, 48 h). (E. Balaraman, B. Gnanaprakasam, L. J. W. Shimon, D. Milstein, *J. Am. Chem. Soc.* 2010, 132, 16756.)

Recently reported is the low-T preparation and study of the Noyori ketone hydrogenation catalyst trans-[Ru((R)-BINAP)(H)$_2$((R,R)-dpen)] (1). (R. J. Hamilton, C. G. Leong, G. Bigam, M. Miskolzie, S. H. Bergens, *J. Am. Chem. Soc.* 2005, 127, 4152; R. J. Hamilton, S. H. Bergens, *J. Am. Chem. Soc.* 2006, 128, 13700; *J. Am. Chem. Soc.* 2008, 130, 11979.)

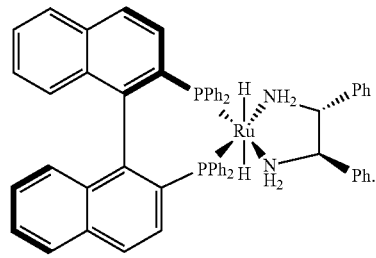

(1)

Compound (1) is remarkably active towards carbonyl reduction. For example, (1) adds acetophenone on mixing and adds gamma-butyrolactone within minutes at −80° C. to form the alkoxide, trans-[Ru((R)-BINAP)(H)(OCH(CH$_3$)(Ph))((R,R)-dpen)] and the corresponding Ru-hemiacetaloxide of gamma-butyrolactone. (1) Also catalyzes the hydrogenation of ethyl hexanoate under 4 atm $H_2$ below 0° C. (S. Takebayashi, S. H. Bergens, *Organometallics*. 2009, 28, 2349.) and the monohydrogenation of meso-cyclic imides at 0° C. (S. Takebayashi, J. M. John, S. H. Bergens, *J. Am. Chem. Soc.* 2010, 132, 12832; S. Takebayashi, S. H. Bergens, PCT Int. Pat. Appl. WO 2010/145024 A1, Jun. 17, 2010.) However, compound (1) has not be used in amide hydrogenation reactions.

It is, therefore, desirable to provide processes and catalysts for the hydrogenation of amides.

This background information is provided for the purpose of making known information believed by the applicant to be of possible relevance to the present invention. No admission is necessarily intended, nor should be construed, that any of the preceding information constitutes prior art against the present invention.

SUMMARY

An object of the present invention is to provide a process for the reduction of one or more amide moieties in a compound comprising contacting the compound with hydrogen gas and a transition metal catalyst in the presence or absence of a base under conditions for the reduction an amide bond.

In accordance with one aspect, there is provided a process for the reduction an amide bond in a substrate comprising contacting the substrate with hydrogen gas and a transition metal catalyst complex under conditions suitable to cleave the amide bond, wherein said process is performed in the presence of a base or in the absence of base and wherein, when said process is performed in the presence of a base and the transition metal catalyst complex is present at an amount of 1 mol % or more, the process is performed (i) at a temperature of 100° C. or less; (ii) using hydrogen gas at a pressure less than 10 atm; or (iii) at a temperature of 100° C. or less and using hydrogen gas at a pressure less than 10 atm.

In accordance with one embodiment, the transition metal is Ru, Fe, Rh, Ir, Pd, Cu, Co, Pt, Ti, Zr, Os or Hf. In one specific embodiment, the transition metal is Ru.

In accordance with another embodiment, the transition metal catalyst complex comprises the transition metal coordinated to one to four ligands selected from:
(i) a bidentate diphosphine (P—P) ligand;
(ii) a bidentate diamino (N—N) ligand;
(iii) a bidentate aminophosphine (P—N) ligand;
(iv) a tridentate diaminophosphine (P—N—N) ligand;
(v) a tridentate aminodiphosphine (P—N—P) ligand;
(vi) a tetradentate diaminodiphosphine (P—N—N—P) ligand;
(vii) a monodentate phoshine (P) ligand; and
(viii) a monodentate amine (N) ligand;
and optionally one or more ligands selected from:
a hydride ligand;
a neutral monodentate ligand; and
an anionic monodentate ligand,
wherein if the transition metal catalyst complex is cationic, the transition metal catalyst complex further comprises one or more suitable counteranions.

In accordance with another embodiment, the bidentate diphosphine (P—P) ligand is

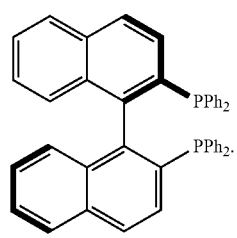

In accordance with another embodiment, the bidentate diamino (N—N) ligand is

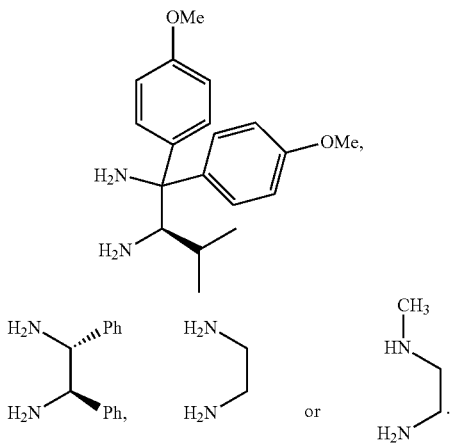

In accordance with another embodiment, the bidentate aminophosphine (P—N) ligand has the Formula (X)

$$PR^{36}R^{36}CHR^{35}CHR^{35}NH_2 \quad (X)$$

wherein each $R^{35}$ is independently H, $(C_{1-10})$alkyl, $(C_{1-10})$ alkyl fluoro-substituted $(C_{1-4})$-alkyl, halo, $(C_{1-10})$cycloalkyl, fluoro-substituted $(C_{1-10})$cycloalkyl, $(C_{1-10})$-alkoxy, fluoro-substituted $(C_{1-10})$-alkoxy, unsubstituted and substituted phenyl and substituted and unsubstituted naphthyl, or adjacent substituents are joined together to form, including the carbon atoms to which they are attached, one or more unsubstituted or substituted phenylene, cyclohexylene, naphthylene, pyridylene or ferrocenylene groups, and each $R^{36}$ is independently $(C_{4-10})$ alkyl, $(C_{4-10})$ cycloalkyl, or phenyl, each of which may be optionally substituted.

In accordance with another embodiment, the transition metal catalyst is:

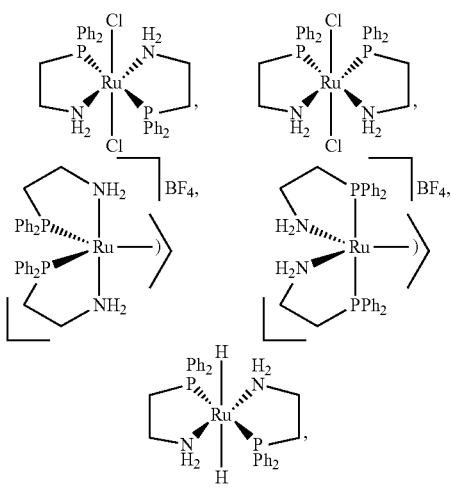

trans-[Ru((R)-BINAP)(H)$_2$((R,R)-dpen)], [Ru(Cl)$_2$(Ph$_2$P (CH$_2$)$_2$NH$_2$)$_2$], [Ru(COD)(Anthracene)]BF$_4$, cis-[Ru (CH$_3$CN)$_2$($\eta^3$-C$_3$H$_5$)(COD)]BF$_4$, [Ru(Ph$_2$PCH$_2$CH$_2$NH$_2$)$_2$ ($\eta^3$-C$_3$H$_5$)]BF$_4$, trans-[Ru(H)$_2$(Ph$_2$P(CH$_2$)$_2$NH$_2$)$_2$], [Ru(H) (Ph$_2$P(CH$_2$)$_2$NH$_2$) (Ph$_2$P(CH$_2$)$_2$NH)], [Ru(Cl)$_2$ (Cy$_2$PCH$_2$CH$_2$NH$_2$)$_2$] (Cy=cyclohexyl), or an isomer thereof.

In accordance with another embodiment, the transition metal catalyst complex is chiral.

In accordance with another embodiment, the substrate is chiral.

In accordance with another embodiment, the process of the amide bond cleavage of the substrate produces an alcohol and an amine.

In accordance with another embodiment, the process of the amide bond cleavage of the substrate generates products that are enantiomerically enriched.

In accordance with another embodiment, the process of the amide bond cleavage of the substrate generates a chiral product.

In accordance with another embodiment, the process is performed in a solvent selected from tetrahydrofuran (THF), diethyl ether, chlorinated solvents, toluene and mixtures thereof.

In accordance with another embodiment, the hydrogen gas is used at a pressure in the range of from about 1 atm to about 100 atm.

In accordance with another embodiment, the hydrogen gas is used at a pressure less than about 50 atm.

In accordance with another embodiment, the process is performed in the presence of a base and the transition metal catalyst complex is present at an amount of 1 mol % or less.

In accordance with another embodiment, the transition metal catalyst complex is present at an amount of about 0.5 mol % or less, or about 0.1 mol % or less or from about 0.1 mol % to about 0.01 mol %.

In accordance with another embodiment, the process is performed at a temperature of 100° C. or less and the hydrogen gas is used at a pressure of 50 atm or less.

In accordance with another embodiment, the process is performed in the presence of a base, the transition metal catalyst is present at an amount less than about 10 mol %, the hydrogen gas is used at a pressure of about 4 atm or less and the process is carried out at a temperature of 0° C. or higher.

In accordance with another embodiment, the process is carried out at a temperature of from about 22° C. to about 0° C.

In accordance with another embodiment, the base is an organic non-coordinating base, a carbonate salt, a carboxylate salt, an alcoholate salt, a hydroxide salt or a silazine salt. In one specific embodiment, the base is tBuOK or [(CH$_3$)$_3$Si]$_2$NK.

In accordance with another embodiment, the process is performed in the absence of base and the hydrogen gas is used at a pressure less than about 10 atm, or less than about 5 atm.

In accordance with another embodiment, the process is performed at a temperature of from about −50° C. to about 150° C.

In accordance with another embodiment,

In accordance with another aspect, there is provided a transition metal catalyst complex selected from:

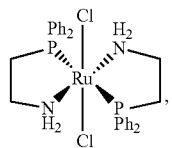
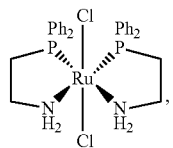

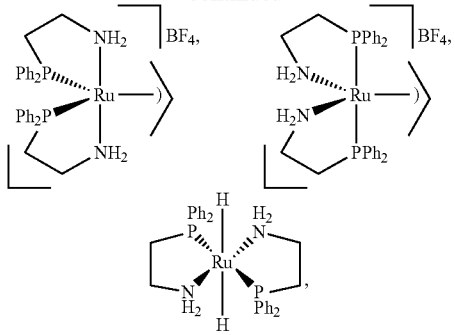

trans-[Ru((R)-BINAP)(H)$_2$((R,R)-dpen)], [Ru(Cl)$_2$(Ph$_2$P(CH$_2$)$_2$NH$_2$)$_2$], [Ru(COD)(Anthracene)]BF$_4$, cis-[Ru(CH$_3$CN)$_2$(η$^3$-C$_3$H$_5$)(COD)]BF$_4$, [Ru(Ph$_2$PCH$_2$CH$_2$NH$_2$)$_2$(η$^3$-C$_3$H$_5$]BF$_4$, trans-[Ru(H)$_2$(Ph$_2$P(CH$_2$)$_2$NH$_2$)$_2$], [Ru(H)(Ph$_2$P(CH$_2$)$_2$NH$_2$)(Ph$_2$P(CH$_2$)$_2$NH)], [Ru(Cl)$_2$(Cy$_2$PCH$_2$CH$_2$NH$_2$)$_2$] (Cy=cyclohexyl), and isomers thereof.

In accordance with another aspect, there is provided a process for the reduction an amide bond in a substrate comprising contacting the substrate with hydrogen gas and a transition metal catalyst complex under conditions suitable to cleave the amide bond, wherein the transition metal catalyst complex comprises at least one bidentate aminophosphine (P—N) ligand.

In accordance with one embodiment, the bidentate aminophosphine (P—N) ligand has the Formula (X)

$$PR^{36}R^{36}CHR^{35}CHR^{35}NH_2 \qquad (X)$$

wherein each $R^{35}$ is independently H, (C$_{1-10}$)alkyl, (C$_{1-10}$) alkyl fluoro-substituted (C$_{1-4}$)-alkyl, halo, (C$_{1-10}$)cycloalkyl, fluoro-substituted (C$_{1-10}$)cycloalkyl, (C$_{1-10}$)-alkoxy, fluoro-substituted (C$_{1-10}$)-alkoxy, unsubstituted and substituted phenyl and substituted and unsubstituted naphthyl, or adjacent substituents are joined together to form, including the carbon atoms to which they are attached, one or more unsubstituted or substituted phenylene, cyclohexylene, naphthylene, pyridylene or ferrocenylene groups, and each $R^{36}$ is independently (C$_{4-10}$) alkyl, (C$_{4-10}$) cycloalkyl, or phenyl, each of which may be optionally substituted.

In accordance with another embodiment, the transition metal catalyst complex is

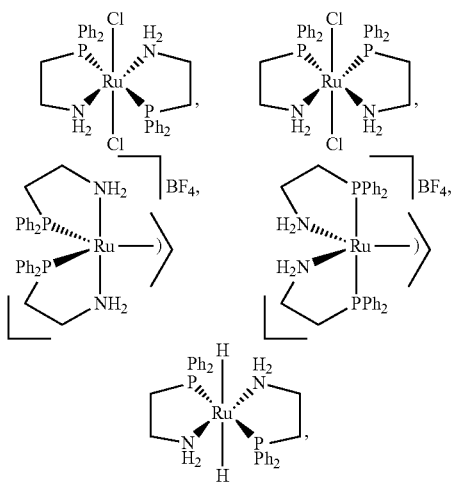

[Ru(Cl)$_2$(Ph$_2$P(CH$_2$)$_2$NH$_2$)$_2$], [Ru(Ph$_2$PCH$_2$CH$_2$NH$_2$)$_2$($\eta^3$-C$_3$H$_5$)]BF$_4$, trans-[Ru(H)$_2$(Ph$_2$P(CH$_2$)$_2$NH$_2$)$_2$], [Ru(H)(Ph$_2$P(CH$_2$)$_2$NH$_2$) (Ph$_2$P(CH$_2$)$_2$NH)], [Ru(Cl)$_2$(Cy$_2$PCH$_2$CH$_2$NH$_2$)$_2$] (Cy=cyclohexyl), or an isomer thereof.

In accordance with another embodiment, the substrate is chiral.

In accordance with another embodiment, the process of the amide bond cleavage of the substrate produces an alcohol and an amine.

In accordance with another embodiment, the process of the amide bond cleavage of the substrate generates products that are enantiomerically enriched.

In accordance with another embodiment, the process of the amide bond cleavage of the substrate generates a chiral product.

In accordance with another embodiment, the process is performed in a solvent selected from tetrahydrofuran (THF), diethyl ether, chlorinated solvents, toluene and mixtures thereof.

In accordance with another embodiment, the hydrogen gas is used at a pressure in the range of from about 1 atm to about 100 atm. In accordance with another embodiment, the hydrogen gas is used at a pressure less than about 50 atm.

In accordance with another embodiment, the process is performed in the presence of a base and the transition metal catalyst complex is present at an amount of 1 mol % or less.

In accordance with another embodiment, the process is performed in the presence of a base, the transition metal catalyst is present at an amount less than about 10 mol %, the hydrogen gas is used at a pressure of about 4 atm or less and the process is carried out at a temperature of 0° C. or higher.

In accordance with another embodiment, the base is an organic non-coordinating base, a carbonate salt, a carboxylate salt, an alcoholate salt, a hydroxide salt or a silazine salt.

In accordance with another embodiment, the base is tBuOK or [(CH$_3$)$_3$Si]$_2$NK.

In accordance with another embodiment, the transition metal catalyst complex is present at an amount of about 0.5 mol % or less, or about 0.1 mol % or less or from about 0.1 mol % to about 0.01 mol %.

In accordance with another embodiment, the process is performed at a temperature of 100° C. or less and the hydrogen gas is used at a pressure of 50 atm or less. In accordance with another embodiment, In accordance with another embodiment, the process is performed in the absence of base and the hydrogen gas is used at a pressure less than about 10 atm, or less than about 5 atm.

In accordance with another embodiment, the process is performed at a temperature of from about −50° C. to about 150° C.

In accordance with another aspect, there is provided a process for the reduction an amide bond in a substrate comprising contacting the substrate with hydrogen gas and a transition metal catalyst complex under conditions suitable to cleave the amide bond, wherein said process is performed in the presence of a base or in the absence of base, and wherein said transition metal catalyst complex can catalyze the cleavage of the amide bond in the presence of base when the transition metal catalyst is present at an amount of less than 1 mol % or when the transition metal catalyst is present at an amount of 1 mol % or more and the process is performed (i) at a temperature of 100° C. or less; (ii) using hydrogen gas at a pressure of less than 10 atm; or (iii) at a temperature of 100° C. or less and using hydrogen gas at a pressure less than 10 atm.

BRIEF DESCRIPTION OF THE FIGURES

For a better understanding of the present invention, as well as other aspects and further features thereof, reference is made to the following description which is to be used in conjunction with the accompanying drawings, where.

DETAILED DESCRIPTION

Definitions

Figure 1:
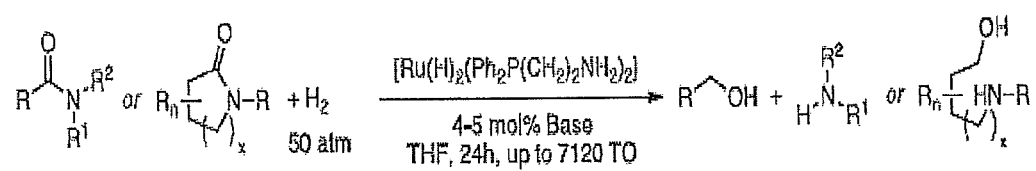
FIG. 1 depicts the reaction between 2 equivalents of Ph$_2$P(CH$_2$)$_2$NH$_2$ and cis-[Ru(CH$_3$CN)$_2$($\eta^3$-C$_3$H$_5$)(COD)]BF$_4$ (COD=1,5-cyclooctadiene) to form a highly active catalyst precursor for the selective hydrogenation of amides.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

As used herein, "alkyl" refers to a linear, branched or cyclic, saturated hydrocarbon group which can be unsubstituted or optionally substituted with one or more substituent. Examples of saturated straight or branched chain alkyl groups include, but are not limited to, methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl and 2-ethyl-1-butyl, 1-heptyl and 1-octyl. As used herein the term "alkyl" encompasses cyclic alkyls, or cycloalkyl groups. The term "cycloalkyl" as used herein refers to a non-aromatic, saturated monocyclic, bicyclic or tricyclic hydrocarbon ring system containing at least 3 carbon atoms. Examples of $C_3$-$C_{12}$ cycloalkyl groups include, but are not limited to, cyclopropyl, cyclobutyl, cyclopentyl, cyclohexyl, cycloheptyl, cyclooctyl, norbornyl, adamantyl, bicyclo[2.2.2]oct-2-enyl, and bicyclo[2.2.2]octyl.

The term "$(C_{1-n})$-alkyl" as used herein refers to straight and/or branched chain, saturated alkyl radicals containing from one to "n" carbon atoms and includes (depending on the identity of n) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable n is an integer representing the largest number of carbon atoms in the alkyl radical.

The term "$(C_{3-n})$-cycloalkyl" as used herein refers to a monocyclic or polycyclic saturated carbocyclic group containing from three to n carbon atoms and includes (depending on the identity of n) cyclopropyl, cyclobutyl, cyclopentyl, cyclodecyl, bicyclo[2.2.2]octane, bicyclo[2.2.1]heptane, bicyclo[3.1.1]heptane and the like, where the variable n is an integer representing the largest number of carbon atoms in the cycloalkyl radical.

As used herein, the term "alkenyl" refers to a straight, branched or cyclic hydrocarbon group containing at least one double bond which can be unsubstituted or optionally substituted with one or more substituents.

The term "$(C_{2-n})$-alkenyl" as used herein refers to straight and/or branched chain, unsaturated alkyl radicals containing from two to n carbon atoms and one or more, suitably one to three, double bonds, and includes (depending on the identity of n) vinyl, allyl, 2-methylprop-1-enyl, but-1-enyl, but-2-enyl, but-3-enyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like, where the variable n is an integer representing the largest number of carbon atoms in the alkenyl radical.

The term "$(C_{3-n})$-cycloalkenyl" as used herein refers to a monocyclic or polycyclic carbocyclic group containing from three to n carbon atoms (depending on the identity of n) and one or more, suitably one or two, double bonds and includes cyclopropenyl, cyclobutenyl, cyclopentenyl, cyclodecenyl, bicyclo[2.2.2]oct-2-ene, bicyclo[2.2.1]hept-2-ene, bicyclo[3.1.1]hept-2-ene and the like, where the variable n is an integer representing the largest number of carbon atoms in the cycloalkenyl radical.

As used herein, "alkynyl" refers to an unsaturated, straight or branched chain hydrocarbon group containing at least one triple bond which can be unsubstituted or optionally substituted with one or more substituents.

The term "$(C_{2-n})$-alkynyl" as used herein refers to straight and/or branched chain, unsaturated alkyl groups containing from one to n carbon atoms and one or more, suitably one to three, triple bonds, and includes (depending on the identity of n) ethynyl, 1-propynyl, 2-propynyl, 2-methylprop-1-ynyl, 1-butynyl, 2-butynyl, 3-butynyl, 1,3-butadiynyl, 3-methylbut-1-ynyl, 4-methylbut-ynyl, 4-methylbut-2-ynyl, 2-methylbut-1-ynyl, 1-pentynyl, 2-pentynyl, 3-pentynyl, 4-pentynyl, 1,3-pentadiynyl, 1,4-pentadiynyl, 3-methylpent-1-ynyl, 4-methylpent-2-ynyl, 4-methylpent-2-ynyl, 1-hexynyl and the like, where the variable n is an integer representing the largest number of carbon atoms in the alkynyl radical.

The term "$(C_{3-n})$-cycloalkynyl" as used herein refers to a monocyclic or polycyclic carbocyclic group containing from three to n carbon atoms (depending on the identity of n) and one or more, suitably one or two, double bonds and includes cyclopropenyl, cyclobutynyl, cyclopentynyl, cyclohexynyl, cyclodecynyl, bicyclo[2.2.2]oct-2-yne, bicyclo[2.2.1]hept-2-yne, bicyclo[3.1.1]hept-2-yne and the like, where the variable n is an integer representing the largest number of carbon atoms in the cycloalkynyl radical.

As used herein, "aryl" refers to hydrocarbons derived from benzene or a benzene derivative that are unsaturated aromatic carbocyclic groups of from 6 to 100 carbon atoms, or from which may or may not be a fused ring system, in some embodiments 6 to 50, in other embodiments 6 to 25, and in still other embodiments 6 to 15. The aryls may have a single or multiple rings. The term "aryl" as used herein also includes substituted aryls. Examples include, but are not limited to phenyl, naphthyl, xylene, phenylethane, substituted phenyl, substituted naphthyl, substituted xylene, substituted phenylethane and the like. As used herein, "heteroaryl" refers to an aryl that includes from 1 to 10, in other embodiments 1 to 4, heteroatoms such as but not limited to oxygen, nitrogen and sulfur. The heteroaryl may be substituted or unsubstituted.

The term "$(C_{6-n})$-aryl" as used herein refers to a monocyclic, bicyclic or tricyclic carbocyclic ring system containing from 6 to n carbon atoms and optionally a metal and includes, depending on the identity of n, phenyl, naphthyl, anthracenyl, 1,2-dihydronaphthyl, 1,2,3,4-tetrahydronaphthyl, fluorenyl, indanyl, indenyl, ferrocenyl, and the like, where the variable n is an integer representing the largest number of carbon atoms in the aryl radical.

As used herein, a "heteroatom" refers to an atom that is not carbon or hydrogen, such as nitrogen, oxygen, sulfur, phosphorus, chlorine, bromine, and iodine.

As used herein, the terms "heterocycle" and "heteroaryl" refer to an aromatic or nonaromatic monocyclic or bicyclic ring of carbon atoms and from 1 to 5 heteroatoms selected from oxygen, nitrogen and sulfur, and which can be substituted or unsubstituted. Included within the term "heterocycle" are heteroaryls, as defined above. Examples of 3- to 9-membered heterocycles include, but are not limited to, aziridinyl, oxiranyl, thiiranyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, triazinyl, tetrazinyl, imidazolyl, benzimidazolyl, tetrazolyl, indolyl, isoquinolinyl, quinolinyl, quinazolinyl, pyrrolidinyl, purinyl, isoxazolyl, benzisoxazolyl, furanyl, furazanyl, pyridinyl, oxazolyl, benzoxazolyl, thiazolyl, benzthiazolyl, thiophenyl, pyrazolyl, triazolyl, benzodiazolyl, benzotriazolyl, pyrimidinyl, isoindolyl and indazolyl.

As used herein, "substituted" refers to the structure having one or more substituents. A substituent is an atom or group of bonded atoms that can be considered to have replaced one or more hydrogen atoms attached to a parent molecular entity. Examples of substituents include aliphatic groups, halogen, arylcarbonyloxy, alkoxycarbonyloxy, aryloxycarbonyloxy, alkoxycarbonyl, aminocarbonyl, alkylthiocarbonyl, alkoxyl, phosphate ester, phosphonato, phosphinato, cyano, tertiary amino, tertiary acylamino, tertiary amide, imino, alkylthio, arylthio, sulfonato, sulfamoyl, tertiary sulfonamido, nitrile, trifluoromethyl, heterocyclyl, aromatic, and heteroaromatic moieties, ether, ester, boron-containing moieties, tertiary phosphines, and silicon-containing moieties.

As used herein, "halogen" and "halo" refers to F, Cl, Br or I.

The term "fluoro-substituted" with respect to any specified group as used herein indicates that one or more, including all, of the hydrogen atoms in the group have been replaced with fluorine, and includes trifluoromethyl, pentafluoroethyl, fluoromethyl and the like.

The suffix "ene" added on to any of the above groups means that the group is divalent, i.e. inserted between two other groups.

The term "ring system" as used herein refers to a carbon-containing ring system, that includes monocycles, fused bicyclic and polycyclic rings, bridged rings and metallocenes. Where specified, the carbons in the rings may be substituted or replaced with heteroatoms. The term "unsaturated" with respect to ring systems includes aromatic and nonaromatic rings.

The terms "transition metal" and "suitable transition metal" as used herein refer to any transition metal that can be used to form a transition metal catalyst useful in the presently described process in the reduction of amides. These include, but are not limited to, Fe, Ru, Rh, Ir, Pd, Cu, Co, Pt, Ti, Zr, Os and Hf.

The term "transition metal catalyst complex" as used herein refers to a complex comprising a transition metal catalyst, optionally also comprising one or more additional counteranion.

As used herein, the term "transition metal catalyst" refers to the element of the transition metal catalyst complex that comprises the transition metal and its associated coordinated ligands. The transition metal catalyst is capable of binding hydride to form a transition metal hydride, which is the active catalyst. The active catalyst, which is capable of reducing an amide moiety, has at least one hydride ligand. It will be understood that more than four hydrogen atoms or hydrides can be coordinated to the transition metal to form a transition metal hydride that can act as a catalyst for the processes of the present disclosure.

As used herein, the terms "suitable counteranion" and "counteranion" refer to a negatively charged ion that is optionally a part of the transition metal catalyst complex to charge balance a positively charged transition metal catalyst species. The counteranion is present in the transition metal catalyst complex when the transition metal catalyst is cationic, such that the total charge of transition metal catalyst complex is zero. It is understood that the counteranion is not reactive with the transition metal catalyst. Some examples of counteranions include, but are not limited to, OTf$^-$, BF$_4^-$ and PF$_6^-$.

As used herein, the term "ligand" refers to the monodentate, bidentate, tridentate or tetradentate compound(s) which coordinate to the transition metal to form the transition metal catalyst. The presently described ligands may be chiral or achiral. In the case where the ligand is chiral, it is understood that the chiral atom may be present anywhere in the ligand molecule.

The term "neutral monodentate ligand" as used herein refers to any neutral ligand which donates a single pair electrons and coordinates to the transition metal through a dative covalent bond. Some examples of neutral monodentate ligands include, but are not limited to, water, acetonitrile, DMF, ammonia, carbon monoxide, pyridine, tetrahydrofuran (THF), t-BuCN and t-BuNC.

The term "anionic monodentate ligand" as used herein refers to any anionic ligand which donates a single pair electrons and coordinates to the transition metal. Examples of anionic monodentate ligands include, but are not limited to, halogens such as fluoro, chloro, bromo or iodo, (C$_{1-6}$)-alkoxy, hydroxy, thiocyanate, cyano, carboxylate, sulfonates and nitrates.

The terms "(P—P) ligand", "(N—N) ligand", "(P—N) ligand", "(P—N—N) ligand", "(P—N—P) ligand", "(P—N—N—P) ligand", "(P) ligand" and "(N) ligand" refer to ligands that can coordinate to the transition metal, wherein the capital letters in the brackets designate the atoms in each ligand, in series, that coordinate to the transition metal. For example, in the case of a (P—N—N) ligand, the ligand comprises a phosphorus atom, a first nitrogen atom and a second nitrogen atom connected in series with linker groups therebetween, wherein the phosphorus atom, first nitrogen atom and second nitrogen atom each form a dative covalent bond with the transition metal.

As used herein, the terms "amide" and "amide bond" have their commonly understood meaning and refer to the bivalent functional group —N—CO—, or

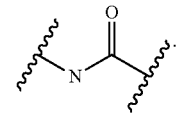

As used herein, the term "cleave an amide bond" means that the C—N bond between the nitrogen and the carbonyl carbon in the amide bond is broken during the process of the reaction. Under the presently described process, the nitrogen and carbonyl group can be hydrogenated to give, respectively, an amine and an alcohol. The skilled worker will also appreciate that if the amide can also form the amino-alcohol and/or amine as it goes through the aldehyde or hemiaminal. Incomplete reductions are also possible, resulting in aldehydes, for example, which can undergo in situ reaction condensation reactions. The amide bond may be part of a linear or cyclic structure such that the reaction can result in a single compound having both an amine and an alcohol, or two separate compounds, one of which containing the amine and the other one having the alcohol.

The terms "reduction" and "hydrogenation" as used herein refer to the cleavage reaction of the amide bond.

As used herein, the term "dative covalent bond" refers to a coordinate bond wherein the shared pair of electrons that form the bond come from the same atom. In the present disclosure, the dative covalent bond occurs between the transition metal, e.g. ruthenium, and the coordinating atom.

As used herein, a "coordinating atom" refers to an atom having a lone pair of electrons capable of coordinating, or forming a covalent dative bond with the transition metal.

As used herein the term "base free" refers to a reaction that proceeds in the absence of base. Specifically, when the hydrogenation reaction is carried out in base, it is understood that the base participates in the reaction. The Applicant notes that a person of skill in the art would recognise that though $BH_4^-$ is a weak base, it is not considered to be a strong enough base to assist in the hydrogenation reaction.

Described herein are processes and catalysts for the hydrogenation of amides. Specifically, there is provided a process for the reduction of one or more amide moieties in a compound comprising contacting the compound with hydrogen gas and a catalyst comprising a transition metal hydride in the presence or absence of a base under conditions for the reduction of the one or more amide moieties to form a compound comprising amino alcohols and/or alcohols and amines.

The presently described processes are characterized by the high activity of the catalysts in comparison to catalysts used in the past. Furthermore, the present processes can be performed at relatively low temperature and pressure, with relatively low catalyst loading, and optionally, in the absence of a base.

Catalysts

The transition metal catalyst can be a complex comprising a suitable transition metal, and coordinated thereto, one to four ligands selected from: (i) a bidentate diphosphine (P—P) ligand, (ii) a bidentate diamino (N—N) ligand, (iii) a bidentate aminophosphine (P—N) ligand, (iv) a tridentate diaminophosphine (P—N—N) ligand, (v) a tridentate aminodiphosphine (P—N—P) ligand, (vi) a tetradentate diaminodiphosphine (P—N—NP) ligand, (vii) a monodentate phoshine (P) ligand, and (viii) a monodentate amine ligand (N); one to three hydride ligands; zero to two neutral monodentate ligands; and zero to two anionic monodentate ligands, the complex being neutral or cationic, and if the complex is cationic, the complex further comprises one or more suitable counteranions.

The transition metal can be Ru, Fe, Rh, Ir, Pd, Cu, Co, Pt, Ti, Zr, Os or Hf. In some examples the transition metal is Ru, Fe or Rh. In a specific example the transition metal is Ru.

In some examples, the transition metal catalyst is selected from:

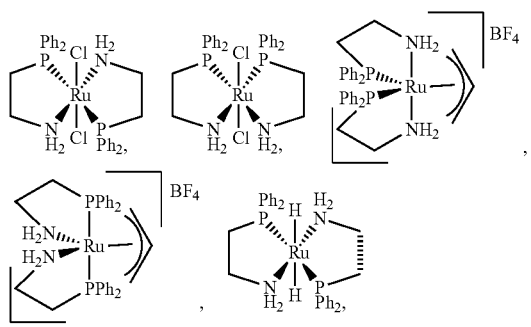

trans-[Ru((R)-BINAP)(H)$_2$((R,R)-dpen)], [Ru(Cl)$_2$(Ph$_2$P (CH$_2$)$_2$NH$_2$)$_2$], [Ru(COD)(Anthracene)]BF$_4$, cis-[Ru (CH$_3$CN)$_2$($\eta^3$-C$_3$H$_5$)(COD)]BF$_4$, [Ru(Ph$_2$PCH$_2$CH$_2$NH$_2$)$_2$ ($\eta^3$-C$_3$H$_5$)]BF$_4$, trans-[Ru(H)$_2$(Ph$_2$P(CH$_2$)$_2$NH$_2$)$_2$], [Ru(H) (Ph$_2$P(CH$_2$)$_2$NH$_2$)(Ph$_2$P(CH$_2$)$_2$NH)], [Ru(Cl)$_2$ (Cy$_2$PCH$_2$CH$_2$NH$_2$)$_2$] (Cy=cyclohexyl), or an isomer thereof.

In some examples, the catalyst complex includes a counteranion such as, for example, OTf$^-$ or BF$_4^-$ or PF$_6^-$.

In one exemplary transition metal catalyst, a reaction between 2 equivalents of Ph$_2$P(CH$_2$)$_2$NH$_2$ and cis-[Ru (CH$_3$CN)$_2$($\eta^3$-C$_3$H$_5$)(COD)]BF$_4$ (COD=1,5-cyclooctadiene) forms a the transition metal catalyst [Ru($\eta^3$-C$_3$H$_5$) (Ph$_2$P(CH$_2$)$_2$NH$_2$)$_2$]BF$_4$ (5), for the selective hydrogenation of amides. The dichloride analog [Ru(Cl)$_2$(Ph$_2$P(CH$_2$)$_2$ NH$_2$)$_2$] (2) can also function as a catalyst precursor for this transformation. In the presence of molecular hydrogen in THF, these catalysts (5) and (2) can pick up hydrogen to generate the active transition metal catalyst. One example of an active transition metal catalyst resulting from these catalysts picking up hydride is [Ru(H)$_2$(Ph$_2$PCH$_2$CH$_2$ NH$_2$)$_2$].

In another embodiment, there is provided a transition metal catalyst selected from

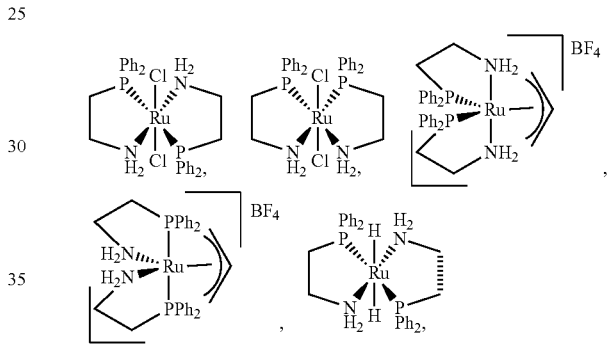

trans-[Ru((R)-BINAP)(H)$_2$((R,R)-dpen)], [Ru(Cl)$_2$(Ph$_2$P (CH$_2$)$_2$NH$_2$)$_2$], [Ru(COD)(Anthracene)]BF$_4$, cis-[Ru (CH$_3$CN)$_2$($\eta^3$-C$_3$H$_5$)(COD)]BF$_4$, [Ru(Ph$_2$PCH$_2$CH$_2$NH$_2$)$_2$ ($\eta^3$-C$_3$H$_5$)]BF$_4$, trans-[Ru(H)$_2$(Ph$_2$P(CH$_2$)$_2$NH$_2$)$_2$], [Ru(H) (Ph$_2$P(CH$_2$)$_2$NH$_2$)—(Ph$_2$P(CH$_2$)$_2$NH)] or an isomer thereof.

While not wishing to be bound by theory, it is hypothesized that tethering the amine and phosphine groups can increase the thermal stability of the catalyst by preventing dissociative loss of the ligand(s) at high temperature. It has been shown that these types of transition metal catalysts having tethered amine and phosphine groups can have activity for the hydrogenation of amides.

The reaction between 2 equivalents of Ph$_2$P(CH$_2$)$_2$NH$_2$ 3 and the Ru precursor cis-[Ru(CH$_3$CN)$_2$($\eta^3$-C$_3$H$_5$)(COD)] BF$_4$ (4) (wherein COD is 1,5-cyclooctadiene) in THF at 60° C. forms isomers of the π-allyl complex (5) in near-quantitative solution yield by displacement of the COD and MeCN ligands (See Scheme 1, below).

Scheme 1: Formation of catalyst (5)

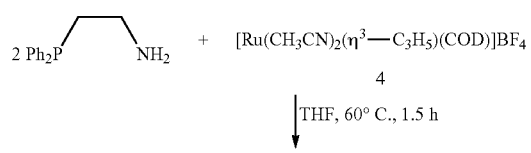

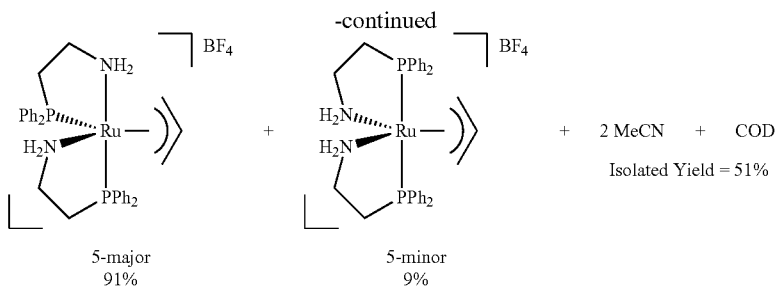

5-major
91%

5-minor
9%

Isolated Yield = 51%

Catalyst (5) was identified by $^1$H, $^{31}$P, gCOSY, $^1$H{$^{31}$P} COSY, $^1$H-$^{31}$P gHSQC, TROESY and gTOCSY NMR experiments, Mass Spectrometry and Elemental Analysis. (See also FIGS. 2 and 3) (J. A. Wiles, C. J. A. Daley, R. J. Hamilton, C. G. Leong, S. H. Bergens, *Organometallics*, 2004, 23, 4564; L. Saudan, C. M. Saudan, C. Debieux, P. Wyss, *Angew. Chem. Int. Ed.* 2007, 46, 7473; L. Saudan, P. Dupau, J. Riedhauser, P. Wyss, PCT Int. Pat. Appl. WO 2006/106484 A1, Oct. 12, 2006; PCT Int. Pat. Appl. WO 2006/106483, Apr. 4, 2006; L. Saudan, C. Saudan, PCT Int. Pat. Appl. WO 2008/065588 A1, Jun. 5, 2008; PCT Int. Pat. Appl. WO 2010/038209 A1, Apr. 8, 2010; L. Saudan, *Acc. Chem. Res.* 2007, 40, 1309.)

The catalyst [Ru(COD)(Anthracene)]BF$_4$ has also been shown to generate an active catalyst with similar activity to that of cis-[Ru(CH$_3$CN)$_2$($\eta^3$-C$_3$H$_5$)(COD)]BF$_4$ in a reaction with tethered amino phosphine.

Ligands

The bidentate diphosphine ligand (P—P) can be, for example, a compound of the Formula (I):

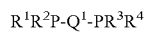

$$R^1R^2P-Q^1-PR^3R^4 \quad (I)$$

wherein $R^1$, $R^2$, $R^3$ and $R^4$ are each independently selected from (C$_{1-20}$)-alkyl, (C$_{3-20}$)-cycloalkyl and (C$_{6-18}$)-aryl, each group being optionally substituted with one or more substituents each independently selected from (C$_{1-6}$)-alkyl, fluoro-substituted (C$_{1-6}$)-alkyl, halo, (C$_{1-6}$)-alkoxy, fluoro-substituted (C$_{1-6}$)-alkoxy and (C$_{6-14}$)-aryl, or $R^1$ and $R^2$ and/or $R^3$ and $R^4$ are joined to form, together with the phosphorus atom to which they are attached, a saturated or unsaturated, monocyclic or polycyclic, substituted or unsubstituted ring system containing from 3 to 14 atoms, $Q^1$ is selected from unsubstituted or substituted (C$_{1-10}$)-alkylene and unsubstituted or substituted (C$_{1-10}$)-alkenylene where the substituents on $Q^1$ are each independently selected from one or more of (C$_{1-6}$)-alkyl, fluoro-substituted (C$_{1-6}$)-alkyl, halo, (C$_{1-6}$)-alkoxy, fluoro-substituted (C$_{1-6}$)-alkoxy and unsubstituted or substituted (C$_{6-14}$)-aryl; and/or adjacent substituents on $Q^1$ are joined together to form, including the carbon atoms to which they are attached, one or more unsubstituted or substituted 5-20-membered monocyclic, polycyclic, heterocyclic, carbocyclic, saturated, unsaturated or metallocenyl ring systems; where the term substituted with respect to the $Q^1$ substituents means that one or more of the available hydrogen atoms on the group are replaced with (C$_{1-6}$)-alkyl, fluoro-substituted (C$_{1-6}$) alkoxy, fluoro-substituted (C$_{1-6}$)-alkoxy, halo or (C$_{6-14}$)-aryl; and $Q^1$ is chiral or achiral.

In some examples, $R^1$, $R^2$, $R^3$ and $R^4$ are independently selected from (C$_{1-6}$)-alkyl, (C$_{3-10}$)-cycloalkyl and phenyl, each group being optionally substituted with one to three substituents independently selected from (C$_{1-4}$)-alkyl, fluoro-substituted (C$_{1-4}$)-alkyl, halo, (C$_{1-4}$)-alkoxy and fluoro-substituted (C$_{1-4}$)-alkoxy; $Q^1$ is selected from unsubstituted or substituted (C$_{1-8}$)-alkylene where the substituents on $Q^1$ are independently selected from one to three of (C$_{1-4}$)-alkyl, fluoro-substituted (C$_{1-4}$)-alkyl, halo, (C$_{1-4}$)-alkoxy, fluoro-substituted (C$_{1-4}$)-alkoxy, unsubstituted and substituted phenyl and substituted and unsubstituted naphthyl, or adjacent substituents are joined together to form, including the carbon atoms to which they are attached, one or more unsubstituted or substituted phenylene, cyclohexylene, naphthylene, pyridylene or ferrocenylene groups; and $Q^1$ is chiral or achiral.

In some examples $R^1$, $R^2$, $R^3$ and $R^4$ are all cyclohexyl, phenyl, xylyl or tolyl.

In some examples the compound of the Formula (I) is

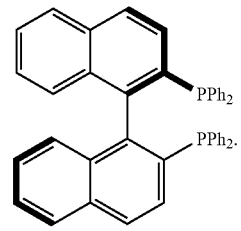

The bidentate diamino (N—N) ligand can be, for example, a compound of the Formula (II):

$$R^5R^6N-Q^2-NR^7R^8 \quad (II)$$

wherein $R^5$, $R^6$, $R^7$ and $R^8$ are independently selected from H, (C$_{1-20}$)-alkyl, (C$_{3-10}$)-cycloalkyl and (C$_{6-18}$)-aryl, the latter three groups each being optionally substituted with one or more substituents independently selected from (C$_{1-6}$)-alkyl, fluoro-substituted (C$_{1-6}$)-alkyl, halo, (C$_{1-6}$)-alkoxy, fluoro-substituted (C$_{1-6}$)-alkoxy and (C$_{6-14}$)-aryl, or $R^5$ and $R^6$ and/or $R^7$ and $R^8$ are joined to form, together with the nitrogen atom to which they are attached, a saturated or unsaturated, monocyclic or polycyclic, substituted or unsubstituted ring system containing from 3 to 14 atoms, or one of $R^5$ and $R^6$, and/or one of $R^7$ and $R^8$ are joined with a substituent on $Q^2$ to form, together with the nitrogen atom to which $R^5$, $R^6$, $R^7$ or $R^8$ is attached, a 4- to 10-membered saturated or unsaturated, monocyclic or bicyclic ring system, where if the nitrogen atom is part of aromatic ring or is bonded to an adjacent atom via a double bond, the other of $R^5$ or $R^6$ and $R^7$ or $R^8$ is not present, $Q^2$ is selected from unsubstituted or substituted (C$_1$-C$_{10}$)-alkenylene and unsubstituted or substituted (C$_1$-C$_{10}$)— wherein $R^5$, $R^6$, $R^7$ and $R^8$ are independently selected from H, (C$_{1-20}$)-alkyl, (C$_{3-10}$)-cycloalkyl and (C$_{6-18}$)-aryl, the latter three groups each being optionally substituted with one or more substituents independently selected from (C$_{1-6}$)-alkyl, fluoro-substituted (C$_{1-6}$)-alkyl, halo, (C$_{1-6}$)-alkoxy, fluoro-substituted (C$_{1-6}$)-alkoxy and (C$_{6-14}$)-aryl, or $R^5$ and $R^6$ and/or $R^7$ and $R^8$ are joined to form, together with the nitrogen atom to which they are attached, a saturated or unsaturated, monocyclic or polycyclic, substituted or unsubstituted ring system containing from 3 to 14 atoms, or one of $R^5$ and $R^6$, and/or one of $R^7$ and $R^8$ are joined with a substituent on $Q^2$ to form, together with the nitrogen atom to which $R^5$, $R^6$, $R^7$ or $R^8$ is attached, a 4- to 10-membered saturated or unsaturated, monocyclic or bicyclic ring system, where if the nitrogen atom is part of aromatic ring or is bonded to an adjacent atom via a double bond, the other of $R^5$ or $R^6$ and $R^7$ or $R^8$ is not present, $Q^2$ is selected from unsubstituted or substituted $(C_1-C_{10})$-alkenylene and unsubstituted or substituted $(C_1-C_{10})$-alkenylene where the substituents on $Q^2$ are independently selected from one or more of $(C_{1-6})$-alkyl, fluoro-substituted $(C_{1-6})$-alkyl, halo, $(C_{1-6})$-alkoxy, fluoro-substituted $(C_{1-6})$-alkoxy and unsubstituted or substituted phenyl; and/or adjacent substituents on $Q^2$ are joined together to form, including the carbon atoms to which they are attached, one or more unsubstituted or substituted 5-20-membered monocyclic, polycyclic, heterocyclic, carbocyclic, saturated, unsaturated or metallocenyl ring systems; the term substituted with respect to the $Q^2$ substituents means that one or more of the available hydrogen atoms on the group are replaced with $(C_{1-6})$-alkyl, fluoro-substituted $(C_{1-6})$-alkyl, $(C_{1-6})$-alkoxy, fluoro-substituted $(C_{1-6})$-alkoxy, halo or $(C_{6-14})$-aryl; and $Q^2$ is chiral or achiral.

In some examples, $R^5$, $R^6$, $R^7$ and $R^8$ are independently selected from H, $(C_{1-6})$-alkyl, $(C_{3-10})$-cycloalkyl and phenyl, the latter three groups each being optionally substituted with one to three substituents independently selected from $(C_{1-4})$-alkyl, fluoro substituted $(C_{1-4})$-alkyl, halo, $(C_{1-4})$-alkoxy and fluoro-substituted $(C_{1-4})$-alkoxy; and $Q^1$ is selected from unsubstituted or substituted $(C_1-C_8)$-alkylene where the substituents on $Q^1$ are independently selected from one to three of $(C_{1-4})$-alkyl, fluoro-substituted $(C_{1-4})$-alkyl, halo, $(C_{1-4})$-alkoxy, fluoro-substituted $(C_{1-4})$-alkoxy, unsubstituted and substituted phenyl and substituted and unsubstituted naphthyl, or adjacent substituents are joined together to form, including the carbon atoms to which they are attached, one or more unsubstituted or substituted phenylene, cyclohexylene, naphthylene, pyridylene or ferrocenylene groups; and $Q^1$ is chiral or achiral.

In some examples $R^5$, $R^6$, $R^7$ and $R^8$ are all H or $(C_{1-6})$-alkyl. In some examples, the optional substituents on $Q^2$ are selected from $(C_{1-4})$-alkyl and substituted or unsubstituted phenyl. In some examples, the optional substituents on $Q^2$ are selected from iso-propyl, phenyl and 4-methoxyphenyl.

In some examples, the compound of Formula (II) is

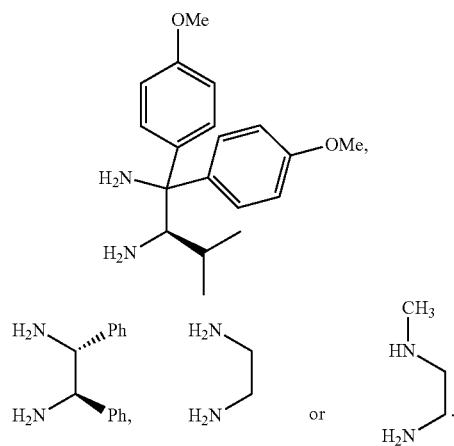

The bidentate aminophosphine (P—N) ligand can be, for example, a compound of the Formula (III)

$$R^9R^{10}P-Q^3-NR^{11}R^{12} \quad (III)$$

wherein $R^9$ and $R^{10}$ are independently as previously defined for $R^1$ to $R^4$; $R^{11}$ and $R^{12}$ are independently as previously defined for $R^5$ to $R^8$; and $Q^3$ is as previously defined for $Q^1$.

The tridentate diaminophosphine (P—N—N) ligand can be, for example, a compound of the Formula (IV):

$$R^{13}R^{14}-Q^4-NR^{15}-Q^5-NR^{16}R^{17} \quad (IV)$$

wherein $R^{13}$ and $R^{14}$ are independently as previously defined for $R^1$ to $R^4$, $Q^4$ and $Q^5$ are as previously defined for $Q^1$, $R^{15}$ is selected from H, $(C_{1-20})$-alkyl, $(C_{3-20})$-cycloalkyl and $(C_{6-18})$-aryl, the latter three groups each being optionally substituted with one or more substituents independently selected from $(C_{1-6})$-alkyl, fluoro-substituted $(C_{1-6})$-alkyl halo, $(C_{1-6})$-alkoxy, fluoro-substituted $(C_{1-6})$-alkoxy and $(C_{6-14})$-aryl, or $R^{15}$ is joined with a substituent on $Q^4$ and/or $Q^5$ to form, together with the nitrogen atom to which $R^{15}$ is attached, a 4- to 10-membered saturated or unsaturated, monocyclic or bicyclic ring system, and $R^{16}$ and $R^{17}$ are independently as previously defined for $R^5$-$R^8$.

The tridentate diaminophosphine (P—N—P) ligand can be, for example, a compound of the Formula (V):

$$R^{18}R^{19}P-Q^6-NR^{20}-Q^7-PR^{21}R^{22} \quad (V)$$

wherein $R^{18}$, $R^{19}$, $R^{21}$ and $R^{22}$ are independently as previously defined for $R^1$ to $R^4$, $Q^6$ and $Q^7$ are as previously defined for $Q^1$, and $R^{20}$ is as previously defined for $R^{15}$.

The tetradentate diaminodiphosphine (P—N—N—P) ligand can be, for example, a compound of the Formula (VIa) or (VIb):

$$R^{23}R^{24}P-Q^8-NR^{25}-Q^9-NR^{26}-Q10-PR^{27}R^{28} \quad (VIb)$$

$$R^{23}R^{24}P-Q^8=N-Q^9-N=Q^{10}-PR^{27}R^{28} \quad (VIb)$$

wherein $R^{23}$, $R^{24}$, $R^{27}$ and $R^{28}$ are independently as previously defined for $R^1$ to $R^4$, $Q^8$, $Q^9$ and $Q^{10}$ are independently as previously defined for $Q^1$, and $R^{25}$ and $R^{26}$ are independently as previously defined for $R^{15}$.

The monodentate phosphine (P) ligand can be, for example, a compound of the Formula (VII):

$$PR^{29}R^{30}R^{31} \quad (VII)$$

wherein $R^{29}$, $R^{30}$ and $R^{31}$ are independently selected from $(C_{6-18})$-aryl, $(C_{1-20})$-alkyl and $(C_{3-20})$-cycloalkyl, each being optionally substituted with one or more substituents independently selected from $(C_{1-6})$-alkyl, fluoro-substituted $(C_{1-6})$-alkyl, halo, $(C_{1-6})$-alkoxy, fluoro-substituted $(C_{1-6})$-alkoxy and $(C_{6-14})$-aryl, or $R^{29}$ and $R^{30}$ or $R^{29}$ and $R^{31}$ or $R^{30}$ and $R^{31}$ or $R^{29}$, $R^{30}$ and $R^{31}$ are joined to form, together with the phosphorous atom to which they are attached, a saturated or unsaturated, monocyclic or polycyclic, substituted or unsubstituted ring system containing from 3 to 14 atoms.

In some examples, $R^{29}$, $R^{30}$ and $R^{31}$ are independently selected from phenyl, $(C_{1-6})$-alkyl and $(C_{3-10})$-cycloalkyl, each being optionally substituted with one to three substituents independently selected from $(C_{1-4})$-alkyl, fluoro-substituted $(C_{1-4})$-alkyl, halo, $(C_{1-4})$-alkoxy and fluoro-substituted $(C_{1-6})$-alkoxy.

In some examples, $R^{29}$, $R^{30}$ and $R^{31}$ are all cyclohexyl, phenyl, xylyl or tolyl.

The monodentate amino (N) ligand can be, for example, a compound of the formula (VIII):

$$NR^{32}R^{33}R^{34} \quad (VIII)$$

wherein $R^{32}$, $R^{33}$ and $R^{34}$ are independently selected from H, $(C_{1-20})$-alkyl, $(C_{3-20})$-cycloalkyl and $(C_{6-18})$-aryl, the latter three groups each being optionally substituted with one or more substituents independently selected from $(C_{1-6})$-alkyl, fluoro-substituted $(C_{1-6})$-alkyl, halo, $(C_{1-6})$-alkoxy, fluoro-substituted $(C_{1-6})$-alkoxy and $(C_{6-14})$-aryl, or $R^{32}$ and $R^{33}$ or $R^{32}$ and $R^{34}$ or $R^{33}$ and $R^{34}$ or $R^{32}$, $R^{33}$ and $R^{34}$ are joined to form, together with the nitrogen atom to which they are attached, a saturated or unsaturated, monocyclic or polycyclic, substituted or unsubstituted ring system containing from 3 to 14 atoms.

In some examples, $R^{32}$, $R^{33}$ and $R^{34}$ are independently selected from H, $(C_{1-6})$-alkyl, $(C_{3-10})$-cycloalkyl and phenyl, the latter three groups each being optionally substituted with one to three substituents independently selected from $(C_{1-4})$-alkyl, fluoro-substituted $(C_{1-4})$-alkyl, halo, $(C_{1-4})$-alkoxy and fluoro-substituted $(C_{1-4})$-alkoxy.

Some suitable ligands for the transition metal catalyst include, but are not limited to:

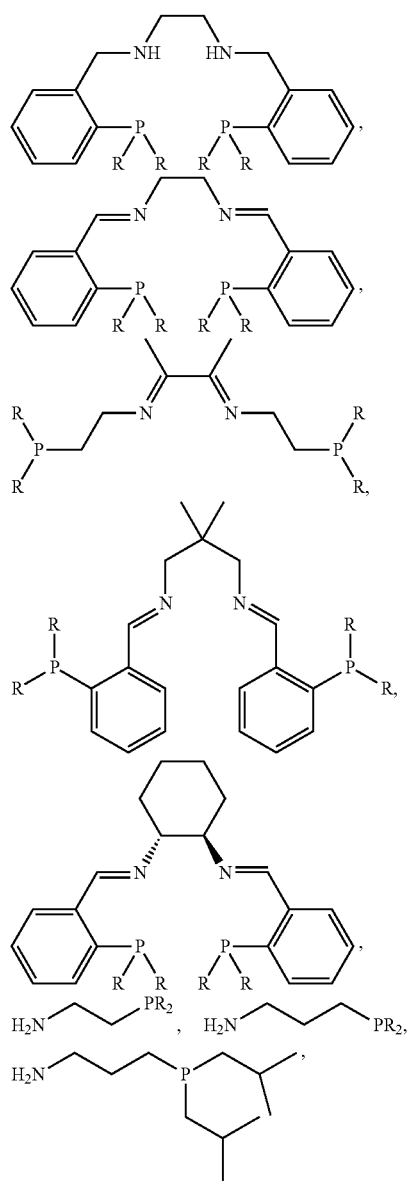

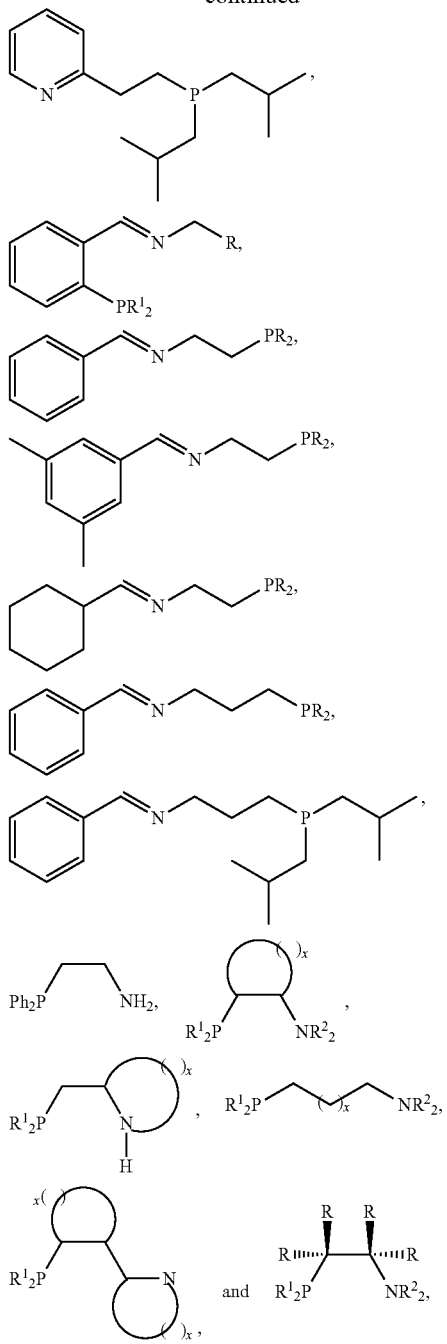

wherein R is alkyl and/or aryl and/or H, $R^1$ is alkyl and/or aryl, $R^2$ is alkyl and/or aryl and/or H, and rings can be either alkyl or aryl, and x>1.

In certain specific examples, ligands can include:

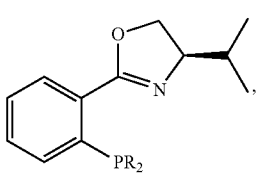

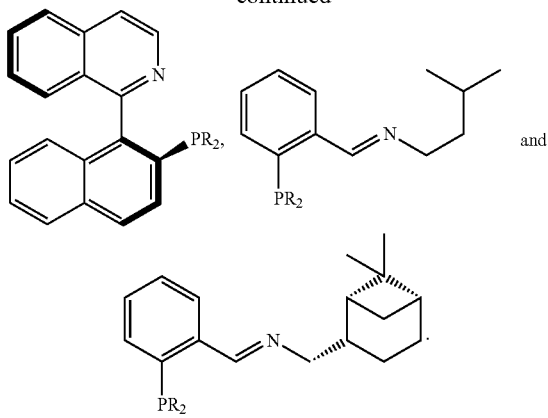

In some examples, the neutral monodentate ligand is water, acetonitrile, DMF, ammonia, pyridine, tetrahydrofuran (THF), CO, t-BuCN or t-BuNC.

In some examples, the anionic monodentate ligand is halo, $(C_{1-6})$-alkoxy, hydroxy, thiocyanate, cyano, carboxylate, sulfonates or nitrates. In some specific examples, halo is chloro.

Substrates

In some examples, the substrate comprising one or more amide moieties is a compound of the Formula (IX):

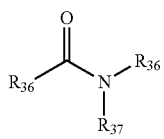

(IX)

wherein $R^{35}$ and $R^{36}$ are independently selected from $(C_{1-20})$-alkyl, $(C_{3-20})$-cycloalkyl and $(C_{6-18})$-aryl, each group being optionally substituted, wherein the optional substituents are independently selected from one or more of $(C_{1-6})$-alkyl, fluoro-substituted $(C_{1-6})$-alkyl, halo, $(C_{1-6})$-alkoxy, fluoro-substituted $(C_{1-6})$-alkoxy and $(C_{6-14})$-aryl and/or one or more of the carbon atoms is optionally replaced with a heteromoiety selected from O, S, N, NH and N—$(C_{1-6})$-alkyl, or $R^{35}$ and $R^{36}$ are joined together to form, including the carbon atoms to which they are attached and the amide nitrogen, an unsubstituted or substituted 5-20-membered monocyclic, polycyclic, heterocyclic, carbocyclic, saturated or unsaturated ring system, wherein the optional substituents are selected from one or more of $(C_{1-6})$-alkyl, fluoro-substituted $(C_{1-6})$-alkyl, halo, $(C_{1-6})$-alkoxy, fluoro-substituted $(C_{1-6})$-alkoxy and $(C_{6-14})$-aryl; and $R^{37}$ is selected from H, $(C_{1-6})$-alkyl, $(C_{3-8})$-cycloalkyl and $(C_{6-14})$-aryl, the latter three groups being optionally substituted with one or more of $(C_{1-6})$-alkyl, fluoro-substituted $(C_{1-6})$-alkyl, halo, $(C_{1-6})$-alkoxy, fluoro-substituted $(C_{1-6})$-alkoxy and $(C_{6-14})$-aryl and/or one or more of the carbon atoms is optionally replaced with a heteromoiety selected from O, S, N, NH and N—$(C_{1-6})$-alkyl; and where the compound of Formula (IX) is chiral or achiral.

In some examples, $R^{37}$ is H, $(C_{1-3})$-alkyl, $(C_{3-6})$-cycloalkyl or phenyl, the latter three groups each being optionally substituted, wherein the optional substituents are independently selected from $(C_{1-6})$-alkyl, fluoro-substituted $(C_{1-6})$-alkyl, halo, $(C_{1-6})$-alkoxy, fluoro-substituted $(C_{1-6})$-alkoxy and phenyl.

In some examples, $R^{35}$ and $R^{36}$ are joined together to form, including the carbon atoms to which they are attached and the amide carbon, a polycyclic $(C_{8-12})$-cycloalkyl or $(C_{8-12})$-cycloalkenyl ring system, each being optionally substituted with one to five substituents independently selected from $(C_{1-6})$-alkyl, fluoro-substituted $(C_{1-6})$-alkyl, halo, $(C_{1-6})$-alkoxy, fluoro-substituted $(C_{1-6})$-alkoxy and $(C_6)$-aryl, and in which one to five carbon atoms in the polycyclic $(C_{8-12})$-cycloalkyl or $(C_{8-12})$-cycloalkenyl ring system are optionally replaced with a heteromoiety selected from O, N, NH, N—$(C_{1-6})$-alkyl and S.

In some examples, $R^{35}$ and $R^{36}$ are joined to form, including the carbon atoms to which they are attached and the imide nitrogen, a ring system selected from:

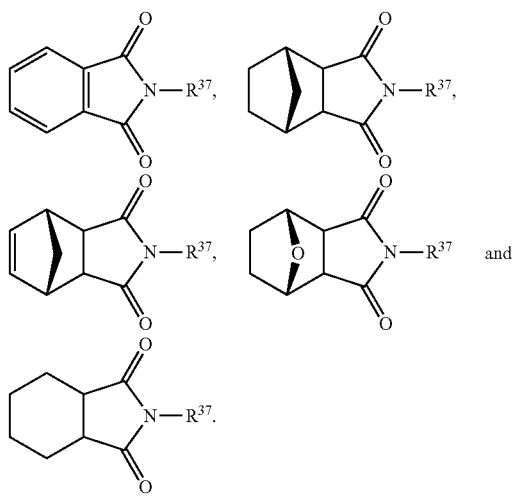

The compound of formula (IX) can also be, for example, mono-reduced to a compound of the Formula (Xa) or (Xb)

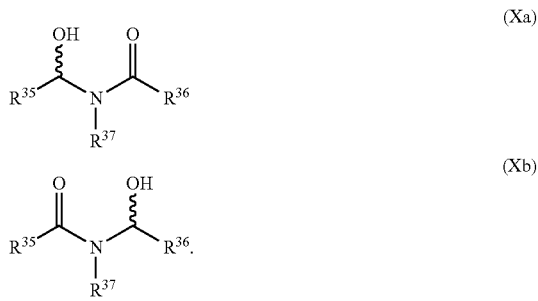

In certain examples, suitable substrates include the following, wherein $R^1$ to $R^4$ may be components of a ring, shown below.

carboxylic acid derivative

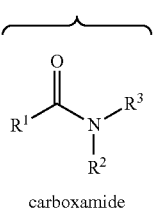

carboxamide

-continued
carbonic acid derivatives

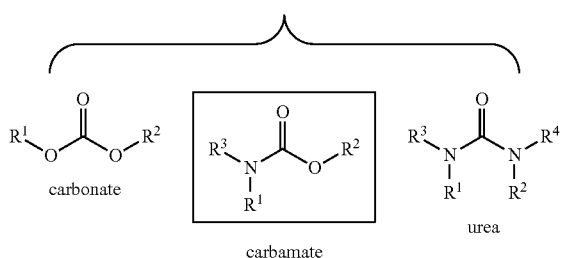

In one example, the substrate can be a cyclic carbamate, a specific example of this reaction performed with [Ru(Cl)₂(Cy₂PCH₂CH₂NH₂)₂] (Cy=cyclohexyl) as the transition metal catalyst. which is shown below:

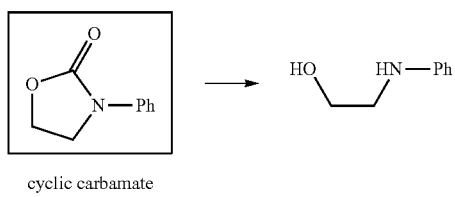 [SMILES: O=C1OCCN1c1ccccc1 ; OCCNc1ccccc1]

cyclic carbamate

Process

Described herein is a process for hydrogenating a wide variety of cyclic and acyclic amides, and analogues thereof, to the corresponding alcohol and amine products using a transition metal catalyst. The present reaction can be carried out under mild conditions, such as with low catalyst loading, low hydrogen pressure, and low temperature to effect the transformation, compared with other known amide bond reductions. The present reactions can also be selective for amide bond cleavage, and can be carried out in base free conditions.

The present catalysts and methods are also capable of carrying out hydrogenation reactions on other amide derivatives, and carboxylic acid derivatives including but not limited to carboxamide, and carbonic acid derivatives including but not limited to carbonates, carbamates and ureas.

Processes of the present invention may be conveniently practiced in the form of a kit. Such a kit preferably contains the appropriate compounds and/or compositions, and instructions for the use thereof.

Selection of the appropriate solvent for the present catalytic process will be dependent on a number of factors including, for example, solubility of substrate, reactants and/or product(s), cost, availability, and temperature and pressure of the reaction. The selection of a specific solvent will be well within the abilities of a person of ordinary skill in the art. In some examples, the process is performed in a solvent selected from tetrahydrofuran (THF), diethyl ether, chlorinated solvents, toluene and mixtures thereof.

As noted above, the present process is optionally performed in the presence of a base. In some examples, the base is an organic non-coordinating base, a carbonate salt, a carboxylate salt, an alcoholate salt, a hydroxide salt or a silazine salt. In some specific examples, the base can be, for example, tBuOK or $[(CH_3)_3Si]_2NK$. In alternative examples, the present process is performed in the absence of a base.

The present process is performed in the presence of a hydrogen source, specifically $H_2$. In some examples, the hydrogen gas is used at a pressure in the range of about 1 atm to about 100 atm. In some examples, the hydrogen gas is used at a pressure in the range of about 40 atm to about 60 atm. In some examples, the hydrogen gas is used at a pressure of 50 atm or less. In some examples, the hydrogen gas is used at a pressure of 10 atm or less. In other specific examples, the hydrogen gas is used at a pressure of between about 1 atm to about 10 atm.

In some examples, the process is performed at a temperature of about –50° C. to about 150° C.

To gain a better understanding of the invention described herein, the following examples are set forth. It should be understood that these examples are for illustrative purposes only. Therefore, they should not limit the scope of this invention in any way.

EXAMPLES

Example 1

Synthesis of Substrates

Preparation of N-Methylsulfonylpyrrolidin-2-one (2a)

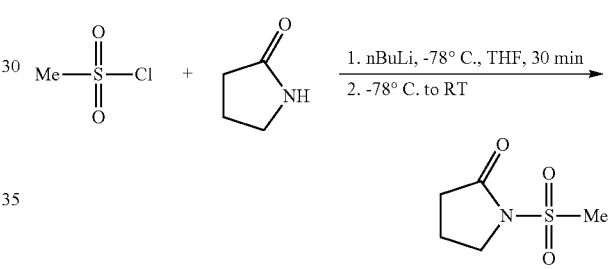

N-Methylsulfonylpyrrolidin-2-one (2a) was prepared according to a procedure reported by Ikariya and co-workers. (M. Ito, L. W. Koo, A. Himizu, C. Kobayashi, A. Sakaguchi, T. Ikariya, *Angew. Chem. Int. Ed.* 2009, 48, 1324.) A solution of nBuLi (2.5 M, 11.8 mL, 29.4 mmol) in n-hexane was added drop-wise over 30 min to a stirred solution of 2-pyrrolidinone (24.5 mmol) in 50 mL of anhydrous THF at −78° C. under Argon. The resulting white slurry was then stirred for an additional 30 min before being quenched with freshly distilled methansulfonylchloride (24.5 mmol). The reaction mixture was then allowed to warm gradually to RT. The mixture that resulted was then washed with a saturated solution of NH₄Cl after which it was extracted three times with AcOEt. The combined AcOEt layers were then washed with brine and dried over anhydrous MgSO₄ before being concentrated under reduced pressure. The product was purified by column chromatography using 3:1 Hexanes:AcOEt. Yield: 50%.

Preparation of N-Acetylpyrrolidin-2-one (2b)

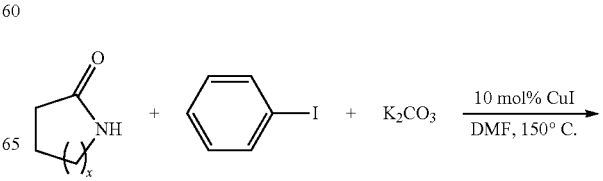

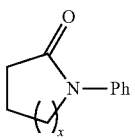

N-Acetylpyrrolidin-2-one (2b) was prepared according to a procedure described by MacKenzie and co-workers. (J. Seyden-Penne, *Reductions by the Alumino and Borohydrides in Organic Synthesis*, 2nd Ed., Wiley-VCH, New York, 1997. G. W. Gribble, *Chem. Soc. Rev.* 1998, 27, 395.) A mixture of 2-pyrrolidinone (39.3 mmol) and acetic anhydride (78.7 mmol) was added to a 3-neck flask equipped with a magnetic stir bar. The contents of the flask were then heated at reflux for 2 h under Argon. The pale yellow mixture that resulted was then allowed to cool to RT before being concentrated in vacuo. The crude product was then purified by distillation. Yield: 96%

Preparation of N-Phenylpyrrolidin-2-one (2c) and N-Phenylpiperidone (6)

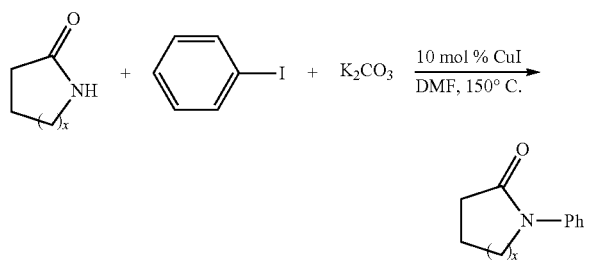

N-Phenylpyrrolidin-2-one (2c) and N-Phenylpiperidone (6) were prepared by a modification to the procedure reported by Ukita and co-workers. (G. Pelletier, W. S. Bechara, A. B. Charette, *J. Am. Chem. Soc.* 2010, 132, 12817; S. Das, D. Addis, S. Zhou, K. Junge, M. Beller, *J. Am. Chem. Soc.* 2010, 132, 1770; Y. Sunada, H. Kawakami, T. Imaoka, Y. Matoyama, H. Nagashima. *Angew. Chem. Int. Ed.* 2009, 48, 9511.) A mixture of iodobenzene (24.8 mmol), lactam (12.4 mmol), anhydrous $K_2CO_3$ (12.4 mmol) and CuI in anhydrous DMF was refluxed at 150° C. overnight under an Argon atmosphere. The reaction mixture was then allowed to cool to RT before adding a minimal amount of a 2.5% aqueous $NH_4OH$ solution. The resulting blue solution was then extracted twice with AcOEt and the combined AcOEt layers were washed with brine before being collected and dried over anhydrous $MgSO_4$. The organic layer was then concentrated in vacuo. The product was then purified by column chromatography using 2:1 Hexanes: AcOEt. Yields were 50% and 40% respectively.

Preparation of N,N-Diphenylbenzamide (8a)

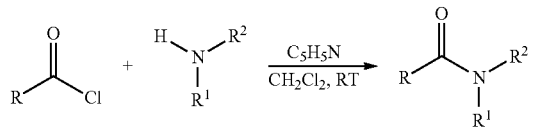

N,N-Diphenylbenzamide (8a) was prepared by a modification to the procedure reported by Charette and co-workers. (B. Wojcik, H. Adkins, *J. Am. Chem. Soc.* 1934, 56, 2419; b) R. M. King, U.S. Pat. No. 4,448,998, May 15, 1984.) Benzoyl chloride (4.39 mmol) was added drop-wise to a rapidly stirred solution of diphenylamine (3.66 mmol) and pyridine (18.29 mmol) in 40.0 mL of anhydrous $CH_2Cl_2$ at RT. The reaction mixture was then stirred overnight under Argon. TLC was used to monitor the reaction. Upon completion, the reaction was diluted with AcOEt and transferred to a separation funnel. The organic layer was then washed with an equal volume of 1N HCl. The organic layer was collected, washed with an equivalent volume of brine and dried over $MgSO_4$ before being concentrated under reduced pressure. The product was purified by trituration in warm hexanes and isolated by gravity filtration. Yield was 60%.

Preparation of N-Methyl-N-Phenylbenzamide (8b) and 1-Benzoylpiperidine (8d)

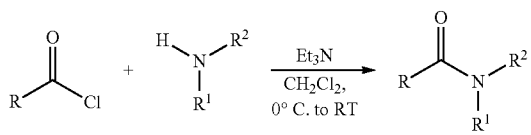

N-Methyl-N-Phenylbenzamide (8b) and 1-Benzoylpiperidine (8d) were prepared by a modification to the procedure reported by Charette and co-workers. (B. Wojcik, H. Adkins, *J. Am. Chem. Soc.* 1934, 56, 2419; R. M. King, U.S. Pat. No. 4,448,998, May 15, 1984.) Benzoyl chloride (52.8 mmol) was added drop-wise to a rapidly stirred solution of the amine (58.1 mmol) and triethylamine (66.1 mmol) in 40.0 mL of anhydrous $CH_2Cl_2$ at 0° C. The reaction mixture was then allowed to warm up to RT and stirred over overnight under Argon. The mixture was then diluted with an equivalent volume of $CH_2Cl_2$ (40.0 mL) before being transferred to a separation funnel. The combined $CH_2Cl_2$ layers were then washed with 40.0 mL of an aqueous 1N HCl. The organic layer was collected, washed with an equivalent volume of brine and dried over anhydrous $MgSO_4$ before being concentrated under reduced pressure. The product was then purified by distillation. Yields were 90% and 80% respectively.

Preparation of Acetanilide (8j)

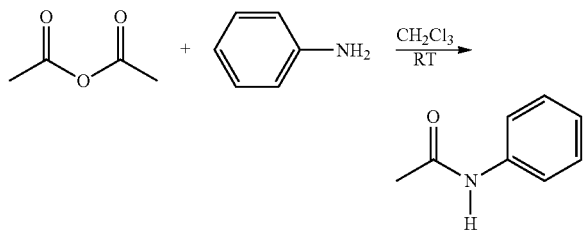

Acetanilide (8j) was prepared according to a procedure described by Fagnou and co-workers. (C. Hirosawa, N. Wakasa, T. Fuchikami, *Tetrahedron Lett.* 1996, 37, 6749.) The acid anhydride (88.7 mmol) was added drop wise to a rapidly stirred solution of aniline (73.9 mmol) in 200 mL of anhydrous $CH_2Cl_2$ under Argon at RT. Thin Layer Chromatography (TLC) was then used to monitor the progress of the reaction. Upon completion, the reaction was then quenched with a saturated aqueous solution of Na$_2$CO$_3$. The organic layer was then collected, washed with brine and dried over anhydrous MgSO$_4$ before being concentrated under reduced pressure. The product was the purified by recrystallization in hot water. Yield: 90%.

Spectroscopic Identification of Substrates

N-Methylsulfonylpyrrolidin-2-one (2a): Crystalline colorless solid: $^1$H NMR (499.815 MHz, CDCl$_3$, 27° C.): δ 2.14 (2H, p, J=7.7 Hz, CH$_2$), δ 2.57 (2H, t, J=8 Hz, CH$_2$), δ 3.25 (3H, s, CH$_3$), δ 3.86 (2H, J=7 Hz, CH$_2$). (M. Ito, L. W. Koo, A. Himizu, C. Kobayashi, A. Sakaguchi, T. Ikariya, *Angew. Chem. Int. Ed.* 2009, 48, 1324.)

N-Acetylpyrrolidin-2-one (2b): Colorless oil: $^1$H NMR (499.815 MHz, CDCl$_3$, 27° C.): δ 2.01 (2H, p, J=9 Hz, CH$_2$), δ 2.48 (3H, s, CH$_3$), δ 2.58 (2H, t, J=12 Hz, CH$_2$), δ 3.78 (2H, t, J=11.5 Hz, CH$_2$). (M. W. Irvine, G. L. Patrick, J. Kewney, S. F. Hastings, S. J. Mackenzie, *Bioorg. Med. Chem. Lett.* 2008, 18, 2032.)

N-Phenylpyrrolidin-2-one (2c): White powder: $^1$H NMR (499.815 MHz, CDCl$_3$, 27° C.): δ 2.15 (2H, p, J=7.2 Hz, CH$_2$), δ 2.60 (2H, t, J=8 Hz, CH$_2$), δ 3.86 (2H, t, J=7 Hz, CH$_2$), δ 7.13 (1H, t, J=7.5 Hz, aromatic CH), δ 7.36 (2H, t, J=7.5 Hz, aromatic 2 CH), δ 7.60 (2H, d, J=8 Hz, aromatic 2 CH). (M. Sugahara, T. Ukita, *Chem. Pharm. Bull.* 1997, 45, 719.)

N-Methylpyrrolidin-2-one (2d): Colorless oil: $^1$H NMR (498.122 MHz, CDCl$_3$, 27° C.): δ 2.00 (2H, p, J=7 Hz, CH$_2$), δ 2.35 (2H, t, J=8.2 Hz, CH$_2$), δ 2.82 (3H, s, CH$_3$), δ 3.36 (2H, t, J=7 Hz, CH$_2$).

2-Pyrrolidinone (2e): Colorless viscous oil: (499.815 MHz, CDCl$_3$, 27° C.): δ 2.05 (2H, p, J=7.7 Hz, CH$_2$), δ 2.23 (2H, t, J=8 Hz, CH$_2$), δ 3.35 (211, t, J=7 Hz, CH$_2$), δ 7.10 (1H, brs, NH).

N-Phenylpiperidinone (6): White powder: $^1$H NMR (498.122 MHz, CDCl$_3$, 27° C.): δ 1.93 (4H, m, 2 CH$_2$), δ 2.55 (2H, t, J=6 Hz, CH$_2$), δ 3.63 (2H, t, J=6 Hz, CH$_2$), δ 7.24 (3H, m, aromatic 3 CH), δ 7.38 (2H, m, aromatic 2 CH). (M. Sugahara, T. Ukita, *Chem. Pharm. Bull.* 1997, 45, 719.)

ε-Caprolactam (7): Colorless crystals: $^1$H NMR (498.122 MHz, CDCl$_3$, 27° C.): δ 1.62-1.76 (6H, m, 3 CH$_2$), δ 2.46 (2H, m, CH$_2$), δ 3.20 (2H, m, CH$_2$), δ 5.90 (1H, brs, NH).

N,N-Diphenylbenzamide (8a): White powder: (498.124 MHz, CDCl$_3$, 27° C.): δ 7.13-7.21 (8H, m, aromatic 8 CH), δ 7.24-7.29 (511, m, aromatic 5 CH), δ 7.43 (2H, d, J=7.5 Hz, aromatic 2 CH). (G. Barbe, A. B. Charette, *J. Am. Chem. Soc.* 2008, 130, 18.)

N-Methyl-N-Phenylbenzamide (8b): Straw colored viscous liquid: $^1$H NMR (498.122 MHz, CDCl$_3$, 27° C.): δ 3.50 (3H, s, CH$_3$), δ 7.03 (2H, d, J=8 Hz, aromatic 2 CH), δ 7.15-7.19 (3H, m, aromatic 3 CH), δ 7.19-7.25 (3H, m, aromatic 3 CH), 7.29 (2H, d, J=8 Hz, aromatic 2 CH). (G. Barbe, A. B. Charette, *J. Am. Chem. Soc.* 2008, 130, 18.)

N,N-Dimethylbenzamide (8c): White powder: $^1$H NMR (498.122 MHz, CDCl$_3$, 27° C.): δ 2.97 (3H, brs, CH$_3$), δ 3.01 (3H, brs, CH$_3$), δ 7.38-7.40 (5H, m, aromatic 5 CH).

1-Benzoylpiperidine (8d): Straw colored vicous oil, white solid upon seeding: (499.815 MHz, CDCl$_3$, 27° C.): δ 1.40-1.70 (6H, m, 3 CH$_2$), δ 3.29 (2H, brs, CH$_2$), δ 3.70 (2H, brs, CH$_2$), δ 7.37 (5H, s, aromatic 5 CH). (G. Barbe, A. B. Charette, *J. Am. Chem. Soc.* 2008, 130, 18.)

Benzanilide (8e): Off-white powder: (499.815 MHz, CDCl$_3$, 27° C.): δ 7.16 (1H, t, J=7.2 Hz, aromatic CH), δ 7.38 (2H, t, J=7.8 Hz, aromatic 2 CH), δ 7.49 (2H, t, J=7.5 Hz, aromatic 2 CH), δ 7.55 (1H, t, J=7.5 Hz, aromatic CH), δ 7.64 (2H, d, J=8.2 Hz, aromatic 2 CH), 7.82 (1H, brs, NH), δ 7.86 (2H, d, J=7 Hz, aromatic 2 CH).

N-Methylbenzamide (80: White crystals: $^1$H NMR (498.124 MHz, CDCl$_3$, 27° C.): δ 3.01 (3H, d, J=5 Hz, CH$_3$), δ 6.17 (1H, brs, NH), δ 7.42 (2H, t, J=7.5 Hz, aromatic 2 CH), δ 7.48 (1H, t, J=7.5 Hz, aromatic CH), δ 7.76 (2H, d, J=8.2 Hz, aromatic 2 CH).

N,N-Diphenylacetamide (8g): White powder: (499.815 MHz, CDCl$_3$, 27° C.): δ 2.09 (3H, s, CH$_3$), δ 7.29 (4H, d, J=8 Hz, aromatic 4CH), δ 7.10-7.50 (6H, m, aromatic 6CH).

N-Methylacetanilide (8h): Colorless crystals: $^1$H NMR (498.122 MHz, CDCl$_3$, 27° C.): δ 1.86 (3H, s, CH$_3$), δ 3.26 (3H, s, CH$_3$), δ 7.18 (2H, d, J=7.8 Hz, aromatic 2 CH), δ 7.33 (1H, t, J=7.5 Hz, aromatic CH), δ 7.42 (2H, t, J=7.2 Hz, aromatic 2 CH).

N,N-Dimethylacetamide (8i): Colorless liquid: $^1$H NMR (498.122 MHz, CDCl$_3$, 27° C.): δ 2.05 (3H, s, CH$_3$), δ 2.91 (3H, s, CH$_3$), δ 2.98 (3H, s, CH$_3$).

Acetanilide (8j): Colorless crystals: $^1$H NMR (499.815 MHz, CDCl$_3$, 27° C.): δ 2.18 (3H, s, CH$_3$), δ 7.10 (1H, t, J=7.5 Hz, aromatic CH), δ 7.15 (1H, brs, NH), δ 7.32 (2H, t, J=8 Hz, aromatic 2 CH), δ 7.49 (2H, d, J=7.5 Hz, aromatic 2 CH). (D. R. Stuart, M. Bertrand-Laperle, K. M. N. Burgess, K. Fagnou, *J. Am. Chem. Soc.* 2008, 130, 16474)

Example 2

Synthesis of Ruthenium Catalysts

Preparation of Catalyst [Ru(Ph$_2$PCH$_2$CH$_2$NH$_2$)$_2$(η$^3$-C$_3$H$_5$)]BF$_4$ (5)

In a glove box, 0.75 mmol of cis-[Ru(CH$_3$CN)$_2$(η$^3$-C$_3$H$_5$)(COD)]BF$_4$ (4), ((COD is 1,5-cyclooctadiene), was added to a schlenk flask equipped with a stir bar. The flask was then attached to a schlenk line and 4.0 mL of freshly distilled THF added. The mixture was then rapidly stirred and a 1.0 mL THF solution of Ph$_2$PCH$_2$CH$_2$NH$_2$, 3 (1.5 mmol, 2 equiv) in an NMR tube was added with the aid of a cannula. Any residue in the NMR tube and cannula was washed into the flask with 7.0 mL of THF. The contents of the flask were then heated at 60° C. for 1.5 h to form a golden-brown solution. The solution was allowed to cool to RT before the solvent was removed by evaporation. The crude mixture was then dissolved in 2.0 mL of freshly distilled CH$_2$Cl$_2$ and the product, (5) was precipitated from the solution using copious amounts of freshly distilled Et$_2$O. The light yellow solid that resulted was isolated via filtration under Argon and washed three times with 5.0 mL aliquots of Et$_2$O. The solid was then dried in vacuo. Yield: 51%. NMR spectra of the filtrate (after the solvent was removed under vacuum) showed it contained (5) as the sole Ru-containing species. (See FIGS. 2 and 3).

In Situ Preparation of the Catalyst (5) with [(CH$_3$)$_3$Si]$_2$NK

The preparation of catalyst precursor (4) was previously described by Bergens et al. (J. A. Wiles, C. J. A. Daley, R. J. Hamilton, C. G. Leong, S. H. Bergens, *Organometallics*. 2004, 23, 4564.)

A mixture of cis-[Ru(CH$_3$CN)$_2$(η$^3$-C$_3$H$_5$)(COD)]BF$_4$ (4), (0.005 mmol) and 2 equiv of Ph$_2$PCH$_2$CH$_2$NH$_2$, (0.010 mmol) in freshly distilled anhydrous THF (0.5 mL) under Argon was heated in an NMR tube using water bath at 60° C. with periodic shaking for 30 min. The resulting solution was cooled for 1 min to 0° C. using an ice bath before cooling to −78° C. using a dry ice/acetone bath. H$_2$ (~2 atm) was cannulated into the NMR tube at −78° C. The tube was then shaken for 10 sec, and promptly returned to the bath. This shaking process was repeated nine times. 40/50 equiv. (0.20-0.25 mmol) of $[(CH_3)_3Si]_2NK$ in THF (0.5 mL) was subsequently added via cannula under $H_2$ (~2 atm). The shaking process was carried out an additional ten times. The solution color changed from light yellow to orange during this addition.

Preparation of $[RuCl_2(Ph_2PCH_2CH_2NH_2)_2]$ (2)

The preparation of catalyst (2) was previously described by Saudan et al. (L. Saudan, P. Dupau, J-J. Riedhauser, P. Wyss, U.S. Pat. No. 7,763,758 B2. Sep. 12, 2007.)

In a glove box, $[RuCl_2(PPh_3)_3]$ (0.25 mmol) was added to a schlenk flask equipped with a magnetic stir bar. The flask was then attached to a schlenk line and 3.4 mL of freshly distilled toluene added. The mixture was then rapidly stirred. A 1.7 mL toluene solution of $Ph_2PCH_2CH_2NH_2$, (0.50 mmol) in an NMR tube was then added via a cannula. Any residue in the NMR tube and cannula was washed into the flask with 1.7 mL of toluene. The light yellow mixture was then heated at 100° C. for 6 h. The yellow suspension that resulted was allowed to cool to RT before collecting the precipitate by filtration under Argon. The precipitate was then washed with 10.0 mL portions of toluene, three times (until colorless). The yellow solid was then dried in vacuo. Yield: 90%. Note: Excessive scraping of the product should be minimised to prevent the build-up of static electricity.

Characterization of $[RuCl_2(Ph_2PCH_2CH_2NH_2)_2]$ (2)

The identity of compound (2) was confirmed using information reported in the literature. (M. Kilner, D. V. Tyers, S. P. Crabtree, M. A. Wood, PCT Int. Pat. Appl. WO 03/093208 A1, Nov. 13, 2003; A. A. N. Magro, G. R. Eastham, D. Cole-Hamilton, *Chem. Commun.* 2007, 3154; US Pat. 2010/0010261 A1, Jan. 14, 2010.) $^{31}P$ $\{^{1}H\}$ NMR $-$(161.839 MHz, freshly distilled $CD_2Cl_2$, 27° C.): 55.4 ppm (trans, d, 2 $J_{P-P}$=32 Hz), 61.8 ppm (cis, s), 66.8 ppm (trans, d, $2J_{P-P}$=32 Hz). Ratio cis:trans is 52:48. HRMS (ESI*+) m/z calculated for $C_{28}H_{32}Cl_2N_2P_2[^{102}Ru]$ (M*+): 630.0456. Found: 630.0455. Difference (ppm): $-$0.12 ppm. Elemental analysis calculated for $C_{28}H_{32}Cl_2N_2P_2Ru$: N, 4.44; C, 53.34; H, 5.12. Found: N, 4.55; C, 53.50; H, 4.94.

Characterization of $[Ru(\eta^3-C_3H_5)(Ph_2PCH_2CH_2NH_2)_2]BF_4$ (5)

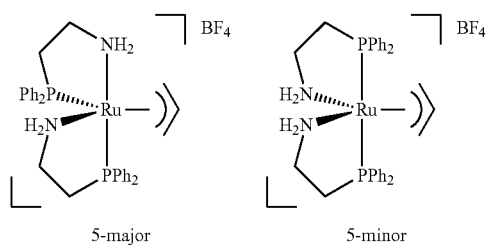

5-major    5-minor

Figure 2:
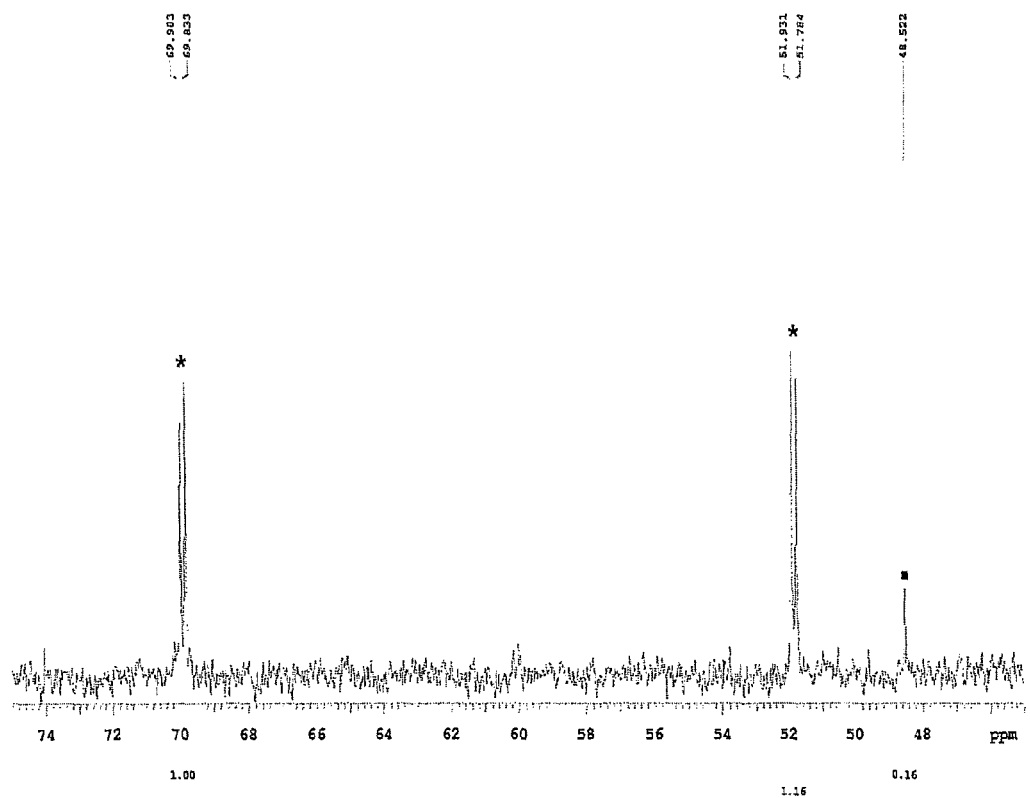
FIG. 2 graphically depicts the $^{31}$P{$^1$H} NMR spectrum of [Ru($\eta^3$-C$_3$H$_5$)(Ph$_2$PCH$_2$CH$_2$NH$_2$)$_2$]BF$_4$ (5) in CD$_2$Cl$_2$.

FIG. 2 shows the $^{31}P$ $\{^{1}H\}$ NMR Spectrum of the mixture of (5)-major and (5)-minor. 201.643 MHz, freshly distilled $CD_2Cl_2$, 27° C.: 48.5 ppm (minor, s), 51.9 ppm (major, d, $2J_{P-P}$=29.6 Hz), 69.9 ppm (major, d, $2J_{P-P}$=30.2 Hz). Ratio major:minor is 91:9 (best sample). HRMS (ESI+) m/z calculated for $C_{31}H_{37}N_2P_2[^{102}Ru]$ (M+): 601.147. Found: 601.1476. Difference (ppm): 0.98 ppm. Elemental analysis calculated for $C_{31}H_{37}N_2P_2BF_4Ru$: N, 4.07; C, 54.16; H, 5.42. Found: N, 3.81; C, 54.24; H, 5.61.

Figure 3:
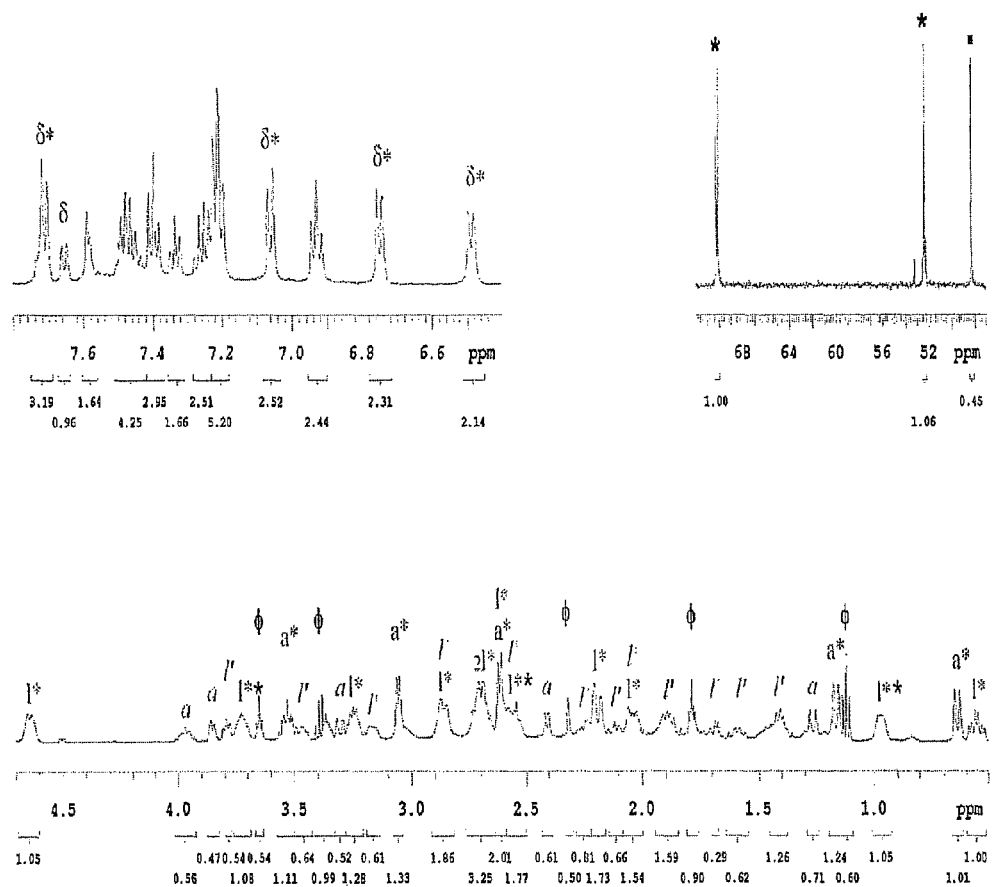
FIG. 3 graphically depicts the $^{31}$P{$^1$H} and $^{31}$P NMR spectra of [Ru($\eta^3$-C$_3$H$_5$)(Ph$_2$PCH$_2$CH$_2$NH$_2$)$_2$]BF$_4$ (5)

FIG. 3 shows the $^{1}H\{^{31}P\}$ and $^{31}P$ NMR spectra of $[Ru(\eta^3-C_3H_5)(Ph_2PCH_2CH_2NH_2)_2]BF_4$ recorded on a Varian Inova four-channel 500 MHz spectrometer at $-$60° C. in $CD_2Cl_2$. Peaks were assigned using $^{1}H$, $^{31}P$, gCOSY, $^{1}H\{^{31}P\}$gCOSY, $^{1}H$-$^{31}P$ gHSQC, TROESY and gTOCSY NMR experiments. Legend: Major Isomer (*); Minor isomer (■); Residual Solvent (ϕ); Major Allyl (a*); Minor Allyl (a); Major 2-(diphenyl-phosphino)ethylamine ligand (NH=1**, CH=1*); Minor 2-(diphenylphosphino)-ethylamine ligand (l', l); Major Ortho-Aromatic CH (δ*); Minor Ortho-Aromatic CH (δ)

Figure 4:
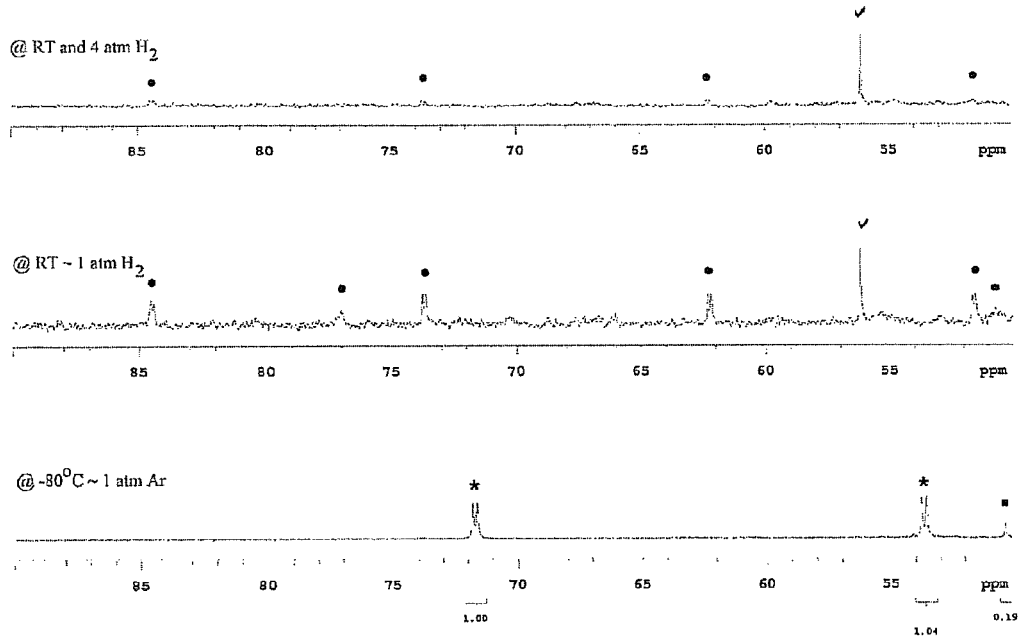
FIG. 4 graphically depicts the preliminary $^{31}$P{$^1$H} NMR Study on the reactivity of (5) towards H$_2$ and Base in THF.

Preliminary $^{31}P\{^{1}H\}$ and Hydride Region $^{1}H$ NMR Study on the Reactivity of (5) Towards $H_2$ and Base in THF-$d_8$ FIG. 4 shows the combined spectra from the NMR study of the reactivity of (5) towards $H_2$ and base in THF-$d_8$ undertaken at $-$80° C. using ~1 atm Ar (bottom), RT using ~1 atm $H_2$ (middle) and RT using ~4 atm $H_2$ (top). Legend: Major Isomer of (5) (*); Minor Isomer of (5) (■); Peaks assigned to Ruthenium Mono-hydride Species, (●); Peak assigned to Ruthenium Dihydride, trans-$[Ru(H)_2(Ph_2P(CH_2)_2NH_2)_2]$, (✓)

Figure 5:
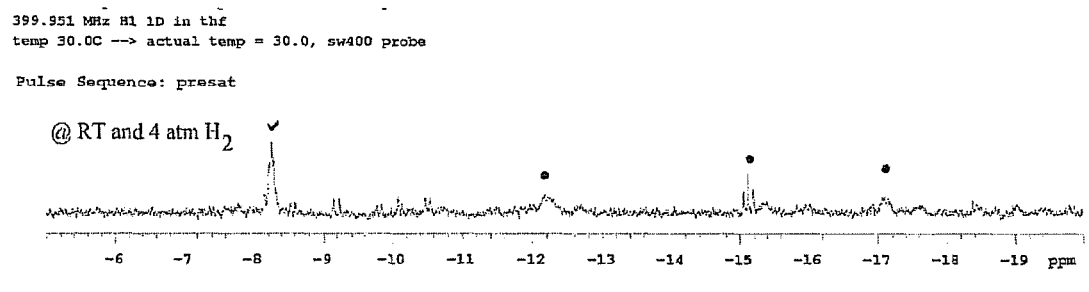
FIG. 5 graphically depicts preliminary $^1$H NMR Study on the reactivity of (5) towards H$_2$ and Base in THF.
Figure 5:
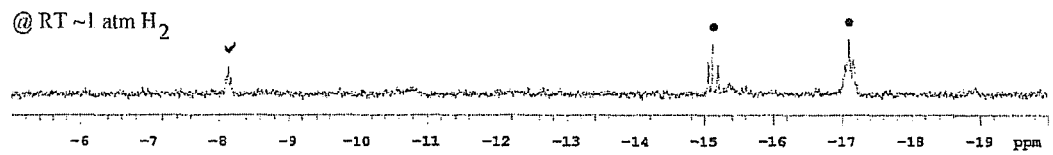
Figure 5:

FIG. 5 shows the combined spectra from the study of the reactivity of (5) towards $H_2$ and base in THF-$d_8$ undertaken at $-$80° C. using ~1 atm Ar (bottom), RT using ~1 atm $H_2$ (middle) and RT using ~4 atm $H_2$ (top). Legend: Ruthenium Mono-hydride Species, (●); Ruthenium Dihydride, trans-$[Ru(H)_2(Ph_2P(CH_2)_2NH_2)_2]$, (✓)

Figure 6:
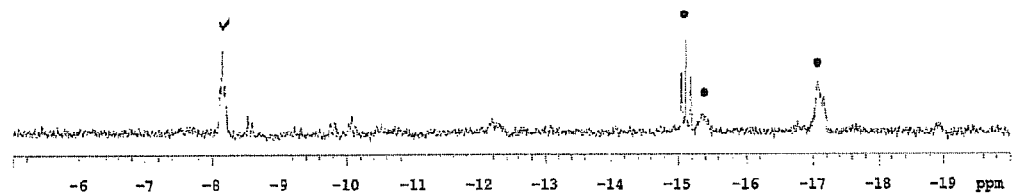
FIG. 6 graphically depicts the comparison of the hydride regions between (5) and (2) in THF-d$_8$.
Figure 6:
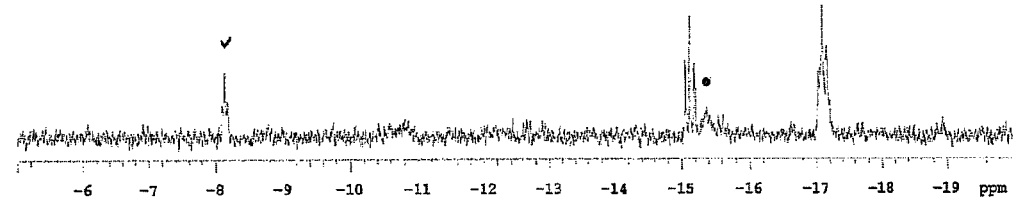
Figure 7:
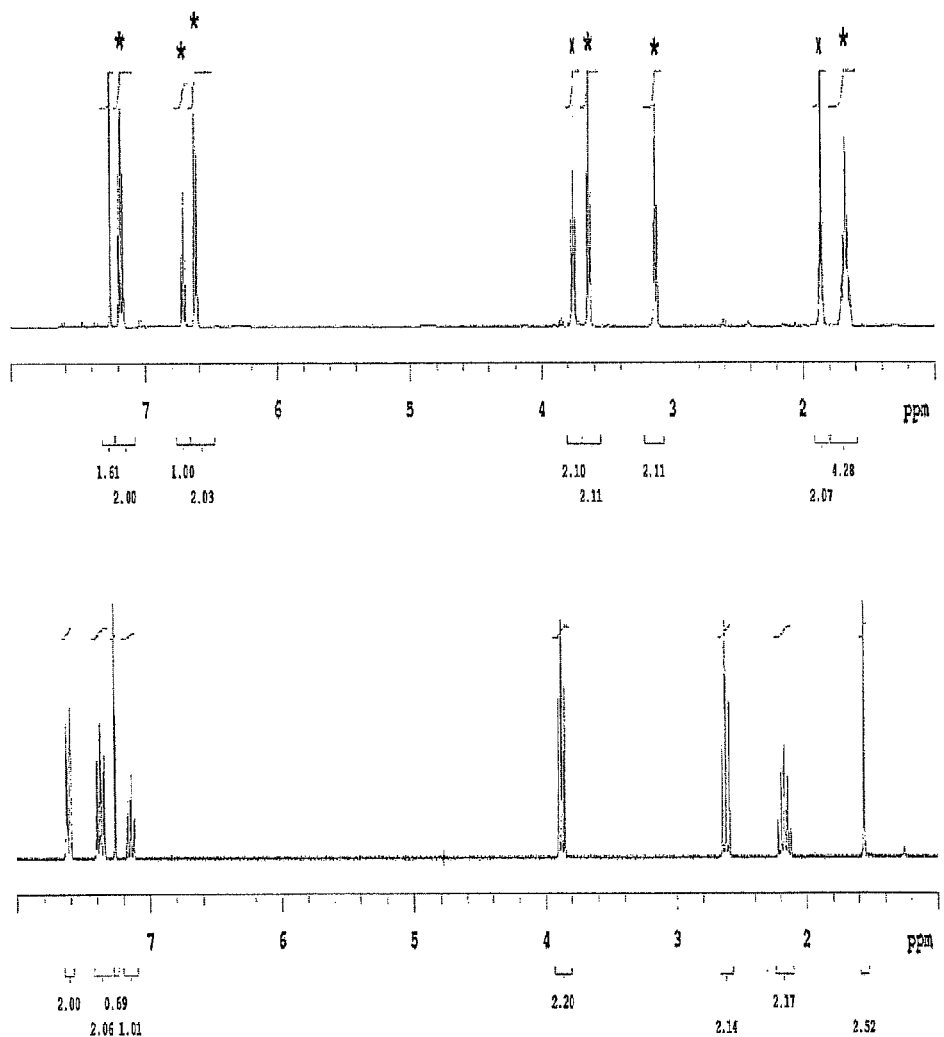
FIG. 7 graphically depicts the $^1$H NMR of the hydrogenation reaction of N-Phenylpyrrolidin-2-one (2c)
Figure 8:
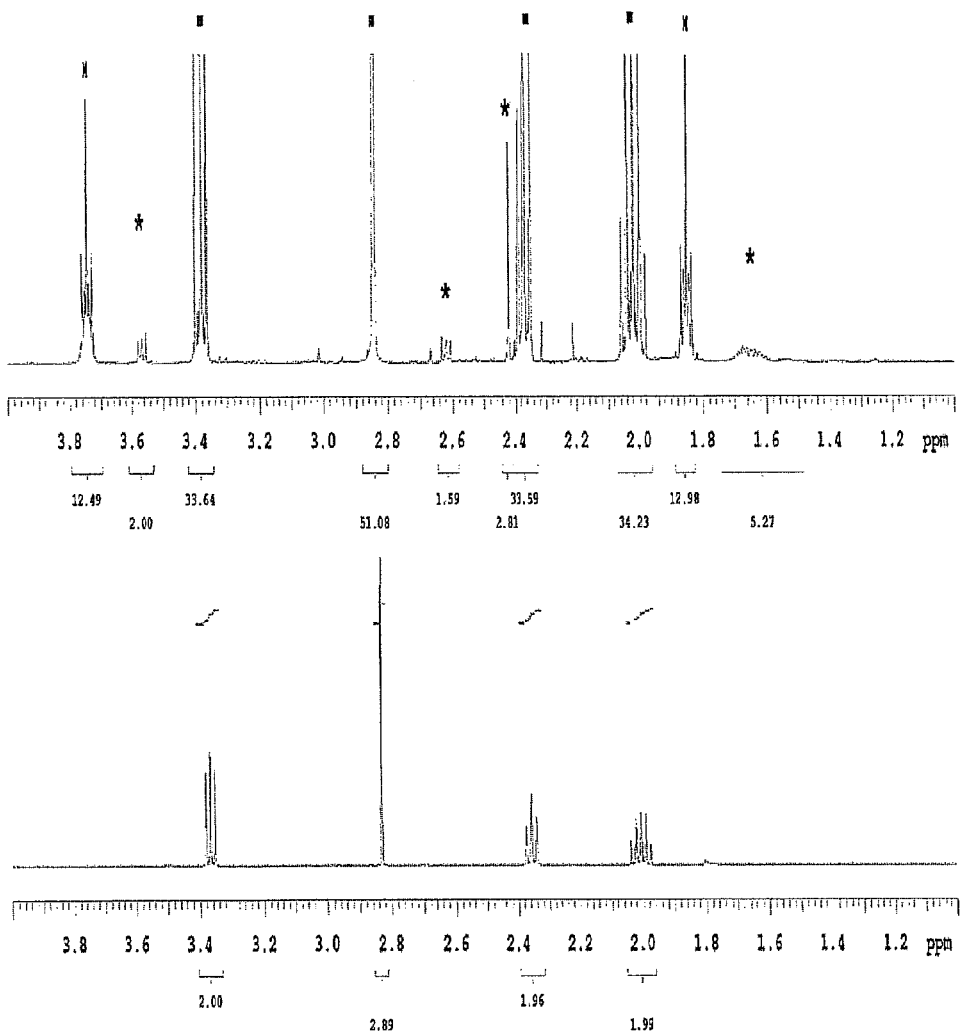
FIG. 8 graphically depicts the $^1$H NMR of the hydrogenation reaction of N-Methylpyrrolidin-2-one (2d)
Figure 9:
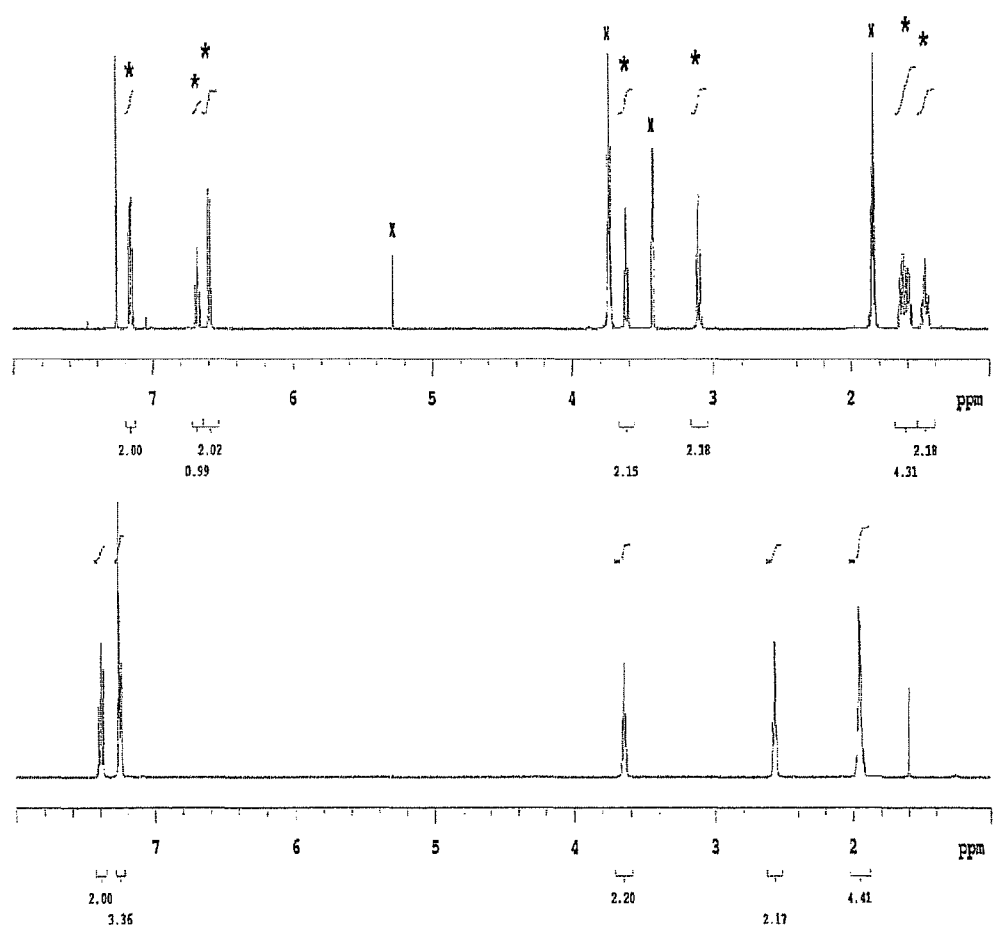
FIG. 9 graphically depicts the $^1$H NMR of the hydrogenation reaction of N-Phenylpiperidone (6)
Figure 10:
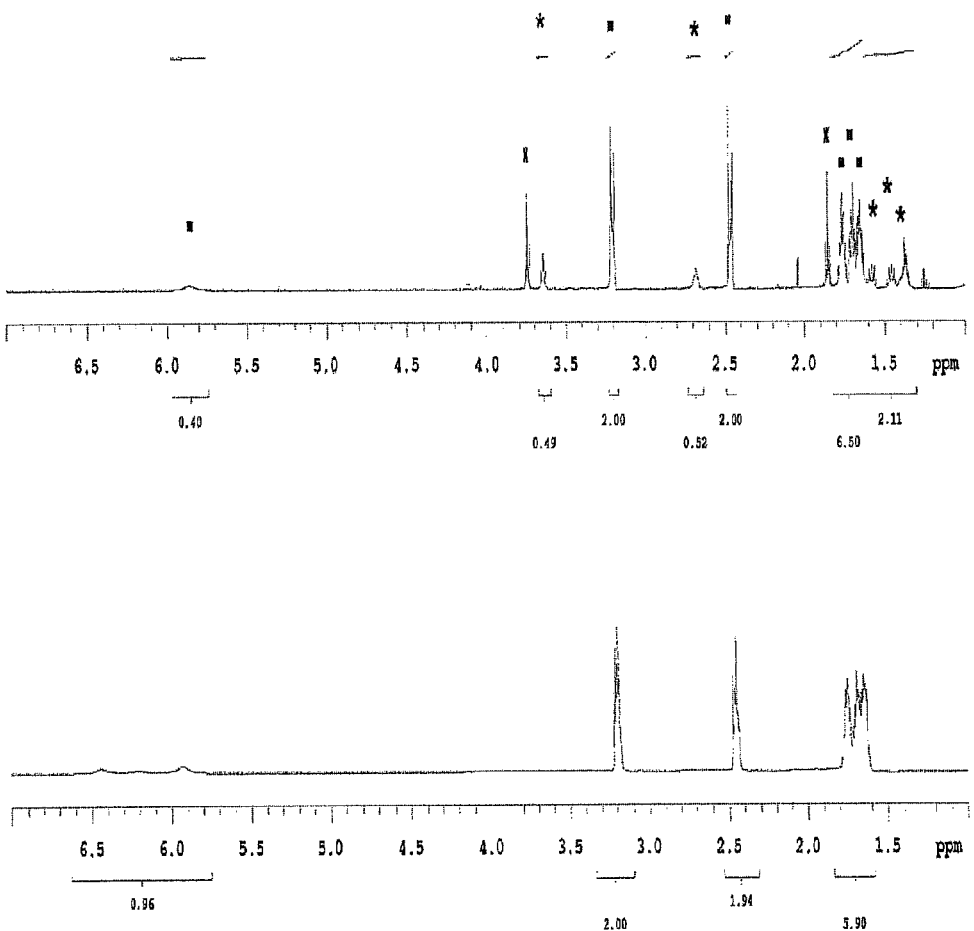
FIG. 10 graphically depicts the $^1$H NMR of the hydrogenation reaction of ε-Caprolactam (7)
Figure 11:
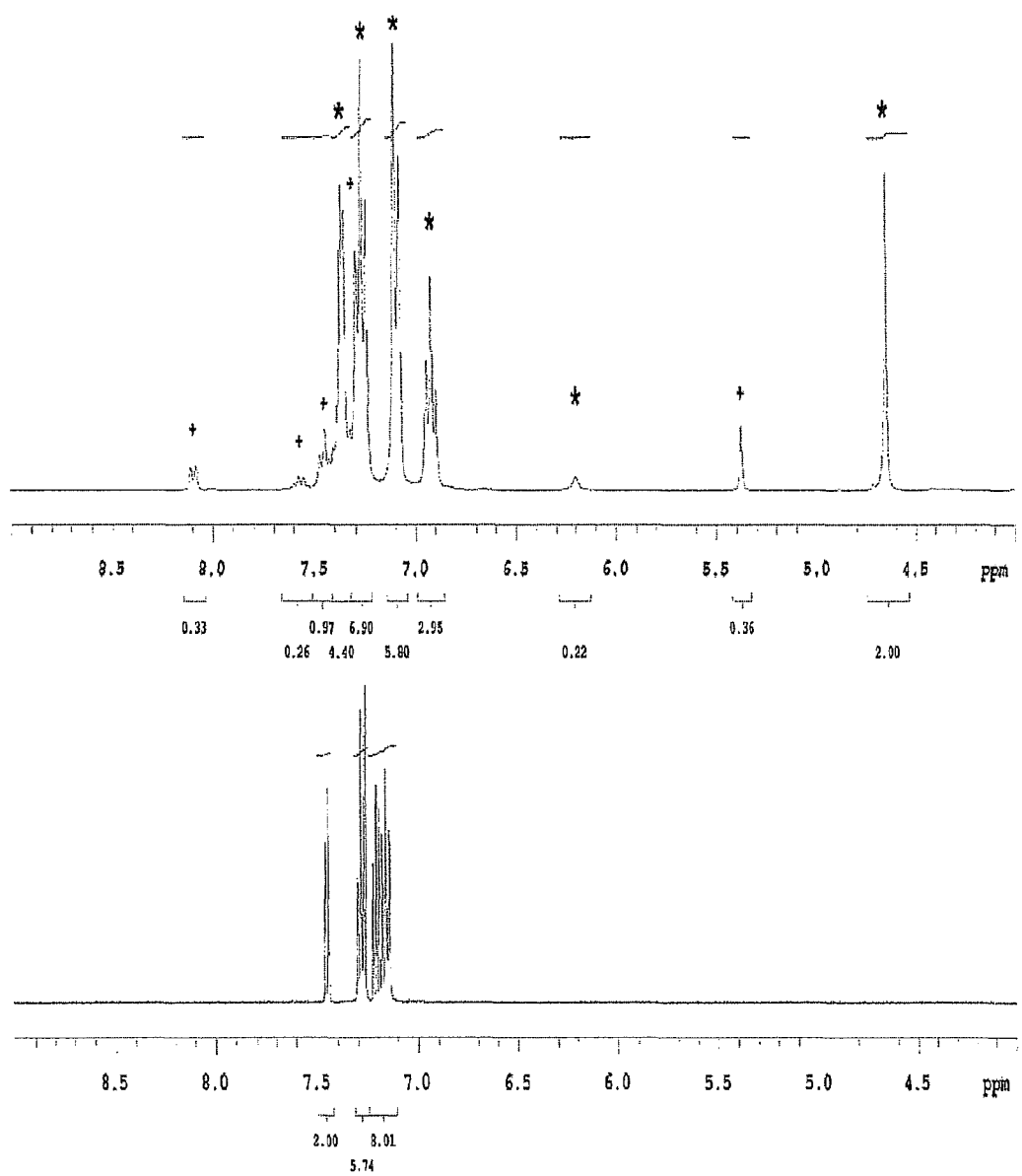
FIG. 11 graphically depicts the $^1$H NMR of the hydrogenation reaction of N,N-Diphenylbenzamide (8a), wherein trace benzyl benzoate formed is notated as (+)
Figure 12:
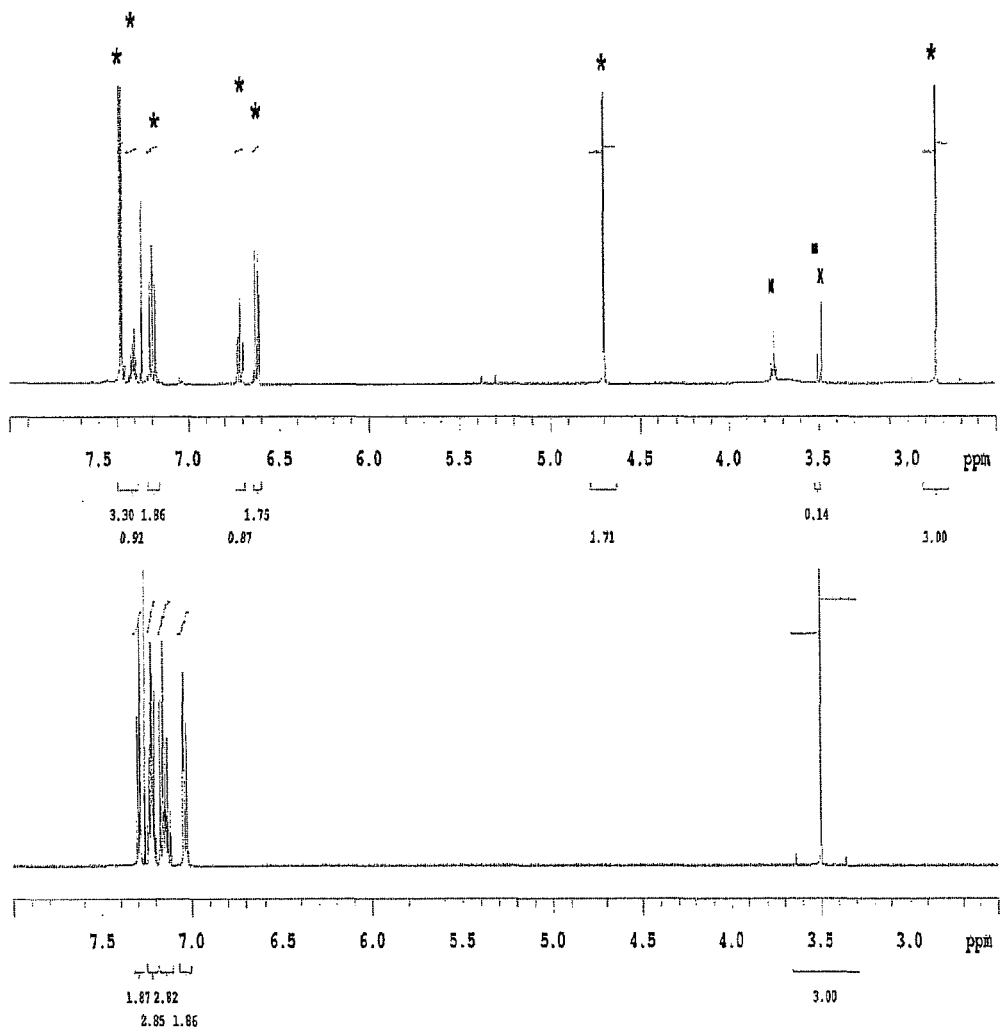
FIG. 12 graphically depicts the $^1$H NMR of the hydrogenation reaction of N-Methyl-N-Phenylbenzamide (8b)
Figure 13:
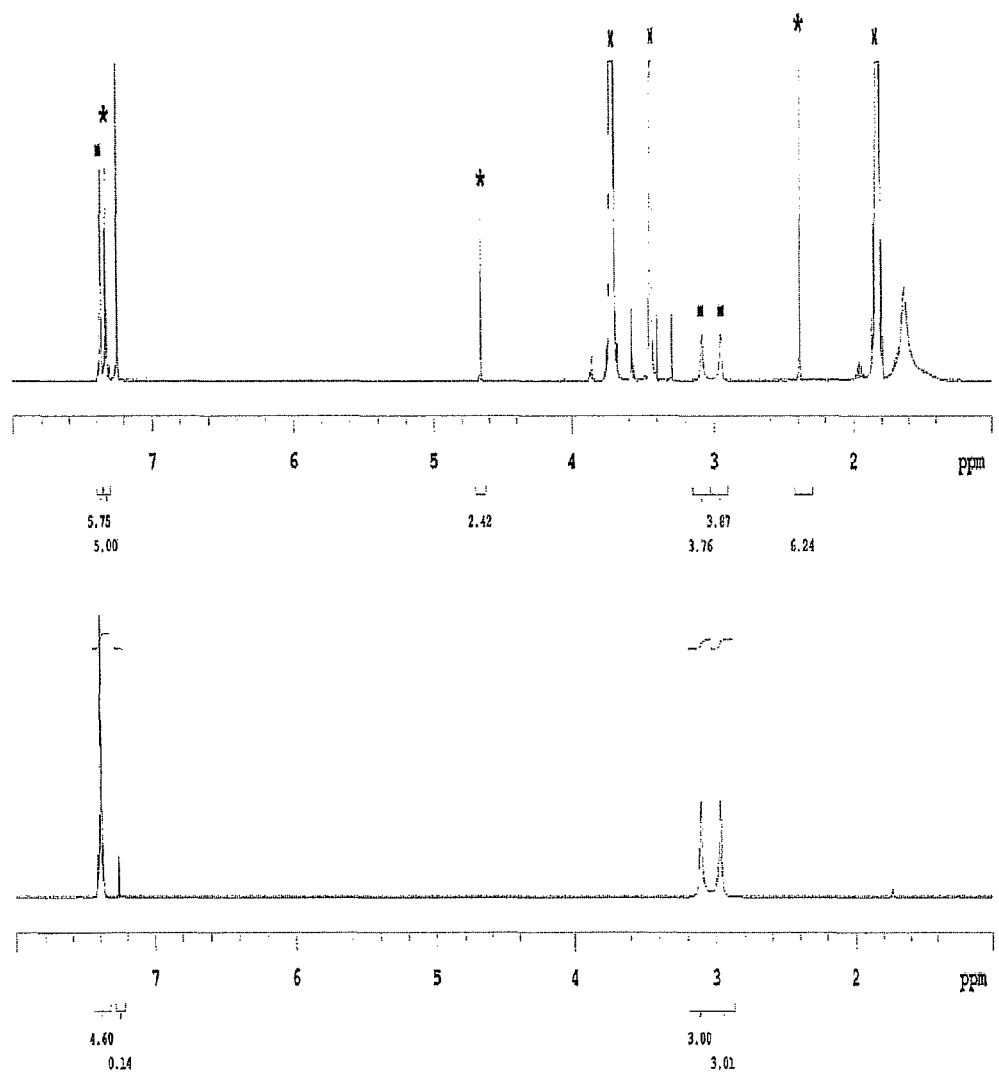
FIG. 13 graphically depicts the $^1$H NMR of the hydrogenation reaction of N,N-Dimethylbenzamide (8c)
Figure 14:
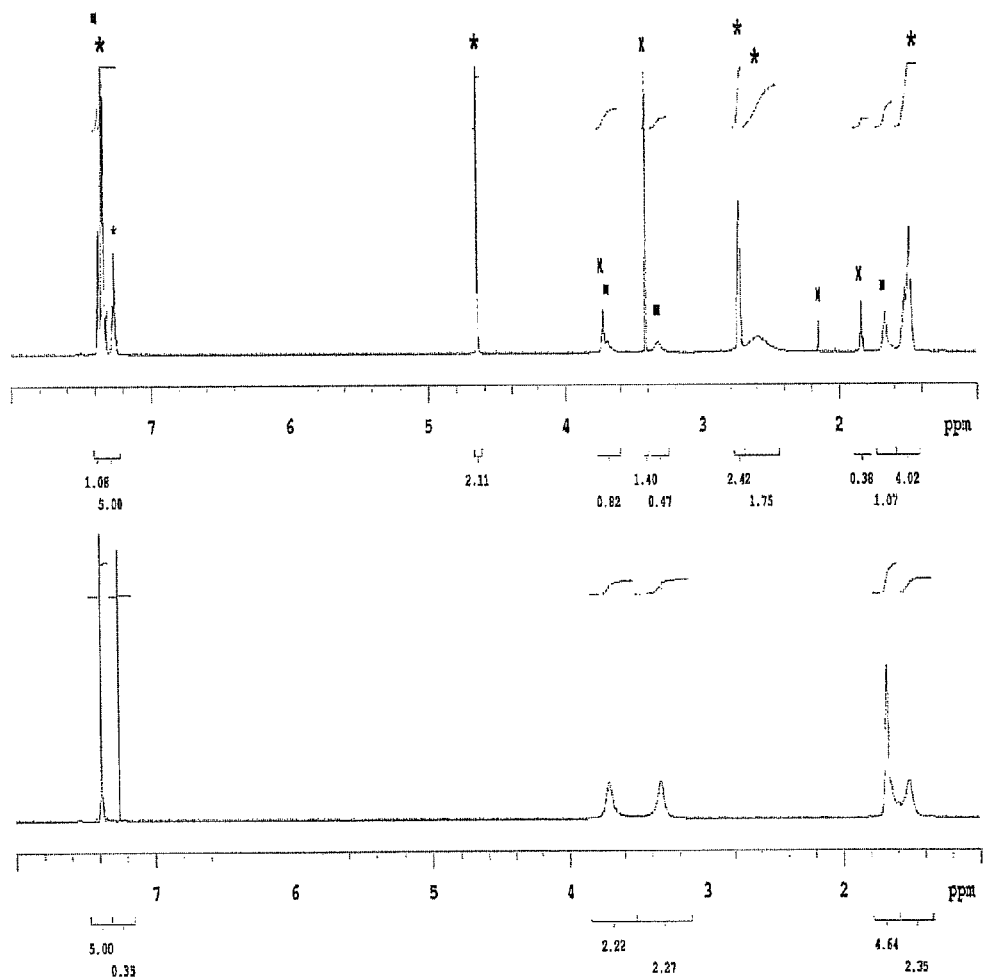
FIG. 14 graphically depicts the $^1$H NMR of the hydrogenation reaction of 1-Benzoylpiperidine (8d)
Figure 15:
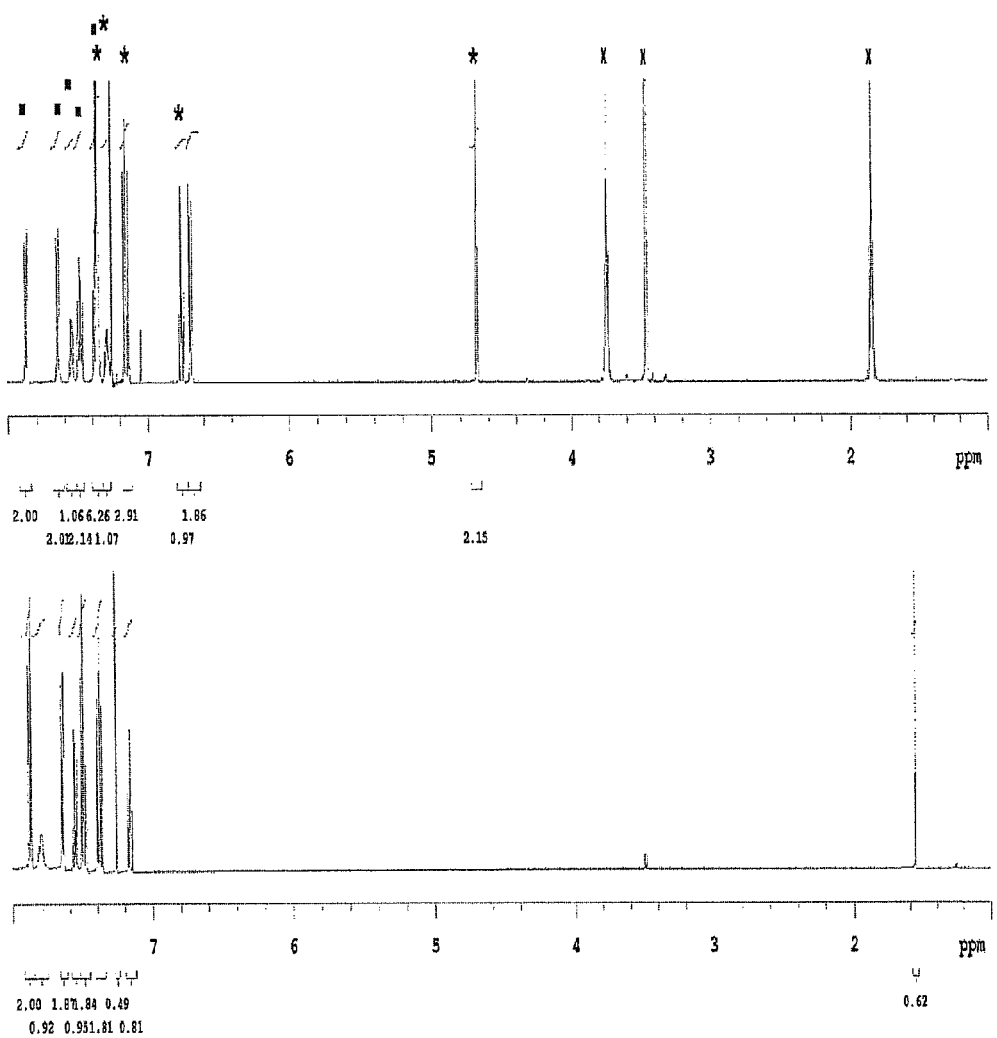
FIG. 15 graphically depicts the $^1$H NMR of the hydrogenation reaction of Benzanilide (8e)
Figure 16:
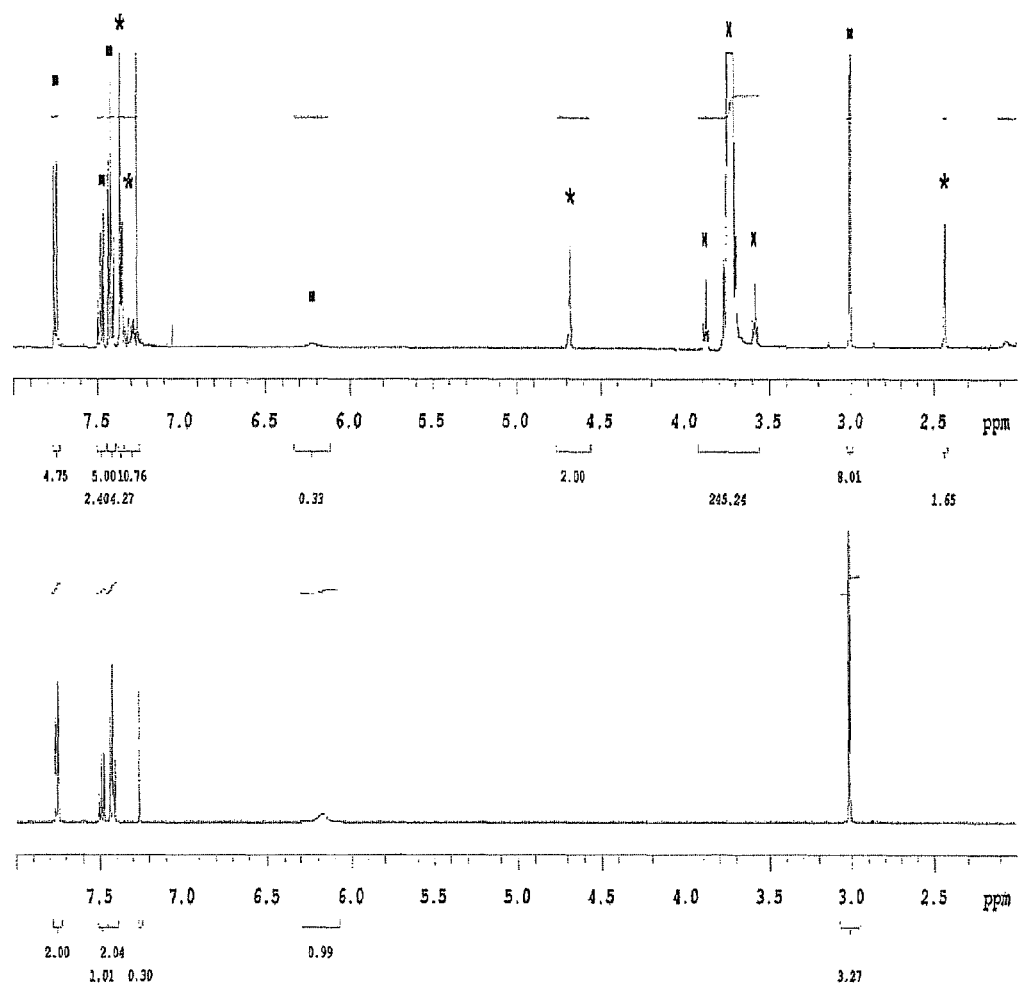
FIG. 16 graphically depicts the $^1$H NMR of the hydrogenation reaction of N-Methylbenzamide (8◯.
Figure 17:
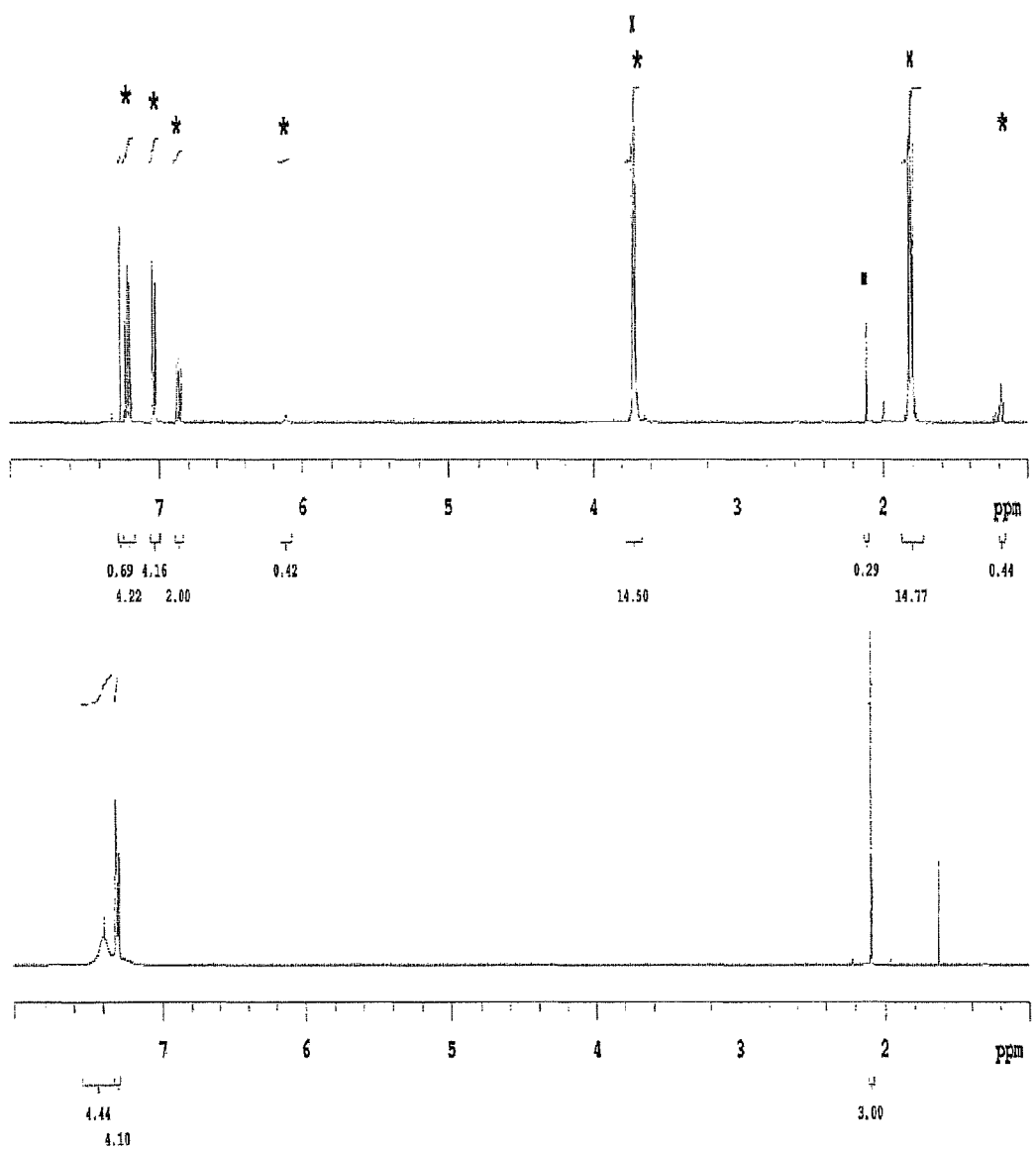
FIG. 17 graphically depicts the $^1$H NMR of the hydrogenation reaction of N,N-Diphenylacetamide (8g)
Figure 18:
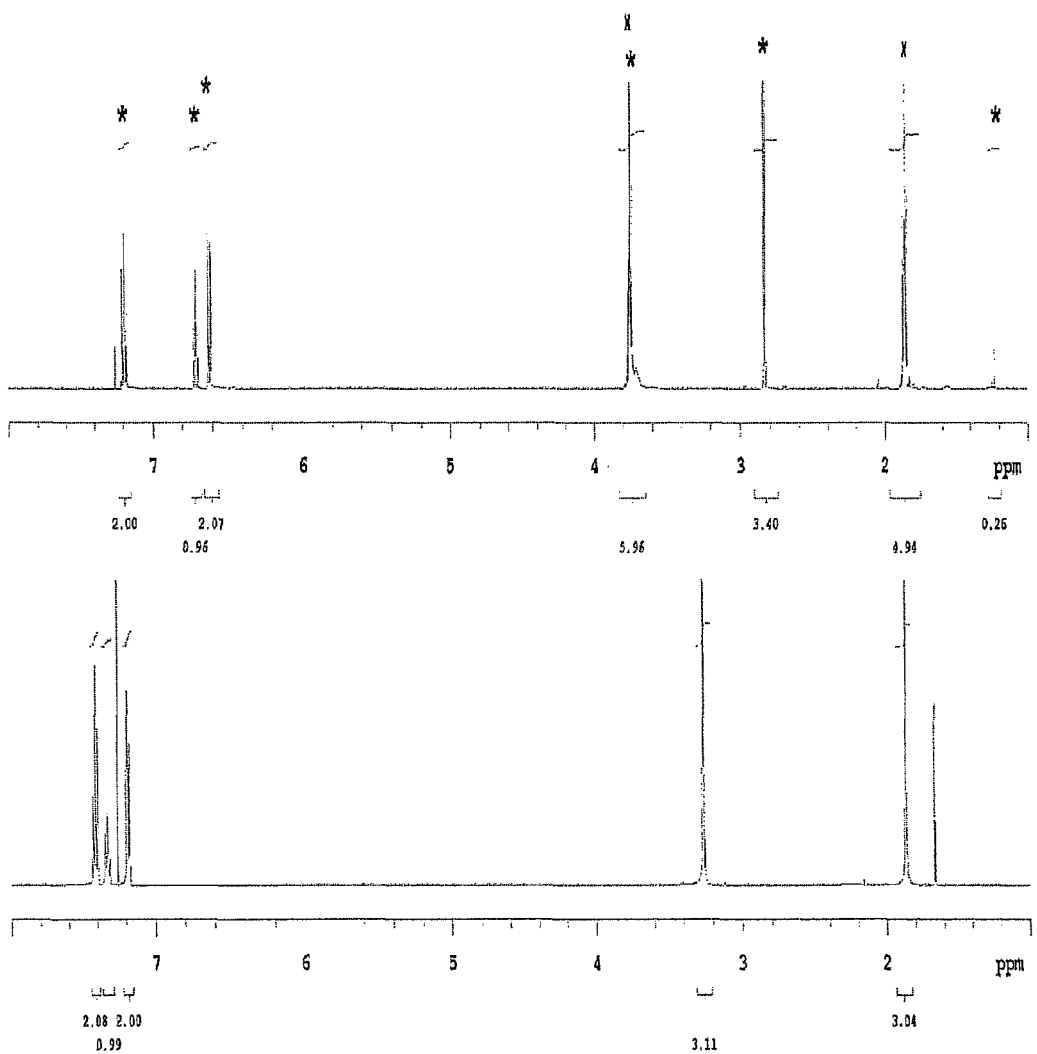
FIG. 18 graphically depicts the $^1$H NMR of the hydrogenation reaction of N-Methylacetanilide (8h)
Figure 19:
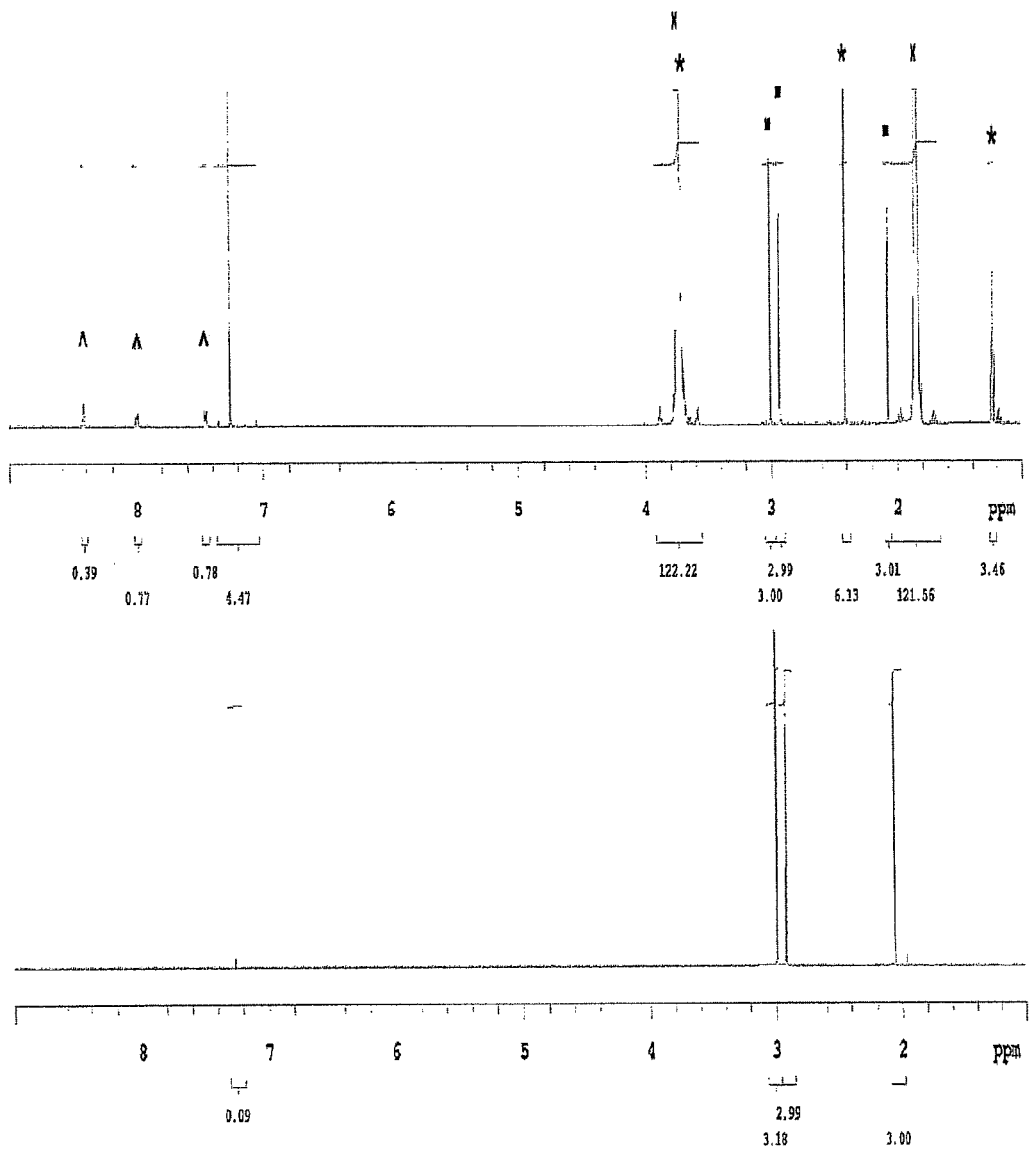
FIG. 19 graphically depicts the $^1$H NMR of the hydrogenation reaction of N,N-Dimethylacetamide (8i), wherein anthracene is used as an internal standard, notated as (^)
Figure 20:
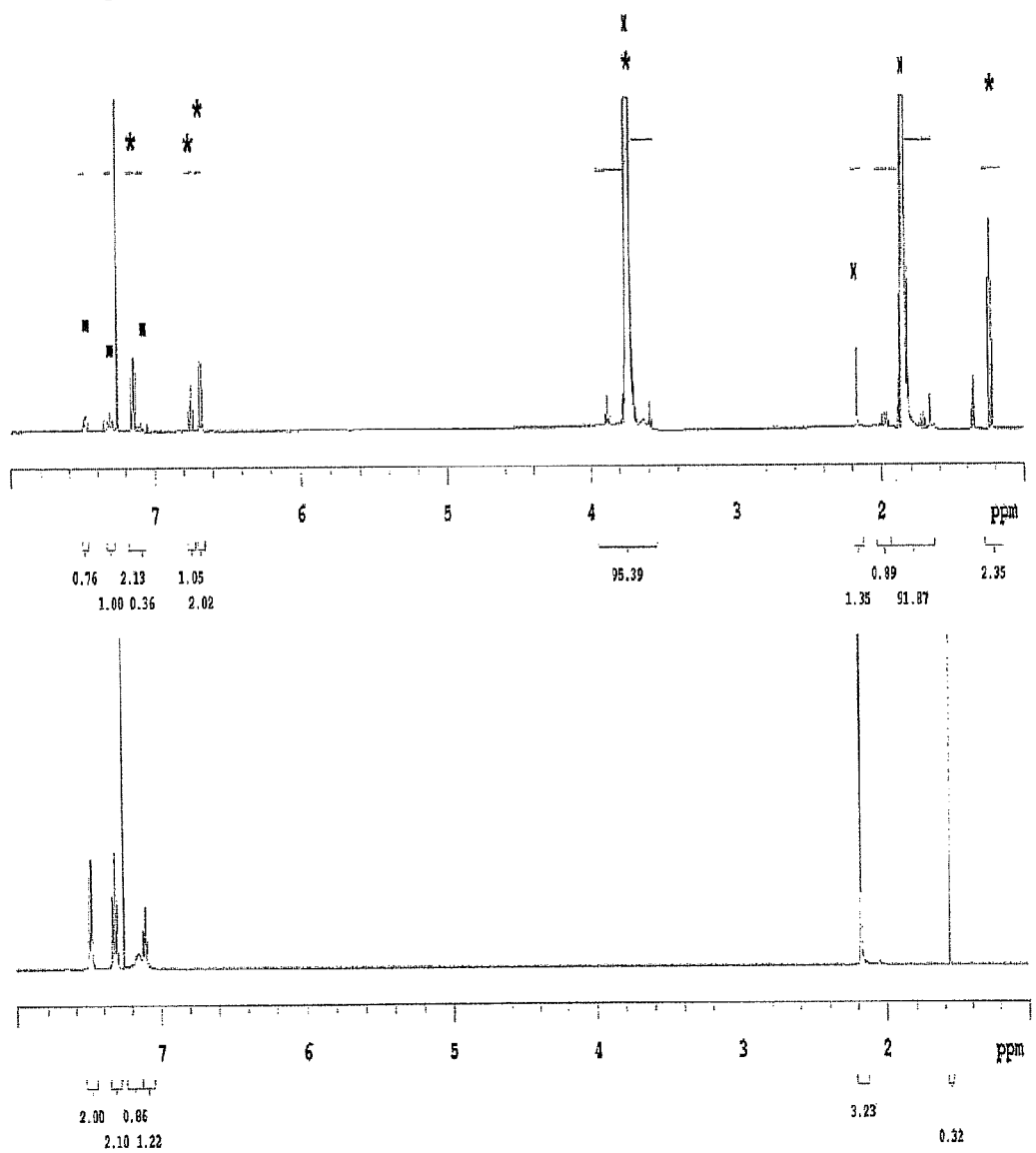
FIG. 20 graphically depicts the $^1$H NMR of the hydrogenation reaction of acetanilide (8j).

FIG. 6 shows a comparison of the hydride region between (5) and (11) using ~1 atm $H_2$ and $KN[(CH_3)_3Si]_2$ as Base in THF-$d_8$ at RT.

Example 3

Hydrogenation Reactions

General Conditions

All pressure reactions were carried out in a glass (for a maximum of 4 atmospheres {atm} of $H_2$ (g)) or stainless steel (for 50 atm $H_2$ (g)) autoclave equipped with a stir bar. Deuterated solvents were obtained from Cambridge Isotope Laboratories and Aldrich. Common solvents were distilled over appropriate drying reagents. (L. F. Armarego, C. L. L. Chai, *Purification of Laboratory Chemicals*, 6th Edition, Elsevier, Mass., 2009.) THF was distilled over sodium/benzophenone before each experiment. Toluene, and $CH_2Cl_2$ were distilled over $CaH_2$. Potassium bis(trimethylsilyl)amide (95%) and Sodium Methoxide (95%) were purchased from Aldrich and 2-(diphenylphosphino)ethylamine (95%) was purchased from Strem. These reagents were used as received. Other common laboratory chemicals and reagents were obtained from Aldrich, Alfa Aesar, TCI America, and Strem, and were used as received unless stated otherwise. Ultra high purity grade hydrogen gas was purchased from Praxair.

$^{1}H$, $^{13}C$, and $^{31}P$ NMR spectra were collected using Varian Inova (400 MHz), and Varian DirectDrive (500 MHz) spectrometers. $^{1}H$ and $^{13}C$ NMR chemical shifts are reported in parts per million (δ) relative to TMS with the respective solvent as the internal reference. $^{31}P$ NMR chemical shifts are reported in parts per million (δ) relative to 85% $H_3PO_4$ as the external reference. NMR peak assignments were made using gCOSY, and $^{1}H$-$^{13}C$ gHSQC NMR experiments. Abbreviations used in NMR spectra are s (singlet), d (doublet), t (triplet), q (quartet), p (pentet), m (multiplet), br (broad) and brs (broad singlet). High resolution mass spectra were taken using Applied BioSystems Mariner BioSpectrometry Workstation oaTOF mass spectrometer. Elemental analysis data were obtained using Carlo Erba CHNS-O EA1108 elemental analyzer.

General Procedure for the Hydrogenation of Solid Amides

The amide (5.0 mmol) was added to a stainless steel autoclave equipped with a magnetic stir bar. 4.0 mL of freshly distilled anhydrous THF was then added to the autoclave using a gas tight syringe. The atmosphere in the autoclave was flushed with $H_2$ (~2 atm for 3 min) at RT before adding the 1.0 mL THF solution of the catalyst precursor by cannula under $H_2$ pressure (~2 atm). Any residue in the NMR tube and cannula was washed into the autoclave with 3.0 mL of THF. The autoclave was then pressurised to 50 atm with $H_2$ and the reaction mixture stirred at 100° C. for 23 h. The autoclave was then allowed to cool to RT over 1 h before being vented slowly. MeOH was used to dissolve any precipitated products. The reaction yields were determined by $^1H$ NMR spectroscopy.

General Procedure for the Hydrogenation of Liquid Amides 4.0 mL of freshly distilled anhydrous THF was added to a stainless steel autoclave equipped with a magnetic stir bar. The atmosphere of the steel autoclave was the flushed with $H_2$ (~2 atm for 3 min) at room temperature. During this venting time a solution of the amide (5.0 mmol) in 1.0 mL of THF was prepared under Argon. Under $H_2$ pressure (~2 atm) the amide solution and 1.0 mL of the catalyst precursor solution were added to the autoclave punctuated by two 1.0 mL THF washes. The autoclave was then pressurized to 50 atm $H_2$ and the reaction mixture was stirred at 100° C. for 23 h. The autoclave was then allowed to cool to RT over 1 h before being vented slowly. MeOH was used to dissolve any precipitated products. The reaction yields were determined by $^1H$ NMR spectroscopy.

General Procedure for Hydrogenation of Amides Using Isolated (2) or (5) with NaOMe 2.50 μmol of the ruthenium precursor and 1.25 mmol of NaOMe were weighed out into two respective NMR tubes in a glove box. 1.0 mL of freshly distilled THF was then cannulated into each of these tubes under Argon. The NMR tubes were then shaken for 10 sec at RT and set aside. 25 mmol of the solid amide was then added to a stainless steel autoclave equipped with a magnetic stir bar. 5 mL of freshly distilled THF was then added to the autoclave using a gas tight syringe. The atmosphere in the autoclave was then flushed with $H_2$ (~2 atm for 3 min) at RT. The previously prepared 1.0 mL mixtures of the ruthenium catalyst and NaOMe were then sequentially cannulated into the steel autoclave followed by a 5 mL THF wash to remove any lingering residue. The autoclave was then pressurized to 50 atm with $H_2$ and the mixture stirred at 100° C. for 23 h. The autoclave was then allowed to cool to RT over 1 h before venting slowly. MeOH was used to dissolve any precipitated products. The reaction yields were determined by $^1H$ NMR spectroscopy.

Control Experiment: Ligand Free Hydrogenation 0.010 mmol of cis-[Ru(CH$_3$CN)$_2$(η$^3$-C$_3$H$_5$)(COD)]BF$_4$ (4), and 0.030 mmol of [(CH$_3$)$_3$Si]$_2$NK were weighed out into two respective NMR tubes in a glove box. 1.0 mL of freshly distilled THF was then cannulated into each of these tubes under Argon. The 1.0 mL THF mixture of cis-[Ru(CH$_3$CN)$_2$(η$^3$-C$_3$H$_5$)(COD)]BF$_4$, (4) was heated in a water bath at 60° C. with periodic shaking to dissolve the solid. The two NMR tubes were then set aside at RT. 0.10 mmol of the solid amide was then added to a stainless steel autoclave equipped with a magnetic stir bar. The atmosphere in the autoclave was then flushed with $H_2$ (~2 atm for 3 min) at RT. The previously prepared 1.0 mL mixtures of the ruthenium precursor and base were then sequentially cannulated into the steel autoclave punctuated by 3.0 mL THF washes to remove any lingering residue in the NMR tubes. The autoclave was then pressurised to 50 atm with $H_2$ and the mixture stirred at 100° C. for 17 h. The autoclave was then allowed to cool to RT over 1 h before venting slowly. The reaction yields were determined by $^1H$ NMR spectroscopy. Result: No apparent hydrogenation.

Control Experiment: Base Free Hydrogenation

A mixture of cis-[Ru(CH$_3$CN)$_2$(η$^3$-C$_3$H$_5$)(COD)]BF$_4$ (4), (0.010 mmol) and 2 equiv of Ph$_2$PCH$_2$CH$_2$NH$_2$ 3, (0.020 mmol) in freshly distilled anhydrous THF (1.0 in L) under Argon was heated in an NMR tube using water bath at 60° C. with periodic shaking for 30 min. The resulting solution was cooled for 1 min to 0° C. using an ice bath before cooling to −78° C. using a dry ice/acetone bath. $H_2$ (~2 atm) was cannulated into the NMR tube at −78° C. The tube was then shaken for 10 sec, and promptly returned to the bath. This shaking process was repeated nine times. The resulting yellow solution in the NMR tube was then set aside at −78° C.

The amide (0.10 mmol) was added to a stainless steel autoclave equipped with a magnetic stir bar. 4.0 mL of freshly distilled anhydrous THF was then added to the autoclave using a gas tight syringe. The atmosphere in the autoclave was flushed with $H_2$ (~2 atm for 3 min) at RT before adding the 1.0 mL THF solution of the catalyst precursor by cannula under $H_2$ pressure (~2 atm). Any residue in the NMR tube and cannula was washed into the autoclave with 3.0 mL of THF. The autoclave was then pressurised to 50 atm with $H_2$ and the reaction mixture stirred at 100° C. for 17 h. The autoclave was then allowed to cool to RT over 1 h before being vented slowly. The reaction yields were determined by $^1H$ NMR spectroscopy. Result: No apparent hydrogenation.

Control Experiment: Nano-Particle Mediated Hydrogenation 14.5 mg of Ruthenium Black (0.01 mmol assuming 7% of Ruthenium atoms are on the surface) and 0.10 mmol of the amide were added to a stainless steel autoclave equipped with a magnetic stir bar. The atmosphere in the autoclave was flushed with $H_2$ (~2 atm for 3 min) at RT before adding the 8.0 mL of freshly distilled THF by cannula under $H_2$ pressure (~2 atm). The autoclave was then pressurised to 50 atm with $H_2$ and the reaction mixture stirred at 100° C. for 17 h. The autoclave was then allowed to cool to RT over 1 h before being vented slowly. The reaction yields were determined by $^1H$ NMR spectroscopy. Result: 1 turnover (TO) of the substrate to N-cyclohexyl-2-pyrrolidinone. $^1H$ NMR agreed with those reported in the literature. (Y-H. Yang, M. Shi, *J. Org. Chem.* 2005, 70, 8645.)

Preliminary Studies on the Reactivity of (5) Towards Hydrogen in the Presence of [(CH$_3$)$_3$Si]$_2$NK in THF-d$_8$ 0.015 mmol of the catalyst (5) and 0.150 mmol (10 equiv) of [(CH$_3$)$_3$Si]$_2$NK were weighed out into two respective NMR tubes in a glove box. 0.5 mL of freshly distilled anhydrous THF-d$_8$ was then cannulated into each of these tubes under Argon. The NMR tubes were then shaken for 10 sec at RT to dissolve the solids before, cooling the solutions to −78° C. using a dry ice/acetone bath. The THF-d$_8$ solution containing the base was then cannulated in to the catalyst precursor solution using $H_2$ (~2 atm) at −78° C. The NMR tube was then shaken for 10 sec, and promptly returned to the −78° C. dry ice/acetone bath. This shaking process was repeated nine times. The resulting orange solution in the NMR tube was then set aside at −78° C. and the atmosphere in the glass autoclave was then flushed with $H_2$ (~2 atm for 3 min) at RT.

The previously prepared 1.0 mL THF-$d_8$ solution was added via cannula using $H_2$ (~2 atm). The glass autoclave was then pressurized to 4 atm $H_2$ and the reaction mixture was stirred at RT for 1 h. At the end of the reaction the autoclave was depressurized to ~2 atm and an aliquot (0.7 mL) taken immediately for NMR under ~1 atm $H_2$.

The reaction was repeated in an NMR tube equipped with a rubber septum using 0.010 mmol of the catalyst precursor, 0.10 mmol (10 equiv) [(CH$_3$)$_3$Si]$_2$NK and THF-$d_8$ (0.7 mL, distilled from Na under Argon) mixed under 1 atm $H_2$ at −78° C. The reaction was warmed gradually (from −80° C.) in the NMR probe until reaction occurred at 0° C.~RT.

Example 4

Hydrogenation of Cyclic Amides $^1$H NMR Characterization of Hydrogenation Products For the NMR Spectra of hydrogenation experiments, the peaks are identified by the following legend: Product peaks are notated by (*); Residual solvent peaks are notated by (X); Residual starting material peaks are notated by (■); Internal standard peaks are notated by (^); Side product peaks are notated by (+).

Hydrogenation with Catalyst (1)

The activity of (1) in the hydrogenation of N-substituted pyrrolidin-2-ones was tested towards the activated amides N-methylsulfonylpyrrolidin-2-one (2a) and N-acetylpyrrolidin-2-one (2b).

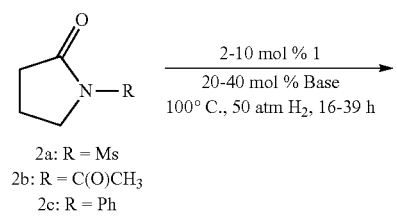

The reactivity of (1) was low to moderate. Compound (2a) was hydrogenated in only 27 turnovers (TO) to give the ring-opened N-methanesulfonyl amino alcohol product with 2 mol % Ru in THF (100° C., 50 atm, 20 mol % KOtBu, 39 h). Compound (2b) formed mixtures of pyrrolidine-2-one (major) and the ring-opened N-acetyl amino alcohol in ~45 TO using 2 mol % Ru (80° C., 50 atm $H_2$, 20 mol % KN[Si(CH$_3$)$_3$]$_2$, 16 h). N-phenylpyrrolidin-2-one (2c) did not react under these conditions.

These results contrast the high activity of (1) towards the reduction ketones, esters, and imides in THF. (S. Takebayashi, J. M. John, S. H. Bergens, *J. Am. Chem. Soc.* 2010, 132, 12832; S. Takebayashi, S. H. Bergens, PCT Int. Pat. Appl. WO 2010/145024 A1, Jun. 17, 2010; R. J. Hamilton, C. G. Leong, G. Bigam, M. Miskolzie, S. H. Bergens, *J. Am. Chem. Soc.* 2005, 127, 4152; R. J. Hamilton, S. H. Bergens, *J. Am. Chem. Soc.* 2006, 128, 13700; *J. Am. Chem. Soc.* 2008, 130, 11979; S. Takebayashi, S. H. Bergens, *Organometallics.* 2009, 28, 2349.)

Hydrogenation with Catalyst (5)

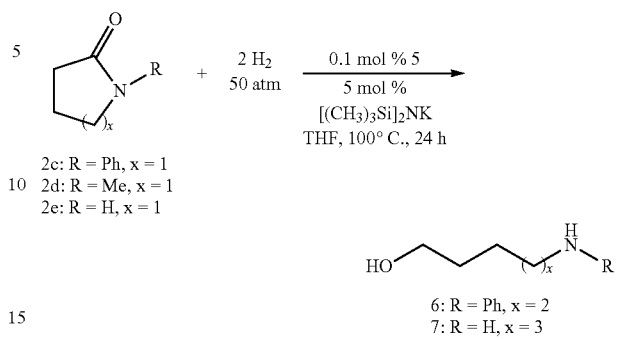

Various lactams were subjected to hydrogenating conditions using catalyst (5). Reactions were performed using in situ prepared catalyst (5). All hydrogenations were carried out with 0.1 mol % Ru, 4-5 mol % KN[Si(CH$_3$)$_3$]$_2$, 50 atm $H_2$, 100° C., for 24 h, 5/KN[Si(CH$_3$)$_3$]$_2$=1:50, [Substrate]= 0.626 M in THF. The results are summarized in Table 1. Yield was determined using $^1$H NMR. The results of these experiments are shown in FIGS. 7-10.

TABLE 1

| Entry | Substrate | Yield | Turnover |
|---|---|---|---|
| 1 | 2c | 100 | 1000 |
| 2 | 2d | 5 | 50 |
| 3 | 2e | 0 | 0 |
| 4 | 6 | 100 | 1000 |
| 5 | 7 | 23 | 230 |

N-phenylpyrrolidin-2-one, (2c) was hydrogenated to give N-phenyl-4-aminobutan-1-ol in 100% yield, or 1000 turnover (TO) under these conditions (Entry 1, Table 2). The N-Me ((2d), 50 TO, Entry 2) and N—H ((2e), 0 TO, Entry 3) derivatives were much less active than (2c), while the 6-membered, N-Ph derivative (6) reacted in 100% yield (1000 TO, Entry 4). The 7-membered unsubstituted lactam ((7), 230 TO, Entry 5) was more reactive than the 5-membered lactam (2e) (0 TO, Entry 3), as expected from the greater stability of 5- over 7-membered rings.

Another similar investigation was carried out using N-phenylpyrrolidin-2-one as the substrate with catalyst (5) or (11) and NaOMe as the base. The reactions were performed using in situ prepared catalyst (5) or (11). The reaction conditions were as follows: P(H$_2$)=50 atm, 100° C., (5) or (11)/NaOMe=1:500, [Substrate]=2.08 M in THF. Yield was determined by $^1$H NMR. Results are shown in Table 2, below.

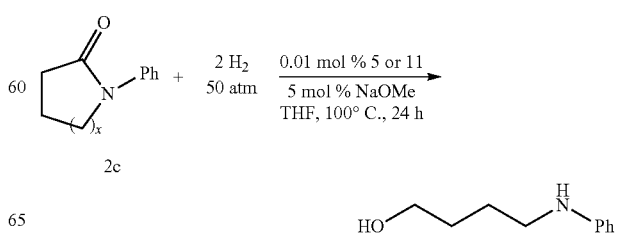

TABLE 2

| Entry | Catalyst Precursor | Yield | Turnover |
|---|---|---|---|
| 1 | 5 | 71.2 | 7120 |
| 2 | 11 | 67.6 | 6760 |

In preliminary experiments, it was found that catalyst (5) reacts with $H_2$ (~1 atm) and $KN[Si(CH_3)_3]_2$ (~3 equiv) in THF-$d_8$ starting at ~0° C. to form propylene and mainly three Rumono hydrides. (Overlap among the arene, N—H, and aliphatic $^1H$ NMR signals made a conclusive identification impossible. Their reactivity with $H_2$, and that they are formed from (5) and (2) suggests that they are isomers of the Ru-amide $[Ru(H)(Ph_2P(CH_2)_2NH_2)—(Ph_2P(CH_2)_2NH)]$ (10). The known dichloride $[Ru(Cl)_2(Ph_2P(CH_2)_2NH_2)_2]$ (2) gives a similar mixture of mono-hydride species under these conditions. (L. Saudan, C. M. Saudan, C. Debieux, P. Wyss, *Angew. Chem. Int. Ed.* 2007, 46, 7473; L. Saudan, P. Dupau, J. Riedhauser, P. Wyss, PCT Int. Pat. Appl. WO 2006/106484 A1, Oct. 12, 2006; PCT Int. Pat. Appl. WO 2006/106483, Apr. 4, 2006; L. Saudan, C. Saudan, PCT Int. Pat. Appl. WO 2008/065588 A1, Jun. 5, 2008; PCT Int. Pat. Appl. WO 2010/038209 A1, Apr. 8, 2010; L. Saudan, *Acc. Chem. Res.* 2007, 40, 1309.)

This mixture reacts further (~4 atm $H_2$, ~10 equiv KN[Si(CH$_3$)$_3$]$_2$) at RT to generate a symmetrical dihydride as major product that is tentatively assigned to be an isomer of trans-$[Ru(H)_2(Ph_2P(CH_2)_2NH_2)_2]$ (9). This preliminary assignment is based upon the similarities between the $^{31}P\{^1H\}$ and $^1H$ (hydride) NMR spectra between (9) and (1) (see R. J. Hamilton, C. G. Leong, G. Bigam, M. Miskolzie, S. H. Bergens, *J. Am. Chem. Soc.* 2005, 127, 4152; R. J. Hamilton, S. H. Bergens, *J. Am. Chem. Soc.* 2006, 128, 13700; *J. Am. Chem. Soc.* 2008, 130, 11979). The peaks for compound (9) were assigned using $^1H$, $^{31}P$, gCOSY, $^1H$-$^{31}P$ gHSQC and gTOCSY NMR experiments. $^{31}P\{^1H\}$ NMR –(161.903 MHz, THF-$d_8$, 27° C.): 56.2 ppm (s). $^1H$ NMR –(399.951 MHz, THF-$d_8$, 27° C.): δ –8.26 (Ru—H, t, J=14.8 Hz), δ 1.25, δ 2.43, δ 2.73).

Use of (4) as catalyst precursor, or (5) without added base (both at 10 mol %), did not result in hydrogenation. Further, use of Ru black (10 mol %) resulted only in hydrogenation of the arene ring in (2c). It is therefore unlikely that Ru nanoparticles are the active catalyst in these hydrogenations.

Saudan et al. reported that (2) forms an active ester hydrogenation catalyst with NaOMe as base in THF. (L. Saudan, C. M. Saudan, C. Debieux, P. Wyss, *Angew. Chem. Int. Ed.* 2007, 46, 7473; L. Saudan, P. Dupau, J. Riedhauser, P. Wyss, PCT Int. Pat. Appl. WO 2006/106484 A1, Oct. 12, 2006; PCT Int. Pat. Appl. WO 2006/106483, Apr. 4, 2006; L. Saudan, C. Saudan, PCT Int. Pat. Appl. WO 2008/065588 A1, Jun. 5, 2008; PCT Int. Pat. Appl. WO 2010/038209 A1, Apr. 8, 2010; L. Saudan, *Acc. Chem. Res.* 2007, 40, 1309.) Indeed, it was found that (5) and (2) (0.01 mol %) both hydrogenate (2c) in a remarkable 7120 and 6760 TO respectively in the presence of 5 mol % NaOMe (see Table 2).

Example 5

Proposed Mechanism for Hydrogenation of Amides

Again, while not wishing to be bound by theory, the following mechanism for the hydrogenation of amides with (9) (Scheme 2, below) is proposed. The first step is a bifunctional type addition of amide to (9) forming the Ru-(hemiaminaloxide) (12) as the net product. Base assisted elimination from (12) forms the Ru-amide (10), and the free hemiaminaloxide (13) which regenerates the base and eliminates aldehyde and H—NR$^1$$_2$. Addition of $H_2$ to (10) regenerates (9) and hydrogenation of the aldehyde forms the alcohol. Consistent with this mechanism is the formation of benzyl benzoate by the Tishchenko reaction of benzaldehyde during the hydrogenation of (8a) (Table 3).

Scheme 2: Proposed Mechanism for the Hydrogenation of Amides

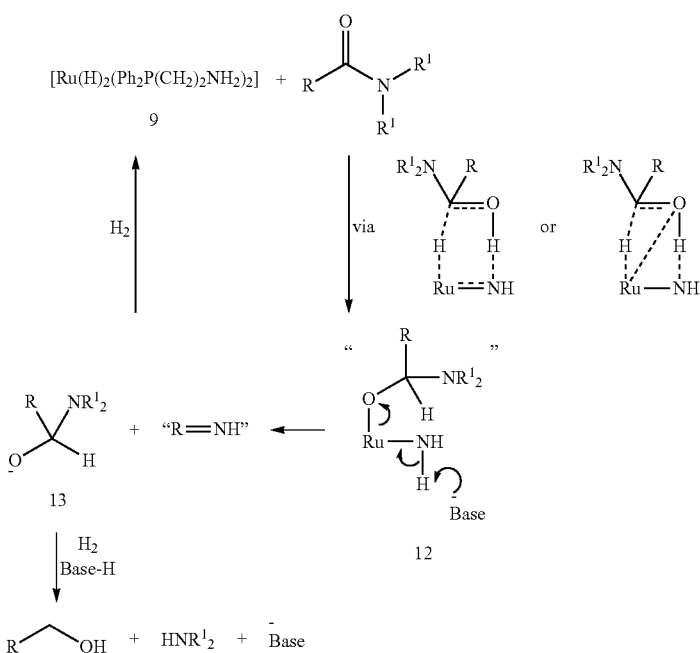

Catalysts (5) and (2) are active towards the hydrogenation of a series of amides without strongly activating functional groups. Significantly, the commonly inert, unfunctionalized amide dimethyl acetamide was hydrogenated in 500 turnover, and N-phenylpyrrolin-2-one was hydrogenated in up to 7120 turnover.

Example 6

Hydrogenation of Acyclic Amides

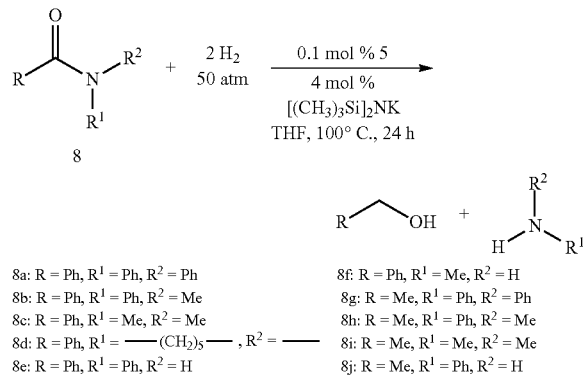

8a: R = Ph, $R^1$ = Ph, $R^2$ = Ph
8b: R = Ph, $R^1$ = Ph, $R^2$ = Me
8c: R = Ph, $R^1$ = Me, $R^2$ = Me
8d: R = Ph, $R^1$ = —(CH$_2$)$_5$—, $R^2$ = —
8e: R = Ph, $R^1$ = Ph, $R^2$ = H
8f: R = Ph, $R^1$ = Me, $R^2$ = H
8g: R = Me, $R^1$ = Ph, $R^2$ = Ph
8h: R = Me, $R^1$ = Ph, $R^2$ = Me
8i: R = Me, $R^1$ = Me, $R^2$ = Me
8j: R = Me, $R^1$ = Ph, $R^2$ = H

An investigation was carried out with an acyclic amides using (5) and KN[Si(CH$_3$)$_3$]$_2$. The reactions were performed using in situ prepared catalyst (5). The reaction conditions were as follows: P(H$_2$)=50 atm, 100° C., 5/KN[Si(CH$_3$)$_3$]= 1:40, [Substrate]=0.626 M in THF. Yield was determined by $^1$H NMR. For entry 1, the yield comprised 72% Benzyl Alcohol and 14% Benzyl Benzoate. For substrate (8i), anthracene was used as an internal standard. The results of these experiments are shown in FIGS. 11-20 and in Table 3.

TABLE 3

| Substrate | R | $R^1$ | $R^2$ | Yield (%) | Turnover |
|---|---|---|---|---|---|
| 8a | Ph | Ph | Ph | 100 | 1000 |
| 8b | Ph | Ph | Me | 96 | 960 |
| 8c | Ph | Me | Me | 50 | 500 |
| 8d | Ph | —(CH$_2$)$_5$— | — | 82 | 820 |
| 8e | Ph | Ph | H | 50 | 500 |
| 8f | Ph | Me | H | 27 | 270 |
| 8g | Me | Ph | Ph | 100 | 1000 |
| 8h | Me | Ph | Me | 100 | 1000 |
| 8i | Me | Me | Me | 50 | 500 |
| 8j | Me | Ph | H | 70 | 700 |

As shown in Table 3, the order of reactivity among the acyclic benzamides was —N(Ph)$_2$ (1000 TO) ~—N(Ph)Me (960 TO)>—N(Me)$_2$ (500 TO) (Substrates (8a)-(8c)). This order is consistent with the differences in the extent of donation from the lone pair on nitrogen to the carbonyl carbon among these substrates. 1-Benzoylpiperidine (820 TO, Substrate (8f) was more active than (8c) (500 TO), while secondary amides were somewhat less reactive than tertiary amides —N(Ph)H (500 TO, Substrate (8e)) vs —N(Ph)$_2$ (1000 TO, Substrate (8a)), and —N(Me)(H) (270 TO, Entry 6) vs —N(Me)$_2$ (500 TO, Substrate (8c)). Similar results were obtained with acyclic acetamides. Specifically, —N(Ph)$_2$ (1000 TO) ~—N(Ph)Me (1000 TO)>—N(Me)$_2$ (500 TO) (Substrates (8g) and (8h)). The secondary acetamide —N(Ph)H (700 TO, Substrate (8j)) was less reactive than the corresponding tertiary amide (1000 TO, Substrate (8h)). The lower reactivity of secondary- vs tertiary-amides may arise from reaction of the secondary amide with the added base.

Example 7

Base Free Hydrogenation

Base-free conditions are desirable in order to carry out hydrogenations of amides that contain functional groups that are sensitive to base, and to carry out certain enantioselective amide reductions. Compound (5) will react with 2 equivalents (Ru:B=1:2) in THF to generate a catalyst that is active for amide hydrogenations in the absence of added strong base.

Example of In Situ Catalyst Generation Using [Ru (η$^3$-C$_3$H$_5$)(Ph$_2$PCH$_2$CH$_2$NH$_2$)$_2$]—BF$_4$, (5), and 2 Equiv. NaBH$_4$

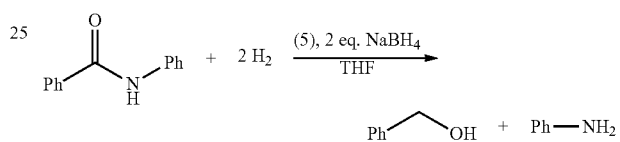

0.02 mmol (13.7 mg) of [Ru(η$^3$-C$_3$H$_5$) (Ph$_2$PCH$_2$CH$_2$NH$_2$)$_2$]BF$_4$ (5) and 0.04 mmol (1.5 mg) of NaBH$_4$ were weighed out into two separate NMR tubes in a glove box. This was immediately followed by the addition of 1.0 mL of freshly distilled THF to the NMR tube containing the ruthenium precursor. The contents of this NMR was then cannulated under ~2 atm H$_2$ into the NMR tube containing NaBH$_4$. The mixture was then heated at 60° C. for 20 min with periodic shaking. During this time the color of the solution intensified. At the same time, 1.0 mmol (0.1972 g) of benzanilide was added to a high pressure steel autoclave and the autoclave purged with H$_2$ for 20 min. 5 mL of fresh anhydrous THF was then cannulated into the steel autoclave followed by the 1 mL catalyst THF solution and a 2 mL THF wash. The high-pressure steel autoclave was then heated and pressurized to 100° C. and 50 atm of H$_2$ for 66 h. The autoclave was then allowed to cool to room temperature over the course of 1 h before taking an aliquot of the homogenous solution for $^1$H NMR. Results are shown in Table 4, below. All percentage conversions were determined using $^1$H NMR.

TABLE 4

| Entry | Temperature (° C.) | Pressure (atm H$_2$) | Time (h) | Conversion (%) | Turnover |
|---|---|---|---|---|---|
| 1$^a$ | 100 | 50 | 67 | 100 | 50 |
| 2$^b$ | 50 | 50 | 24 | 0 | 0 |
| 3$^a$ | 22 | 50 | 23 | 0 | 0 |

$^a$Performed using 2 mol % Ru in 8 mL of THF.
$^b$Performed using 0.1 mol % Ru in 10 mL of THF.

In some cases, the base-free catalyst is more active (or of comparable activity) than systems that employ the added strong base {KN[Si(CH$_3$)$_3$]$_2$}. The results that employ the use of this base (called base-assisted) are shown for comparison.

Substrate Screening

Base free conversions were carried out using 0.1 mol % Ru: [Ru(η³-C₃H₅)(Ph₂PCH₂CH₂NH₂)₂]BF₄ (5) and 2 equiv. of NaBH₄ in 10 mL THF at 100° C. and 50 atm H₂ for 24 h. The base assisted hydrogenations were performed using 0.1 mol % in situ prepared [Ru(η³-C₃H₅)(Ph₂PCH₂CH₂NH₂)₂]BF₄ (5). Reaction Conditions 50 atm H₂, [Ru(η³-C₃H₅)—(Ph₂PCH₂CH₂NH₂)₂]BF₄ (5)/K[N[Si(CH₃)₃]=1:40, [substrate]=0.626 M in THF. For the hydrogenation of dimethylacetamide, anthracene was used as an internal standard. (See: John, J. M.; Bergens, S. H. *Angew. Chem. Int. Ed.* 2011, 50, 10377.) All percentage conversions were determined using ¹H NMR. Results are shown in Table 5, below.

TABLE 5

| Substrate | Product | Base Free Conversion (%) | Base Free Turnover | Base Assisted Conversion (%) | Base Assisted Turnover |
|---|---|---|---|---|---|
| 1-phenylpyrrolidin-2-one | HO(CH₂)₄NHPh | 91 | 913 | 100 | 1000 |
| N,N-diphenylacetamide | MeOH + HN(Ph)₂ | 100 | 1000 | 100 | 1000 |
| N-methyl-N-phenylacetamide | MeOH + HN(Me)(Ph) | 93 | 935 | 100 | 1000 |
| 1-morpholinoethan-1-one | MeOH + morpholine | 96 | 964 | no data | no data |
| N-phenylacetamide | MeOH + H₂NPh | 80 | 806 | 70 | 700 |
| N,N-dimethylacetamide | MeOH + HNMe₂ | 24 | 248 | 50 | 500 |

Example of In Situ Catalyst Generation Using [Ru(η³-C₃H₅)(Ph₂PCH₂CH₂NH₂)₂]—BF₄, (5), and 2 Equiv. NaBH₄

Method was performed as above except for one modification. The high-pressure steel autoclave was heated and pressurized to 100° C. and 50 atm of $H_2$ for 23 h. The autoclave was then allowed to cool to room temperature over the course of 1 h before taking an aliquot of the homogenous solution for $^1$H NMR. The results are shown in Table 6.

TABLE 6

| Ruthenium Precursor | Ru:Ph₂P(CH₂)₂NH₂: NaBH₄:Substrate | Temp (° C.) | Pressure H₂ (atm) | Time (h) | Conversion (%) | Turnover |
|---|---|---|---|---|---|---|
| [Ru(COD)(Anthracene)]BF₄ | 1:2:5:1000 | 100 | 50 | 24 | 66 | 660 |
| [Ru(η³-C₃H₅)(COD)-(MeCN₂)]BF₄ | 1:2:5:1000 | 100 | 50 | 24 | 71 | 710 | pressurized to 100° C. and 50 atm of $H_2$ for 23 h. The autoclave was then allowed to cool to room temperature over the course of 1 h before taking an aliquot of a homogenous solution for $^1$H NMR.

Example 8

Precursor Screening

It was desirable to find a Ru-containing precursor that could reliably generate the active catalyst for P—P, P—N, and related ligand types. This screening experiment demonstrates that both [Ru(COD)(Anthracene)]BF₄ (3), and [Ru(η³C₃H₅)(COD)(MeCN)₂)]BF₄ (4), can generate in situ catalysts of similar, high activity using the ligand Ph₂P(CH₂)₂ NH₂ under base-free conditions.

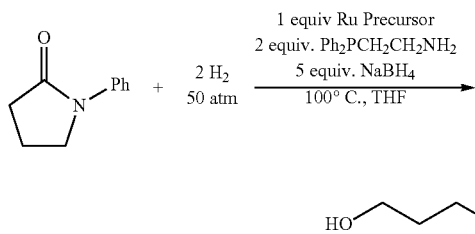

Example In Situ Catalyst Generation from [Ru(COD)(Anthracene)]BF4, (3)

0.02 mmol (9.5 mg) of [Ru(COD)(Anthracene)]BF₄ (3), and 0.10 mmol (3.8 mg) of NaBH₄ were weighed out into two separate NMR tubes in a glove box. 0.04 mmol (9.2 mg) of Ph₂PCH₂CH₂NH₂ was then added to the NMR tube containing the Ruthenium precursor via a syringe. This was immediately followed by the addition of 1.0 mL of freshly distilled THF. The NMR tube was then heated at 60° C. for 30 min with periodic shaking. The light yellow solution was then cannulated under ~2 atm $H_2$ into the NMR tube containing the solid NaBH₄. The mixture was then heated at 60° C. for 20 min during which the color of the solution because more intense. At the same time, 20.0 mmol (3.2216 g) of N-phenylpyrrolidinone was added to a high pressure steel autoclave and the autoclave purged with $H_2$ for 20 min. 5 mL of fresh anhydrous THF was then cannulated into the steel autoclave followed by the 1 mL catalyst THF solution and a 4 mL THF wash. The high-pressure steel autoclave was then heated and pressurized to 100° C. and 50 atm of $H_2$ for 23 h. The autoclave was then allowed to cool to room temperature over the course of 1 h before taking an aliquot of the homogenous solution for $^1$H NMR. The results are shown in Table 6.

Example 9

Chiral Hydrogenation

α-Chiral amide hydrogenations can be carried out using the present catalysts. An enantioselective amide hydrogenation that proceeds via a dynamic kinetic resolution at the carbon α-to the amide group has been investigated. In summary, the α-carbon in the substrate (shown below) is chiral. This C—H bond on this carbon centre is also weakly acidic, and rapidly racemizes in the presence of excess base during the catalytic hydrogenation. (dach=1,2-diaminocyclohexane)

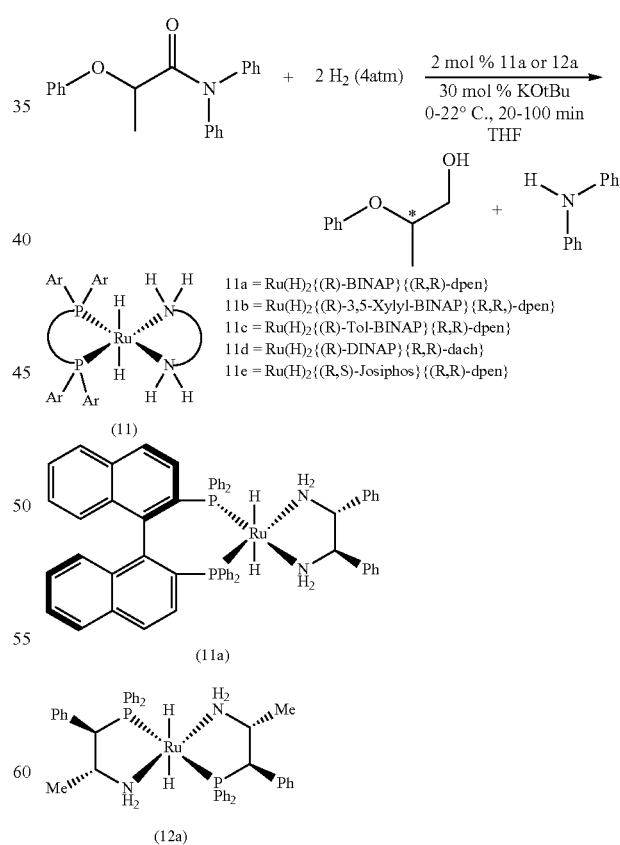

In these reactions, the excess base is 30% KOtBu. The C—H bond in the product alcohol is not acidic, and the carbon centre does not racemize in the product. Thus, a chiral catalyst can, in principle, hydrogenate one enantiomer of the above substrate to generate one enantiomer of the product. The leftover starting amide replenishes the reacted enantiomer via the base-catalyzed racemization, and so on, until all is converted into one enantiomer of the product alcohol.

These hydrogenation reactions, carried out with excess base, can proceed under conditions as mild as 0° C. under pressures as low as 4 atm $H_2$. Such conditions are extremely mild compared to those previously found, which often require high pressures of $H_2$ and high temperatures to proceed. The catalyst loadings used for these reactions were higher than those used with base.

General Procedure for the Hydrogenation of α-Chiral Amide Using $RuCl_2\{(R,R)(Ph_2PCH(Ph)CH(Me)NH_2\}_2$ 0.01 mmol (8.1 mg) of $RuCl_2\{(R,R)(Ph_2PCH(Ph)CH(Me)NH_2\}_2$ (12a), and 0.15 mmol (16.8 mg) of KOtBu were weighed out into two separate NMR tubes in a glove box. 1 mL of freshly distilled THF was then added to each of the NMR tubes and then shaken to dissolve the compounds. A low-pressure glass reactor was then charged with 0.5 mmol of amide and then purged for 10 min with $H_2$. The catalyst precursor solution was then cannulated into the reactor under $H_2$ followed by KOtBu solution and a 2 mL THF wash. The reactor was then pressurized to 4 atm $H_2$. The reaction was then monitored every 20 min by removing a sample and recording the $^1H$ NMR.

Several amides and catalysts have been screened using this reaction, and determined the enantiomeric excess of the product alcohols. The data obtained is summarized in table 7, below. Percentage conversion was determined by $^1H$ NMR. Percentage enantiomeric excess (ee) was determined by HPLC using CHIRALPAK TM IB Column, reaction conditions: 4 atm $H_2$, room temperature (22° C.), [Substrate]= 0.125 M (4 mL THF).

TABLE 7

| Catalyst | Temperature (° C.) | Time (min) | Conversion (%) | ee (%) |
|---|---|---|---|---|
| 11a | 22 | 20 | 100 | 58 |
| 11a | 0 | 100 | 100 | 60 |
| 11b | 22 | 20 | 100 | 54 |
| 11c | 22 | 20 | 100 | 63 |
| 11d | 22 | 80 | 100 | 57 |
| 11e | 22 | 100 | 100 | 18 |
| 12a | 22 | 30 | 100 | 1 |
| 12a | −80-22 | 1020 | 0 | 0 |

Substrate 1

The reaction conditions were carried out substantially as described above. The specific conditions for this experiment were: 4 atm $H_2$, room temperature (22° C.), [Substrate]= 0.125 M (4 mL THF). Results are shown in Table 8.

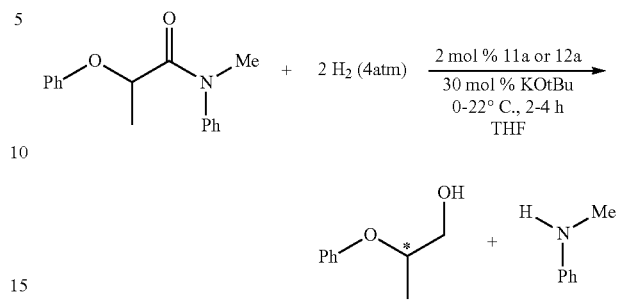

TABLE 8

| Catalyst | Substrate | Temperature (° C.) | Time (h) | Conversion (%) | ee (%) |
|---|---|---|---|---|---|
| 11a | 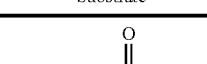 | 22 | 4 | 100 | Near zero |
| 12a |  | 22 | 2 | 100 | Near zero |

Substrate 2

The reaction conditions were carried out substantially as described above. The specific conditions for this experiment were: 4 atm $H_2$, room temperature (22° C.), [Substrate]= 0.125 M (4 mL THF). Results are shown in table 9, below.

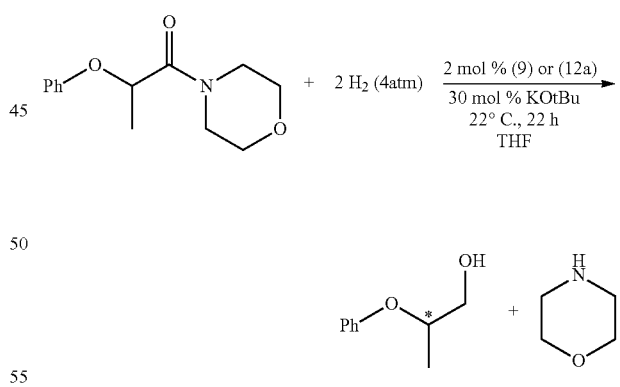

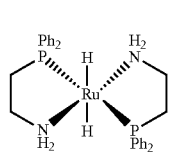

(9)

TABLE 9

| Catalyst | Substrate | Temperature (° C.) | Time (h) | Conversion (%) | Turnover | ee (%) |
|---|---|---|---|---|---|---|
| 12a | ![structure] | 22 | 22 | 69 | 35 | no data |
| 9 | ![structure] | 22 | 22 | 55 | 30 | no data |

Substrate 3

The reaction conditions were carried out substantially as described above. The specific conditions for this experiment were: 4 atm $H_2$, room temperature (22° C.), [Substrate] =0.025 M (4 mL THF). Results are shown in table 10, below.

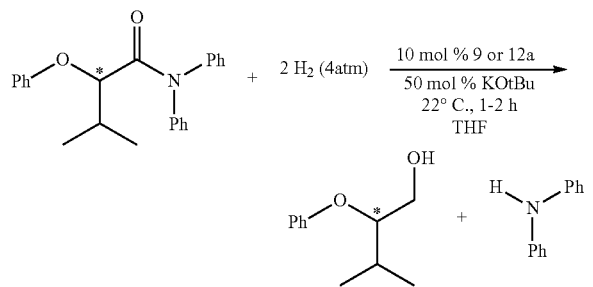

Table 10

| Catalyst | Substrate | Temperature (° C.) | Time (h) | Conversion (%) |
|---|---|---|---|---|
| 12a | ![structure] | 22 | 1 | 100 |
| 9 | ![structure] | 22 | 2 | 100 |

All publications, patents and patent applications mentioned in this Specification are indicative of the level of skill of those skilled in the art to which this invention pertains and are herein incorporated by reference to the same extent as if each individual publication, patent, or patent application was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. A process for the reduction of an amide bond in a substrate comprising contacting the substrate with:
   hydrogen gas; and
   a transition metal catalyst complex comprising a transition metal selected from Ru, Fe, Rh, Ir, Pd, Cu, Co, Pt, Ti, Zr, Os or Hf, and at least one to four ligands selected from the group consisting of:
   a bidentate diamino (N—N) ligand;
   a bidentate aminophosphine (P—N) ligand;
   a tridentate diaminophosphine (P—N—N) ligand;
   a tridentate aminodiphosphine (P—N—P) ligand; and
   a tetradentate diamino-diphosphine (P—N—N—P) ligand, and a monodentate amine (N) ligand;
   under conditions suitable to cleave the amide bond to give an amine and an alcohol;
   wherein said process is performed in one of the presence of a base or in the absence of base and wherein, when said process is performed in the absence of base, the process is performed in the presence of a sufficiently non-basic hydridic species, and wherein when said process is performed in the presence of a base, and the transition metal catalyst complex is present at an amount of 1 mol % or more, the process is performed using hydrogen gas at a pressure less than 10 atm; and
   wherein if the transition metal catalyst complex is cationic, the transition metal catalyst complex further comprises one or more suitable counteranions.

2. The process of claim 1, wherein the transition metal catalyst complex additionally comprises one or more ligands selected from the group consisting of a hydride ligand, a neutral monodentate ligand, and an anionic monodentate ligand.

3. The process of claim 1, wherein the bidentate diamino (N—N) ligand is

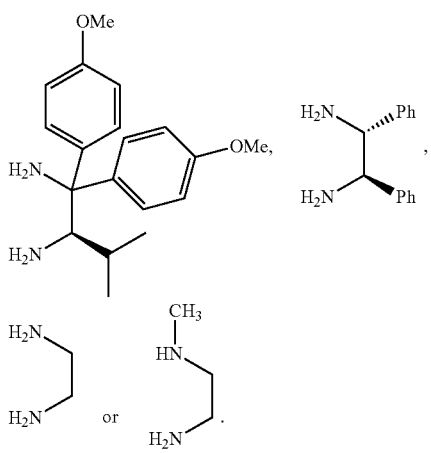

4. The process of claim 1, wherein the bidentate aminophosphine (P—N) ligand has the Formula (X)

$$PR^{36}R^{36}CHR^{35}CHR^{35}NH_2 \qquad (X)$$

wherein each $R^{35}$ is independently H, $(C_{1\text{-}10})$alkyl, $(C_{1\text{-}10})$ alkyl fluoro-substituted $(C_{1\text{-}4})$-alkyl, halo, $(C_{1\text{-}10})$cycloalkyl, fluoro-substituted $(C_{1\text{-}10})$cycloalkyl, $(C_{1\text{-}10})$-alkoxy, fluoro-substituted $(C_{1\text{-}10})$-alkoxy, unsubstituted and substituted phenyl and substituted and unsubstituted naphthyl, or adjacent substituents are joined together to form, including the carbon atoms to which they are attached, one or more unsubstituted or substituted phenylene, cyclohexylene, naphthylene, pyridylene or ferrocenylene groups, and each $R^{36}$ is independently $(C_{4\text{-}10})$ alkyl, $(C_{4\text{-}10})$ cycloalkyl, or phenyl, each of which may be optionally substituted.

5. The process of claim 1, wherein the transition metal catalyst complex is:

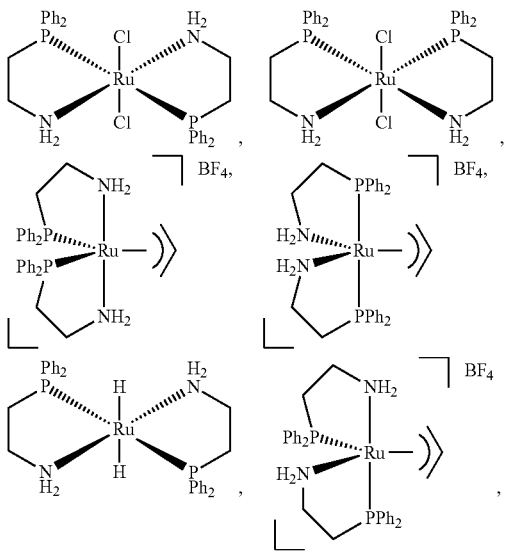

trans-[Ru((R)-BINAP)(H)$_2$((R,R)-dpen)], [Ru(Cl)$_2$(Ph$_2$P (CH$_2$)$_2$NH$_2$)$_2$], [Ru(Ph$_2$P CH$_2$CH$_2$NH$_2$)$_2$ ($\eta^3$-C$_3$H$_5$)] BF$_4$, trans-[Ru(H)$_2$ (Ph$_2$P(CH$_2$)$_2$NH$_2$)$_2$], [Ru(H)(Ph$_2$P (CH$_2$)$_2$NH$_2$) (Ph$_2$P(CH$_2$)$_2$NH)], [Ru(Cl)$_2$ (Cy$_2$PCH$_2$CH$_2$NH$_2$)$_2$] (Cy=cyclohexyl), or an isomer thereof.

6. The process of claim 1 wherein the transition metal catalyst complex is chiral.

7. The process of claim 1, wherein the process of the amide bond cleavage of the substrate produces:
   products that are enantiomerically enriched; and/or
   a chiral product.

8. The process of claim 1, wherein:
   (i) the process is performed in a solvent selected from tetrahydrofuran (THF), diethyl ether, chlorinated solvents, toluene and mixtures thereof;
   (ii) the hydrogen gas is used at a pressure in the range of from about 1 atm to about 100 atm or at a pressure under about 50 atm; or
   (iii) the process is performed in the presence of a base, and the transition metal catalyst complex is present at an amount of:
      a) 1 mol % or less;
      b) about 0.5 mol % or less;
      c) about 0.1 mol % or less; or
      d) from about 0.1 mol % to about 0.01 mol %.

9. The process of claim 8, wherein the process is performed at a temperature of 100° C. or less and the hydrogen gas is used at a pressure of 50 atm or less.

10. The process of claim 1, wherein the process is performed in the presence of a base, the transition metal catalyst complex is present at an amount less than about 10 mol %, the hydrogen gas is used at a pressure of about 4 atm or less and the process is carried out at a temperature of 0° C. or higher.

11. The process of claim 8, wherein the base is an organic non-coordinating base, a carbonate salt, a carboxylate salt, an alcoholate salt, a hydroxide salt, or a silazine salt.

12. The process of claim 11, wherein the base is tBuOK, or [(CH$_3$)$_3$Si]$_2$NK.

13. The process of claim 1, wherein the process is performed in the absence of base, and the hydrogen gas is used at a pressure less than about 10 atm, or less than about 5 atm, and, optionally, at a temperature of from about −50° C. to about 150° C.

14. A process for the reduction of an amide bond in a substrate comprising:
   contacting the substrate with hydrogen gas and a transition metal catalyst complex under conditions suitable to cleave the amide bond to give an amine and an alcohol,
   wherein the transition metal catalyst complex comprises at least one bidentate aminophosphine (P—N) ligand having the Formula (X)

$$PR^{36}R^{36}CHR^{35}CHR^{35}NH_2 \qquad (X)$$

wherein each $R^{35}$ is independently H, $(C_{1\text{-}10})$alkyl, $(C_{1\text{-}10})$alkyl fluoro-substituted $(C_{1\text{-}4})$-alkyl, halo, $(C_{1\text{-}10})$cycloalkyl, fluoro-substituted $(C_{1\text{-}10})$cycloalkyl, $(C_{1\text{-}10})$-alkoxy, fluoro-substituted $(C_{1\text{-}10})$-alkoxy, unsubstituted and substituted phenyl and substituted and unsubstituted naphthyl, or adjacent substituents are joined together to form, including the carbon atoms to which they are attached, one or more unsubstituted or substituted phenylene, cyclohexylene, naphthylene, pyridylene or ferrocenylene groups, and each $R^{36}$ is independently $(C_{4\text{-}10})$ alkyl, $(C_{4\text{-}10})$ cycloalkyl, or phenyl, each of which may be optionally substituted.

15. The process of claim 14 wherein the transition metal catalyst complex is

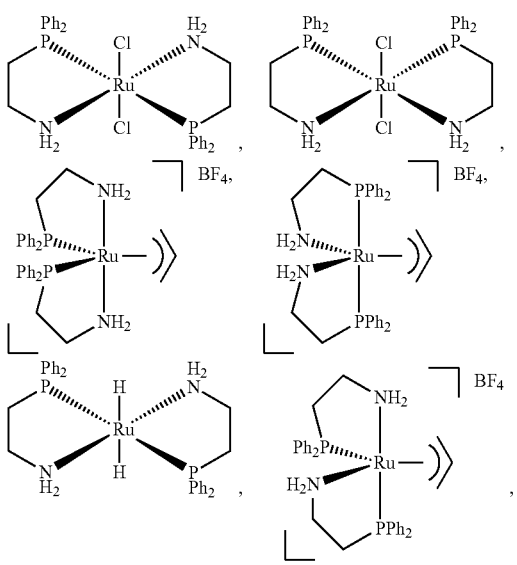

[Ru(Cl)$_2$(Ph$_2$P(CH$_2$)$_2$NH$_2$)$_2$], [Ru(Ph$_2$P CH$_2$CH$_2$NH$_2$)$_2$ (η$^3$-C$_3$H$_5$)]BF$_4$, trans-[Ru(H)$_2$(Ph$_2$P(CH$_2$)$_2$NH$_2$)$_2$], [Ru(H)(Ph$_2$P(CH$_2$)$_2$NH$_2$) (Ph$_2$P(CH$_2$)$_2$NH)], [Ru(Cl)$_2$(Cy$_2$PCH$_2$CH$_2$NH$_2$)$_2$] (Cy=cyclohexyl), or an isomer thereof.

16. The process of claim 14, wherein:

(i) the substrate is chiral;

(ii) the process produces products that are enantiomerically enriched, and/or (iii) the process produces a chiral product.

17. The process of claim 14, wherein:

(i) the process is performed in a solvent selected from tetrahydrofuran (THF), diethyl ether, chlorinated solvents, toluene and mixtures thereof;

(ii) the hydrogen gas is used at a pressure in the range of from about 1 atm to about 100 atm, or (iii) the process is performed in the presence of a base and the transition metal catalyst complex is present at an amount of 1 mol % or less.

18. The process of claim 14, wherein the process is performed in the presence of a base, the transition metal catalyst complex is present at an amount less than about 10 mol %, the hydrogen gas is used at a pressure of about 4 atm or less and the process is carried out at a temperature of 0° C. or higher.

19. The process of claim 17, wherein the base is an organic non-coordinating base, a carbonate salt, a carboxylate salt, an alcoholate salt, a hydroxide salt, or a silazine salt.

20. The process of claim 19, wherein the base is tBuOK or [(CH$_3$)$_3$Si]$_2$NK.

21. The process of claim 14, wherein:

(i) the transition metal catalyst complex is present at an amount of about 0.5 mol % or less, or about 0.1 mol % or less or from about 0.1 mol % to about 0.01 mol %;

(ii) the process is performed at a temperature of 100° C. or less and the hydrogen gas is used at a pressure of 50 atm or less;

(iii) the process is performed in the absence of base and the hydrogen gas is used at a pressure less than about 10 atm, or less than about 5 atm; and/or (iv) the process is performed at a temperature of from about −50° C. to about 150° C.

22. The process of claim 10, wherein the process is carried out at a temperature of from about 22° C. to about 0° C.

* * * * *